(12) United States Patent
Chan et al.

(10) Patent No.: US 11,999,950 B2
(45) Date of Patent: Jun. 4, 2024

(54) PRIMERS AND ASSAYS FOR LINKING REGIONS USING POLYMERASES

(71) Applicant: The Chinese University of Hong Kong, Shatin (HK)

(72) Inventors: Kwan Chee Chan, Hong Kong (CN); Wanxia Gai, Shenzhen (CN); Yuk-Ming Dennis Lo, Hong Kong (CN)

(73) Assignee: The Chinese University of Hong Kong, Shatin (HK)

( * ) Notice: Subject to any disclaimer, the term of this patent is extended or adjusted under 35 U.S.C. 154(b) by 438 days.

(21) Appl. No.: 16/871,754

(22) Filed: May 11, 2020

(65) Prior Publication Data

US 2020/0354785 A1 Nov. 12, 2020

Related U.S. Application Data

(60) Provisional application No. 62/846,149, filed on May 10, 2019.

(51) Int. Cl.
*C12N 15/10* (2006.01)
*C12Q 1/68* (2018.01)

(52) U.S. Cl.
CPC ..... *C12N 15/1093* (2013.01); *C12N 15/1031* (2013.01); *C12Q 1/68* (2013.01);
(Continued)

(58) Field of Classification Search
CPC ............ C12N 15/1093; C12N 15/1031; C12N 15/1075; C12Q 1/68; C12Q 2521/101; C12Q 2533/101; C12Q 2535/125
See application file for complete search history.

(56) References Cited

U.S. PATENT DOCUMENTS 6,204,025 B1  3/2001  Liu
2003/0190634 A1  10/2003  Barany et al.
(Continued)

FOREIGN PATENT DOCUMENTS

WO    2017070123 A1    4/2017

OTHER PUBLICATIONS

Pogulis et al. (Recombination and Mutagenesis by Overlap Extension PCR. In: Rapley, R. (eds) The Nucleic Acid Protocols Handbook. Springer Protocols Handbooks. Humana Press, Totowa, NJ., 2000. https://doi.org/10.1385/1-59259-038-1:857) (Year: 2000).*

(Continued)

*Primary Examiner* — Jeremy C Flinders
(74) *Attorney, Agent, or Firm* — Kilpatrick Townsend & Stockton LLP

(57) ABSTRACT

Particular forward and reverse primers may be used to link distant regions of the same large DNA molecule into a smaller DNA molecule. A reverse primer R1 can have a first portion complementary to an ending sequence of region A and can have a second portion having an overlapping sequence. A forward primer F2 can have a first portion complementary to a starting sequence of region B, where the forward primer includes a complementary overlapping sequence (e.g., the same first portion or a second portion) that is complementary to the overlapping sequence. The first portion of F2 may be the entire primer. The smaller DNA molecules can be used to determine haplotypes of regions. Kits including the particular forward and reverse primers are also described.

26 Claims, 26 Drawing Sheets

Specification includes a Sequence Listing.

(52) U.S. Cl.
CPC . *C12Q 2521/101* (2013.01); *C12Q 2533/101* (2013.01); *C12Q 2535/125* (2013.01)

(56) References Cited

U.S. PATENT DOCUMENTS

| | | |
|---|---|---|
| 2008/0194418 A1 | 8/2008 | Johnson et al. |
| 2015/0154352 A1* | 6/2015 | Johnson ................. C12Q 1/686 435/6.12 |

OTHER PUBLICATIONS

Warrens et al. (Gene, 1997, vol. 186 pp. 29-35) (Year: 1997).*
Jespersen et al. (BioTechniques, 1997, 23:48-52) (Year: 1997).*
Liang et al. (Nucleic Acids Research, 2017, 45(11):e94) (Year: 2017).*
Wetmur et al. (Nucleic Acids Research, 2005, 33(8):2615-2619 (Year: 2005).*

International Search Report and Written Opinion dated Aug. 10, 2020 in International Patent Application No. PCT/CN2020/089560. 9 pages.
Kadkhodaei, Saeid et al.; "Multiple overlap extension PCR (MOE-PCR): an effective technical shortcut to high throughput synthetic biology"; RSC Advances 2016; vol. 6; pp. 66682-66694.
Waneskog, Marcus et al.; "Multi-fragment site-directed mutagenic overlap extension polymerase chain reaction as a competitive alternative to the enzymatic assembly method"; Analytic Biochemistry; Jan. 1, 2014; Epub Sep. 29, 2013; vol. 444; pp. 32-37.
Geu-Flores, Fernando et al.; "USER fusion: a rapid and efficient method for simultaneous fusion and cloning of multiple PCR products"; Nucleic Acids Research; 2007; vol. 35, No. 7; e55; doi:10.1093/nar/gkm106; 6 pages.
Cantsilieris, Stuart et al.; Targeted Capture and High-Throughput Sequencing Using Molecular Inversion Probes (MIPs); Methods in Molecular Biology; HHS Public Access Author Manuscript; 2017; vol. 1492; pp. 95-106 (manuscript: 11 pages).
Illumina, Inc.; "Illumina Adapter Sequences"; Feb. 2016; Document #1000000002694 v01; 38 pages.

* cited by examiner

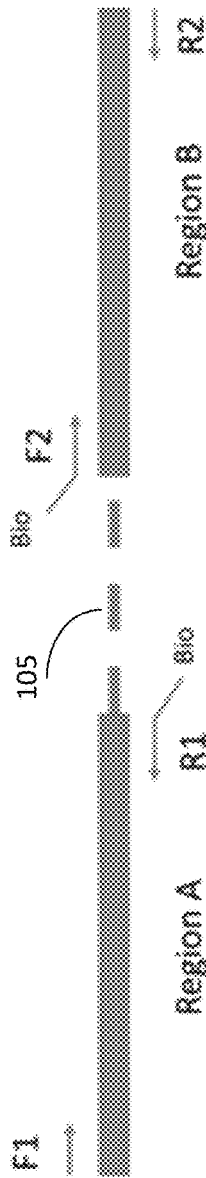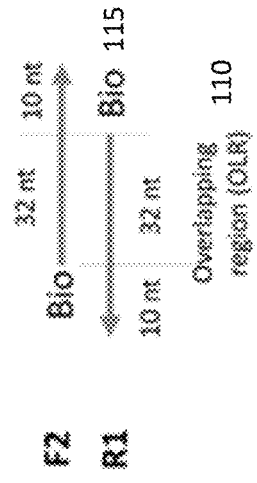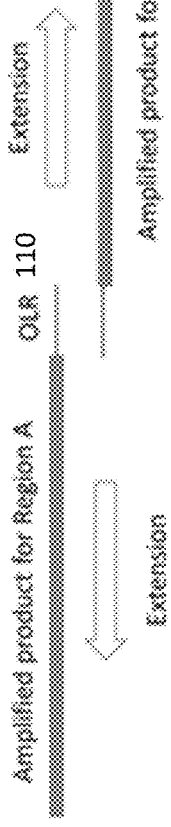
FIG. 1A
FIG. 1B
FIG. 1C
FIG. 1D

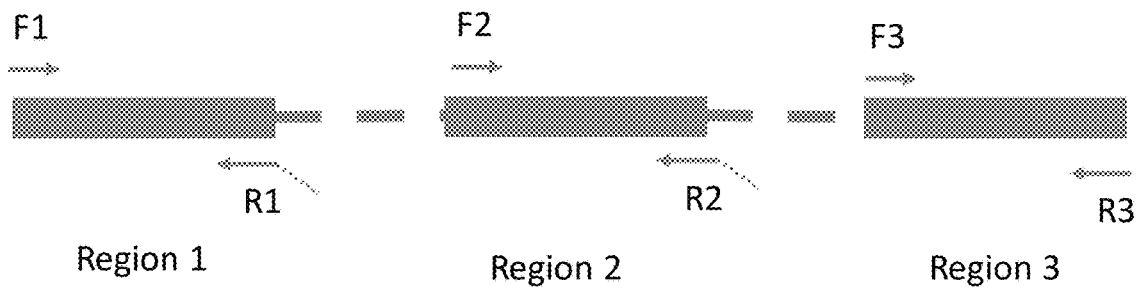
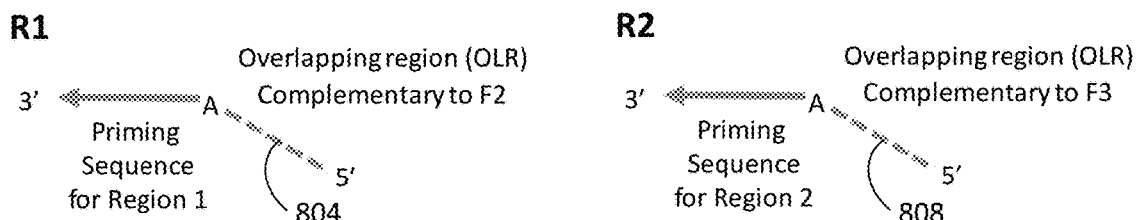
FIG. 8A
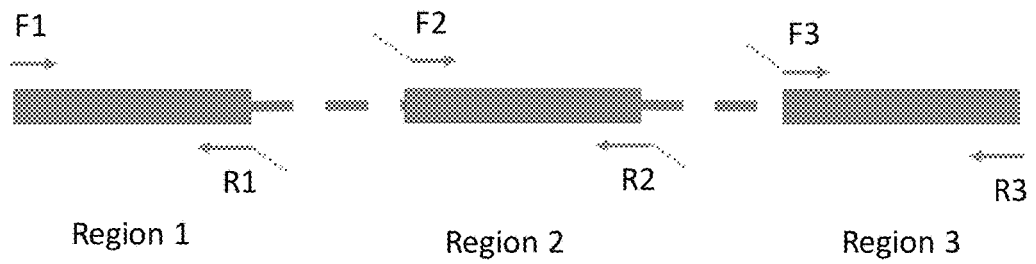
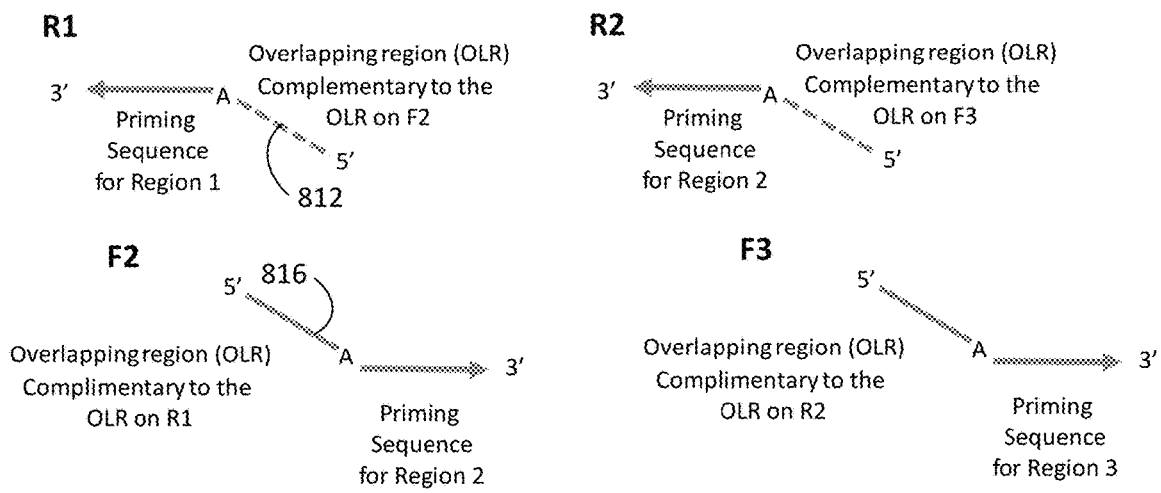
FIG. 8B

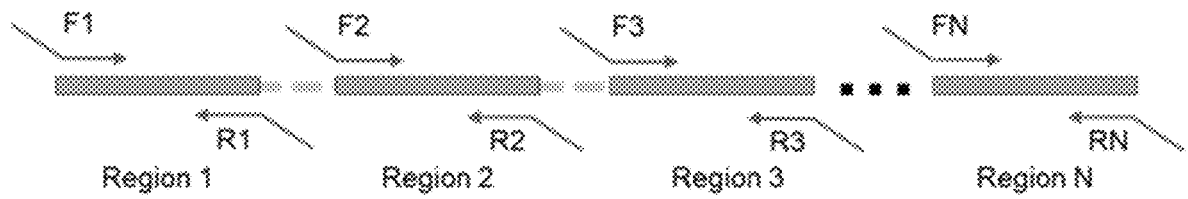
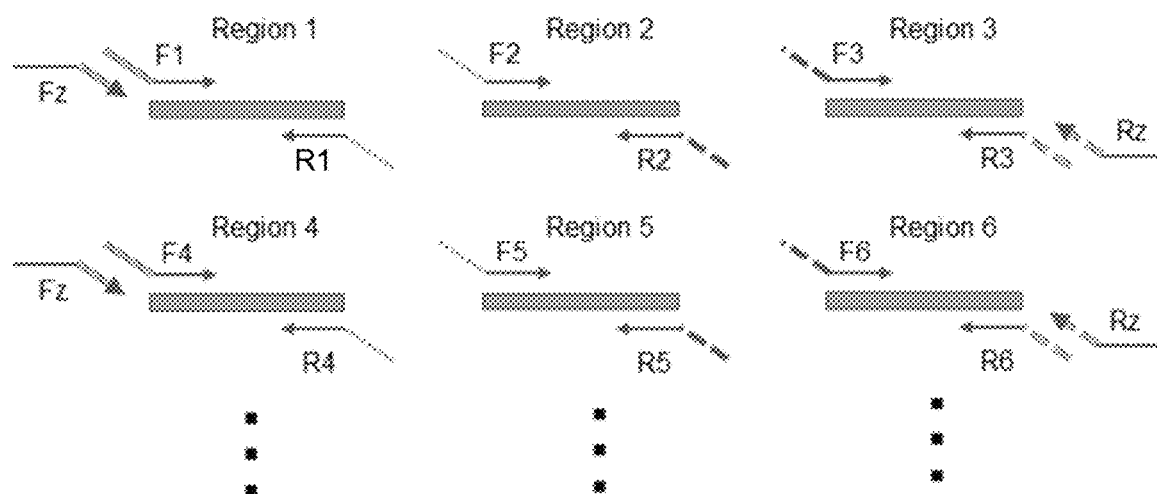
*FIG. 15A*
*FIG. 15B*
*FIG. 15C*

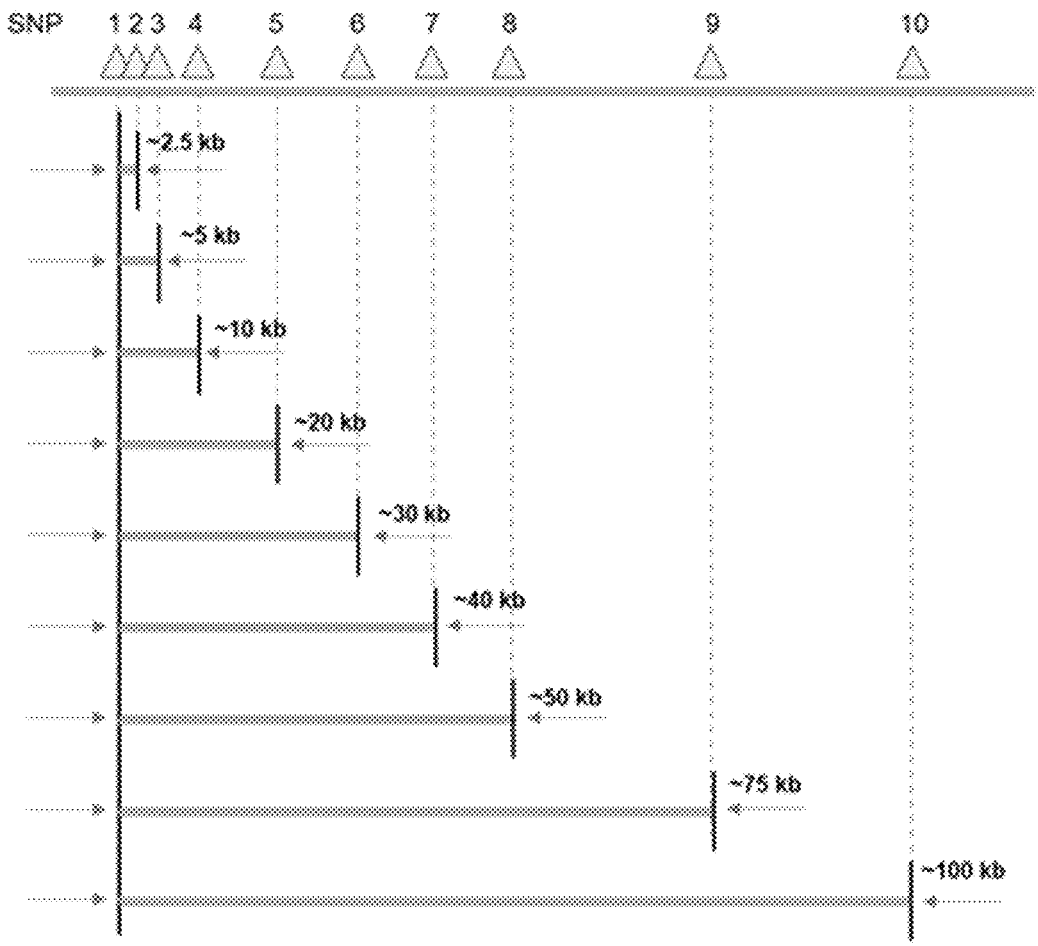
FIG. 17A
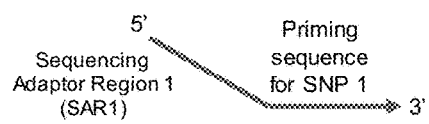
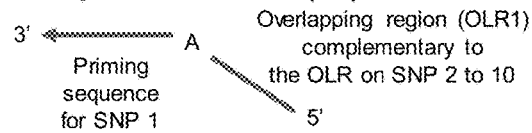
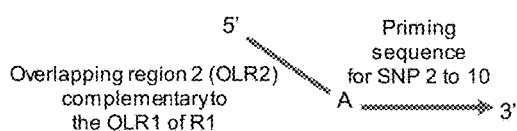
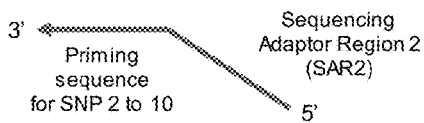
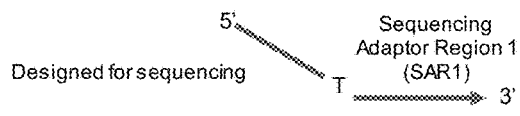
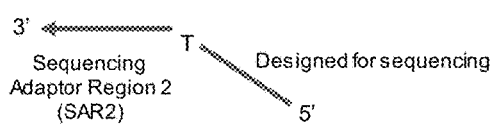
FIG. 17B

| SNP ID | Coordinate on Chr11 | Distance from the first SNP (kb) | Genotype | Forward primer (5' to 3') | Reverse primer (5' to 3') |
|---|---|---|---|---|---|
| rs11036868 | 5331270 | - | T / C | AATCGGGAAGCTGAAGGCC AAGGACTGTAGAGACATAG ATGA | CACTACCGTCGGATGACATA CTGGAGAGATTTCATCCTTG GAG |
| rs78930059 | 5333450 | 2.18 | G / T | ▓▓▓▓▓▓▓▓▓▓▓▓▓▓▓A GCAATGACAGAGTTTGACAT ATTGATT | GTGCTCTTCCGATCTGTTAG TGATCAATGTGTTAATCATA AAGTAATT |
| rs10768807 | 5336582 | 5.31 | T / A | ▓▓▓▓▓▓▓▓▓▓▓▓▓▓▓A CCTTCCTCCATAATCACATC TGCTA | GTGCTCTTCCGATCTCTGTTG CACCAACCTAATATAAGGAA |
| rs4910551 | 5343046 | 11.78 | G / A | ▓▓▓▓▓▓▓▓▓▓▓▓▓▓▓A GGAGTGACAATACAGAAAA AAATAGAGG | GTGCTCTTCCGATCTGAGGG GATTTGTATCCGTTGTTC |
| rs10837882 | 5351633 | 20.36 | T / A | ▓▓▓▓▓▓▓▓▓▓▓▓▓▓▓A CCTACATCTCCATACTTCTTG GCAAT | GTGCTCTTCCGATCTATGAT CATTCCTGATGAGAAAGAGA AG |
| rs2736557 | 5361361 | 30.09 | G / T | ▓▓▓▓▓▓▓▓▓▓▓▓▓▓▓A GGAGAGAGGAGTGGGCCGT A | GTGCTCTTCCGATCTAAAGA AAATTAGTTTCAGAAACTCC TCC |
| rs884222 | 5371742 | 40.47 | A / T | ▓▓▓▓▓▓▓▓▓▓▓▓▓▓▓A TATCCATCAATACAACACCT TCCATAG | GTGCTCTTCCGATCTACAGT AGATGTTAGATGCCCTTACA CA |
| rs2736543 | 5381334 | 50.06 | A / G | ▓▓▓▓▓▓▓▓▓▓▓▓▓▓▓A TACCTTAAAGGTTAAGGCCT GAATG | GTGCTCTTCCGATCTGGGGA AGGTGAAGTATCAACACA |
| rs4910781 | 5406896 | 75.63 | A / C | ▓▓▓▓▓▓▓▓▓▓▓▓▓▓▓A AGCAAACTCAGAGGGTTGG AGTAC | GTGCTCTTCCGATCTTATTTT TGTAGCTCTGACAGTTGTCT CC |
| rs10838096 | 5431296 | 100.03 | A / G | ▓▓▓▓▓▓▓▓▓▓▓▓▓▓▓A CCCTGACTCCATGCAGGAGA | GTGCTCTTCCGATCTGTTGA CTTTGATGGCTGCCTG |

*FIG. 18*

| SNP pairing | Hap I: C allele at SNP 1 (Reference: 5'-CTAATTTAAG-3') | | Hap II: T allele at SNP 1 (Reference: 5'-TGTGAGAGCA-3') | |
|---|---|---|---|---|
| | Alleles combination (frequency) | Determined Hap I | Alleles combination (frequency) | Determined Hap II |
| SNP 1—SNP 2 | C—T (80.5%)<br>C—G (19.5%) | CT-------- | T—G (84.7%)<br>T--T (15.3%) | TG-------- |
| SNP 1—SNP 3 | C—A (89%)<br>C—T (11%) | C-A------- | T—T (85.5%)<br>T—A (14.5%) | T-T------- |
| SNP 1—SNP 4 | C—A (81.3%)<br>C—G (18.7%) | C--A------ | T—G (83.1%)<br>T—A (16.9%) | T--G------ |
| SNP 1—SNP 5 | C—T (67.8%)<br>C—A (32.2%) | C---T----- | T—A (90.3%)<br>T—T (9.7%) | T---A----- |
| SNP 1—SNP 6 | C—T (80.2%)<br>C—G (19.8%) | C----T---- | T—G (86.4%)<br>T—T (13.6%) | T----G---- |
| SNP 1—SNP 7 | C—T (67.2%)<br>C—A (32.8%) | C-----T--- | T--A (65.2%)<br>T—T (34.8%) | T-----A--- |
| SNP 1—SNP 8 | C—A (68.6%)<br>C—G (31.4%) | C------A-- | T—G (61.7%)<br>T—A (38.3%) | T------G-- |
| SNP 1—SNP 9 | C—A (65.8%)<br>C—C (34.2%) | C-------A- | T—A (53%)<br>T—C (47%) | T-------x- |
| SNP 1—SNP 10 | C—G (58.1%)<br>C—A (41.9%) | C--------x | T—A (50.4%)<br>T—G (49.6%) | T--------x |

*FIG. 19*

| Region No. | SNP ID | Coordinate on chr11 | Forward primer (5' to 3') | Reverse primer (5' to 3') |
|---|---|---|---|---|
| 1 | rs7930833 | 5222527 | AATCGGGAAGCTGAAGCTTGATAGTTTCTACTTTGGGTTGATAATT | CACTACCGTCGGATGACATAATGGGAAGACATGTATATAATCTTAGAGATA |
| 2 | rs12364872 | 5222914 | [shaded]AGCAGAAAGAGATAATATTAAGGATAATCAG | GTGCTCTTCCGATCTGCAGAAAGAGATAATATTAAGGATAATCAG |
| 3 | rs10837628 | 5223174 | [shaded]AGTCAAATGGATATTTGTATCTGAAAAATC | GTGCTCTTCCGATCTATGCATCTTGATGATTAGAATTGCA |
| 4 | rs2187610 | 5224176 | AATCGGGAAGCTGAAGTCATGGTTCACCTTTCATTTGTTC | CACTACCGTCGGATGACATAACATCAAACTAAAAAATTTCCACACAA |
| 5 | rs10768682 | 5224277 | [shaded]ACAAATTCAAAAAACGGCTGCA | GTGCTCTTCCGATCTAAGAAATCAAAAGAAGAAAATTCTAATATTCA |
| 6 | rs10837630 | 5224812 | AATCGGGAAGCTGAAGGTAATAAGACAGTAGTGAATATCAAGCTACAAA | CACTACCGTCGGATGACATAAGTTAGGACTGAGAAGAATTTGAAAGG |
| 7 | rs10837631 | 5225126 | [shaded]AGTATCTCTAAGCAAGAGAACTGAGTGG | GTGCTCTTCCGATCTATTTGCTTATCCTGCATCTCTCAG |
| 8 | rs7110263 | 5225282 | AATCGGGAAGCTGAAGTTTTCTGAGGGATGAATAAGGCAT | CACTACCGTCGGATGACATAATTGGCAACAGCCCTGAT |
| 9 | rs1609812 | 5225911 | [shaded]ATACAATTTATATGCAGAAATATTTATATGCAG | GTGCTCTTCCGATCTATTTCTGGGTTAAGGCAATAGCAA |
| 10 | rs7480526 | 5226503 | AATCGGGAAGCTGAAGTTCCCATTCTAAACTGTACCCTGTT | CACTACCGTCGGATGACATAATGGTTAAGTTCATGTCATAGGAAGG |
| 11 | rs10768683 | 5226561 | AATCGGGAAGCTGAAGCCTATGACATGAACTTAACCATAGAAA | CACTACCGTCGGATGACATATGAGAACTTCAGGGTGAGTCTATG |
| 12 | rs10742583 | 5227411 | [shaded]ATTCCCAATTTTCTTATTACACAAATAAGA | GTGCTCTTCCGATCTAAACTCTTCCACTTTTAGTGCATCAA |
| 13 | rs11036364 | 5227774 | AATCGGGAAGCTGAAGTTAGTTACTTATTAGGTTTTGGGAAACAAG | CACTACCGTCGGATGACATAATTTTTGACTGCATTAAGAGGTCTCTAGT |
| 14 | rs7936823 | 5228938 | [shaded]AGAAAAGACGTCTTAAAATATTTTAAATGTT | GTGCTCTTCCGATCTAAAATCTAACAGCCAAGTCAAATCTG |
| 15 | rs3813727 | 5234682 | AATCGGGAAGCTGAAGCTGTCATGTGTGTCTTGACTCAGAA | CACTACCGTCGGATGACATAAGATGCGGTGGGAGATATG |
| 16 | rs10837643 | 5236808 | [shaded]AAAGGCCATGAGGACTGTTATTTG | GTGCTCTTCCGATCTAGCCAAGTCTTTGGAATTAACAGAC |
| 17 | rs4283007 | 5237260 | AATCGGGAAGCTGAAGCCGCATCCAGCCAGGATA | CACTACCGTCGGATGACATAACAAGAGTAGATGCTATTCTTCCACTTT |
| 18 | rs4402323 | 5237362 | [shaded]ATAGATAGGGACAAATTGAAGCAGAA | GTGCTCTTCCGATCTCATTTCCCTACCTCTAATCAACAGTT |
| 19 | rs4910736 | 5237759 | [shaded]AGAAGTATGAAGTAAGACATAGTCCCCAA | GTGCTCTTCCGATCTATTAAAATCGATACTGAGTTCTAAAATCATC |
| 20 | rs2105819 | 5238497 | AATCGGGAAGCTGAAGGCTCTCCACAATTCTAATCTCAGTTC | CACTACCGTCGGATGACATAATTGATAAGATAATATGAAAACACAGAATTCA |

*FIG. 20*

| | SNP No. | 1 | 2 | 3 | 4 | 5 | 6 | 7 | 8 | 9 | 10 | 11 | 12 | 13 | 14 | 15 | 16 | 17 | 18 | 19 | 20 |
|---|---|---|---|---|---|---|---|---|---|---|---|---|---|---|---|---|---|---|---|---|---|
| \multicolumn{22}{c}{Family 1} |
| Father | Hap I* | C | A | C | A | C | T | G | A | C | A | G | G | A | T | A | C | G | A | G | C |
| Father | Hap II | C | G | G | A | C | A | G | A | A | A | G | A | A | T | A | C | A | G | T |
| Mother | Hap I | C | G | G | A | C | A | G | A | A | A | A | G | A | T | A | C | A | G | T |
| Mother | Hap II* | G | A | G | G | G | T | T | G | A | G | A | G | A | T | A | C | G | A | C | C |
| Fetus | Hap from father | C | A | C | A | C | T | G | A | C | A | G | G | A | T | A | C | G | A | G | C |
| Fetus | Hap from mother | G | A | G | G | G | T | T | G | A | G | A | G | A | T | A | C | G | A | C | C |
| \multicolumn{22}{c}{Family 2} |
| Father | Hap I | G | A | G | G | G | T | T | G | A | G | A | G | A | T | A | C | G | A | C | T |
| Father | Hap II* | G | A | G | G | G | T | T | G | A | G | A | G | A | T | A | C | G | A | C | C |
| Mother | Hap I* | C | G | G | A | C | A | G | A | A | A | G | G | A | T | A | C | G | A | G | C |
| Mother | Hap II | G | A | G | G | G | T | T | G | A | G | A | G | A | T | A | C | A | C | T | |
| Fetus | Hap from Father | G | A | G | G | G | T | T | G | A | G | A | G | A | T | A | C | G | A | C | C |
| Fetus | Hap from Mother | C | G | G | A | C | A | G | A | A | A | G | G | A | T | A | C | G | A | G | C |
| \multicolumn{22}{c}{Family 3} |
| Father | Hap I | C | A | C | A | C | T | G | A | C | A | G | A | T | A | C | A | G | T | | |
| Father | Hap II* | C | A | G | A | C | T | G | A | C | A | G | G | A | T | A | C | G | A | G | C |
| Mother | Hap I | C | A | C | A | C | T | G | A | C | A | G | G | A | T | A | C | G | A | G | C |
| Mother | Hap II* | G | A | G | G | G | T | T | G | A | G | G | G | A | T | A | C | G | A | C | C |
| Fetus | Hap from Father | C | A | G | A | C | T | G | A | C | A | G | G | A | T | A | C | G | A | G | C |
| Fetus | Hap from Mother | G | A | G | G | G | T | T | G | A | G | G | G | A | T | A | C | G | A | C | C |
| \multicolumn{22}{c}{Family 4} |
| Father | Hap I* | G | A | G | G | G | T | T | G | A | G | A | A | G | A | T | A | C | A | C | T |
| Father | Hap II* | G | A | G | G | G | T | T | G | A | G | A | A | G | A | T | A | C | A | C | T |
| Mother | Hap I* | C | G | G | A | C | A | G | A | A | A | A | G | A | T | A | C | A | G | T | |
| Mother | Hap II | G | A | G | G | T | T | A | G | A | A | T | A | C | G | A | C | C | | | |
| Fetus | Hap from father | G | A | G | G | G | T | T | G | A | G | A | A | G | A | T | A | C | A | C | T |
| Fetus | Hap from mother | C | G | G | A | C | A | G | A | A | A | A | G | A | T | A | C | A | G | T | |

*FIG. 22*

PRIMERS AND ASSAYS FOR LINKING REGIONS USING POLYMERASES

CROSS-REFERENCES TO RELATED APPLICATIONS

The present application claims priority to and is a non-provisional of U.S. Provisional Application No. 62/846,149, entitled "PRIMERS AND ASSAYS FOR LINKING REGIONS USING POLYMERASES," filed on May 10, 2019, the disclosure of which is incorporated by reference in its entirety for all purposes.

REFERENCE TO A "SEQUENCE LISTING" SUBMITTED AS ASCII TEXT FILES VIA EFS-WEB

The instant application contains a Sequence Listing which has been filed electronically in ASCII format and is hereby incorporated by reference in its entirety. Said ASCII copy, created on Jul. 27, 2020, is named 080015-026510US-1190118_SL.txt and is 16,592 bytes in size.

BACKGROUND

Humans have two copies of each chromosome, one from each of the parents. Understanding of the combination of variants on the same parental chromosome, i.e., the haplotype, can provide valuable clinical implications. In particular, the haplotype information is useful for noninvasive prenatal testing of monogenic diseases and deciphering the genomic inheritance of the fetus (Hui et al. Clin Chem. 2017; 63:513-524; Lo et al. Sci Transl Med. 2010; 2:61ra91). However, current techniques for determining haplotypes of a particular individual can be costly, have low accuracy, and provide low throughput.

BRIEF SUMMARY

PCR assays using high throughput polymerases can be used to link distant regions (e.g., separated by 100 bp to 100 kbp) of a same large DNA molecule into a smaller DNA molecule, e.g., so a haplotype of the two regions can more easily be measured. The high throughput polymerases can add an extra nucleotide to only one end of each strand of a double stranded DNA (e.g., an A at the 3' end). This may preclude or cause a low yield for generating the smaller, linked DNA molecules (also referred to as extended amplicons).

To address these problems, particular forward and reverse primers can be used. For example, a reverse primer R1 can have a first portion complementary to an ending sequence of region A and can have a second portion having an overlapping sequence. A forward primer F2 can have a first portion complementary to a starting sequence of region B, where the forward primer includes a complementary overlapping sequence (e.g., the same first portion or a second portion) that is complementary to the overlapping sequence. The first portion of F2 may be the entire primer.

A better understanding of the nature and advantages of embodiments of the present disclosure may be gained with reference to the following detailed description and the accompanying drawings.

Terms

The term "fragment" (e.g., a DNA fragment), as used herein, can refer to a portion of a polynucleotide or polypeptide sequence that comprises at least 3 consecutive nucleotides. A nucleic acid fragment can retain the biological activity and/or some characteristics of the parent polypeptide. A nucleic acid fragment can be double-stranded or single-stranded, methylated or unmethylated, intact or nicked, complexed or not complexed with other macromolecules, e.g. lipid particles, proteins. A fragment can be derived from a particular tissue type, e.g., fetal, tumor, a transplanted organ, etc.

The term "assay" generally refers to a technique for determining a property of a nucleic acid. An assay (e.g., a first assay or a second assay) generally refers to a technique for determining the quantity of nucleic acids in a sample, genomic identity of nucleic acids in a sample, the copy number variation of nucleic acids in a sample, the methylation status of nucleic acids in a sample, the fragment size distribution of nucleic acids in a sample, the mutational status of nucleic acids in a sample, or the fragmentation pattern of nucleic acids in a sample. Any assay known to a person having ordinary skill in the art may be used to detect any of the properties of nucleic acids mentioned herein. An assay can also refer to a technique for joining the amplification products from different regions of a DNA molecule to form one or more DNA molecules. Properties of nucleic acids include a sequence, quantity, genomic identity, copy number, a methylation state at one or more nucleotide positions, a size of the nucleic acid, a mutation in the nucleic acid at one or more nucleotide positions, and the pattern of fragmentation of a nucleic acid (e.g., the nucleotide position(s) at which a nucleic acid fragments). The term "assay" may be used interchangeably with the term "method". An assay or method can have a particular sensitivity and/or specificity, and their relative usefulness as a diagnostic tool can be measured using ROC-AUC statistics.

A "sequence read" refers to a string of nucleotides sequenced from any part or all of a nucleic acid molecule. For example, a sequence read may be the entire nucleic acid fragment that exists in the biological sample. Also as an example, a sequence read may be a short string of nucleotides (e.g., 20-150 bases) sequenced from a nucleic acid fragment, a short string of nucleotides at one or both ends of a nucleic acid fragment, or the sequencing of the entire nucleic acid fragment that exists in the biological sample. Paired sequence reads can be aligned to a reference genome, which can provide a length of the fragment. A sequence read may be obtained in a variety of ways, e.g., using sequencing techniques or using probes, e.g., in hybridization arrays or capture probes, or amplification techniques, such as the polymerase chain reaction (PCR) or linear amplification using a single primer or isothermal amplification, or based on biophysical measurements, such as mass spectrometry. A sequence read may be obtained from a single-molecule sequencing. "Single-molecule sequencing" refers to sequencing of a single template DNA molecule to obtain a sequence read without the need to interpret base sequence information from clonal copies of a template DNA molecule. The single-molecule sequencing may sequence the entire molecule or only part of the DNA molecule. A majority of the DNA molecule may be sequenced, e.g., greater than 50%, 55%, 60%, 65%, 70%, 75%, 80%, 85%, 90%, 95%, or 99%.

A "separation value" (or relative abundance) corresponds to a difference or a ratio involving two values, e.g., two amounts of reads having two different alleles. The separation value could be a simple difference or ratio. As examples, a direct ratio of x/y is a separation value, as well as x/(x+y). The separation value can include other factors, e.g., multiplicative factors. As other examples, a difference or ratio of functions of the values can be used, e.g., a difference or ratio of the natural logarithms (ln) of the two values. A separation value can include a difference and/or a ratio.

The term "classification" as used herein refers to any number(s) or other characters(s) that are associated with a particular property of a sample. For example, a "+" symbol (or the word "positive") could signify that a sample is classified as having deletions or amplifications. The classification can be binary (e.g., positive or negative) or have more levels of classification (e.g., a scale from 1 to 10 or 0 to 1).

The terms "cutoff" and "threshold" refer to predetermined numbers used in an operation. For example, a cutoff size can refer to a size above which fragments are excluded. A threshold value may be a value above or below which a particular classification applies, e.g., a classification of a condition, such as whether a subject has a condition or a severity of the condition. A cutoff or threshold may be "a reference value" or derived from a reference value that is representative of a particular classification or discriminates between two or more classifications, e.g., which distinguishing between which alleles comprise a haplotype. Such a reference value can be determined in various ways, e.g., chosen after and based on output of the test data, as will be appreciated by the skilled person. For example, metrics can be determined for two different cohorts of subjects with different known classifications, and a reference value can be selected as representative of one classification (e.g., a mean) or a value that is between two clusters of the metrics. Accordingly, reference subjects with known classifications of haplotypes can be used to determine reference levels to discriminate between the different haplotypes. As another example, a reference value can be determined based on statistical simulations of samples. Any of these terms can be used in any of these contexts. As will be appreciated by one of skilled in the art, a cutoff can be selected to achieve a desired sensitivity and specificity.

BRIEF DESCRIPTION OF THE DRAWINGS

FIGS. 1A-1D show a four-primer PCR system used to amplify two different target regions A and B.

FIGS. 8A-8B illustrate a fusion-PCR method for linking more than two regions where only certain regions link to each other according to embodiments of the present disclosure

FIGS. 15A-15C show forming fused products of three regions, with one region from each of three groups according to embodiments of the present disclosure.

FIGS. 17A-17B show (A) lengths between different SNPs in a DNA molecule and (B) configurations of the primers for the SNPs according to embodiments of the present disclosure.

FIG. 18 is a table showing the sequences of primers for amplifying each region according to embodiments of the present disclosure. Figure discloses SEQ ID NOS 11-30, respectively, in order of appearance.

FIG. 19 is a table showing the phases determined by the digital fusion PCR method according to embodiments of the present disclosure. Figure discloses "CTAATTTAAG" as SEQ ID NO: 31 and "TGTGAGAGCA" as SEQ ID NO: 32.

FIG. 20 is a table showing primer sequences for SNPs in the HBB gene according to embodiments of the present disclosure. Figure discloses SEQ ID NOS 33-72, respectively, in order of appearance.

FIG. 22 is a table showing haplotypes deduced by fusion PCR method for family trios according to embodiments of the present disclosure.

DETAILED DESCRIPTION

Figure 2A:
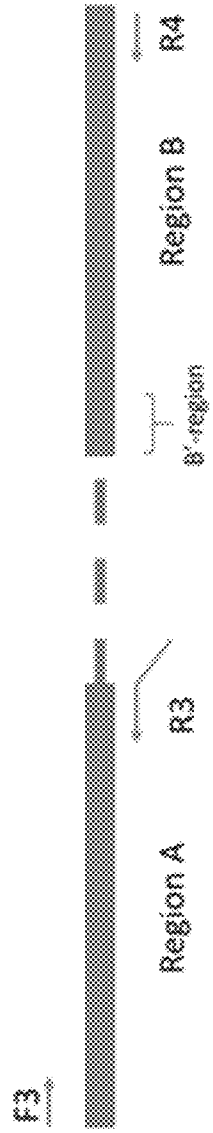
FIGS. 2A-2C show a three-primer PCR system used to amplify two different target regions A and B.

Sequencing multiple distant regions of a DNA molecule may be beneficial. Only certain regions (e.g., a single nucleotide polymorphism [SNP]) of the DNA molecule may be of interest. Certain sequencing techniques may be limited in the length that can be sequenced at one time. Sequencing intermediate regions between regions of interest may needlessly consume equipment and operator time. Conventional methods that link together two separate regions for sequencing suffer from a number of problems. Controlling the purity of the DNA molecules to be amplified can be difficult. Such conventional methods may be inaccurate. The techniques described herein allow for accurate and efficient methods to link together two or more separate regions of a DNA molecule. The resulting fused DNA molecules can then be sequenced and/or haplotyped.

Some embodiments can provide increased yield and corresponding efficiency by accounting for the use of high throughput polymerases having a bias for adding a particular nucleotide (e.g., A) at an overhang position. In one example, such a technique can include designing a reverse primer that hybridizes at a location with a complementary nucleotide (e.g., T) at an end so that the two regions can be properly linked. The other region to be linked can have the particular nucleotide after a forward primer, thereby creating a matching overlap region to link the regions. In another example, the primers themselves can include an overlap region with the particular nucleotide (and complementary nucleotide for certain primers in certain embodiments) inserted between two portions. Accordingly, forward primers with portions that are complementary to portions of reverse primers may be used to link separate regions.

As other examples with or without use of such high throughput polymerases having a bias, different combinations of regions from the same molecule may be linked together in groups. This combination of regions could allow an accurate and cost-effective haplotyping of a large genomic regions which covers multiple regions of interest. Forward and reverse primers may be used to amplify the fused product. Three or more regions may be linked together. The simultaneous fusion, phasing and haplotyping of a larger number of regions would be of advantage when one or more of the regions are homozygous because the homozygous regions cannot provide information for the haplotype. Further, kits including such specially designed primers may be provided. Details of these features are described below.

I. Haplotype Techniques

A number of methods have been available for determining the haplotypes of an individual. These methods are broadly divided into two categories, namely computational deduction and experimental analysis. However, existing methods for determining the haplotypes of an individual have their own limitations including relatively low accuracy, high cost, low-throughput, and incapability of targeting a specific region. In this application, we describe techniques that can accurately determine the haplotypes of an individual at a relatively low cost and in a high-throughput manner.

A. Computations Approaches

Computational approaches are frequently used to statistically infer the haplotypes of an individual based on the information of the genotypes of a relevant population (Browning et al., Nature Reviews Genetics, 2011; 12:703-714). Through the analysis of genotypes of a large number of individuals in a population, the common haplotypes of the population can be determined. For a tested individual, the genotypes would be worked out experimentally and would be compared with the known haplotypes of the population to infer the most likely haplotypes of individual.

However, the accuracy of such computational methods are affected by the ethnicity and the ancestral background of the tested individual. In regions with a wide ethnicity mix, computational haplotyping methods may not be able to provide sufficient accuracy for clinical purposes. In addition, the accuracy of this approach would be reduced when resolving haplotypes over a long distance and in regions with low linkage disequilibrium. For example, in the genomic regions encoding the human leukocyte antigen (HLA), recombination would frequently occur.

Therefore, the computational inference of haplotype within these regions with high recombination has low accuracy.

B. Experimental Analysis

Alternatively, the haplotypes of an individual can be determined experimentally. The principle of these experimental haplotyping methods is based on genotyping different regions of a single long DNA molecule. There are three common approaches for achieving this purpose, including (a) crosslinking of structurally proximal regions, (b) compartmentalization, and (c) long-read sequencing.

1. Crosslinking

Crosslinking makes use of the fact that a chromosome would fold into a 3-dimensional (3-D) structure and the different parts of the same chromosome would have a much higher chance of coming into proximity. Through crosslinking DNA that come within close proximity in the 3-D space, DNA regions originating from the same chromosome, but separated by up to a few kilobases, can be connected. The sequences of these hybrid molecules can be used to phase the single nucleotide polymorphisms (SNP) alleles. Examples of this approach include the Hi-C technique (Selvaraj et al. Nat. Biotechnol 2013; 31:1111-8) and a modified Hi-C technique "Chicago" (Putnam et al. Genome Res. 2016; 26:342-50).

2. Compartmentalization

The compartmentalization approach can take advantage of automated platforms for the compartmentalization. The principle of this approach is to separate individual long DNA molecules obtained from a tested subject into different compartments. Then, the DNA from a single compartment would be genotyped. As the genotype information is obtained from a single DNA molecule rather than the one pair of the two parental chromosomes, the obtained allelic information would represent a haplotype. Separation of individual long DNA molecules in compartments can be performed manually (Peters et al. Nature 2012; 478:190-5) or using microfluidic systems (Zheng et al. Nat. Biotechnol 2016:34:303-11).

To improve the cost-effectiveness of this approach, a long DNA molecule inside a single compartment would be fragmented into smaller fragments. Each short fragment arising from the same long DNA molecules would be encoded with the same index. Then, short DNA fragments from different compartments can be pooled together and be sequenced using massively parallel sequencing. Fragments with the same index can be used to construct a haplotype (Amini et al. Nat. Genet 2014; 46:1343-9). Examples of automated platforms allowing indexing of fragments include but not limited to the Chromium system from 10× genomics and the phased sequencing solutions from Illumina.

However, existing methods for haplotyping based on these approaches are mainly designed for haplotyping relatively large genomic regions. Using these methods for haplotyping a relatively short genomic region would require enrichment of the relevant region, e.g., by hybridization capture, making it relatively expensive and labor-intensive.

3. Long-Read Sequencing

In another approach, a whole long DNA molecule can be sequenced directly to determine its sequence. This can be performed by the newer generation of sequencing platforms, for example but not limited to using the single molecule, real-time sequencing technology (by Pacific Biosystems) and the nanopore sequencing technology (by Oxford Nanopore Technologies). However, this systems also require prior enrichment of regions of interest for sequencing.

II. Compartmentalization Using PCR

DNA molecules can be compartmentalized into emulsion droplets. Each emulsion droplet can include DNA molecules having two regions that can be linked together via amplification. Linking together two regions can allow for more efficient sequencing and haplotyping. Four-primer and three-primer systems have been used for the amplification.

A. Four-Primer System

For haplotyping a specific region, a number of PCR-based methods have been described. For example, Wetmur et al. developed the linking emulsion PCR method (Wetmur et al. Nucleic acids research 2005; 33:2615-9). In this method, diluted DNA templates are distributed in emulsion droplets, which acts as compartments.

FIGS. 1A-1D shows a four-primer PCR system used to amplify two different target regions A and B. FIG. 1A shows Region A and Region B as the two targets which require phasing. Forward primer F1 and reverse primer R1 are for amplifying Region A. Forward primer F2 and reverse primer R2 are for amplifying Region B. The dotted line 105 represents the genomic intermediate region between Region A and Region B. The two regions can be separated by a few kilobases and it is not drawn according to scale.

In FIG. 1B, forward primer F2 and reverse primer R1 are partially complementary. In this example, there are 32 complementary nucleotides between F2 and R1, with 10 nt for each primer being specific to the respective region. The complementary region is denoted as overlapping region (OLR) 110. A biotin molecule 115 was linked to the 5' end of F2 and R1, e.g., to allow removal of non-linked strands, as mentioned below.

In FIG. 1C, the 3'-end of the PCR amplified products for Region A and Region B contains the OLR 110 so that they would be complementary to each other. Therefore, the 3' end of the amplified products for Region A can be used as a primer on the amplified products from Region B and vice versa. This would lead to the linking of the two amplified regions. The linked DNA strands can then be extended to the right in the top strand and to the left in the lower strand, thereby generating a relatively short molecule that includes the distant regions A and B.

Accordingly, as illustrated in FIG. 1B, there are 32 nucleotide overlapping between the reverse primer for amplicon A and the forward primer for amplicon B. This overlapping allows the linking of the two amplicons. When the concentration of DNA template is low and there is only one DNA template within each emulsion droplet, the linked PCR products would represent a haplotype of the individual.

However, in this system, the linking of the two amplicons would not be complete (i.e., not all linked), and unlinked DNA molecules from each region would be present. For example, the single-stranded DNA molecules resulted from the extension of R1 or F2 would only cover Region A or Region B, respectively. These unlinked DNA molecules would affect the subsequent haplotyping analysis. Therefore, these unlinked DNA molecules need to be removed through the binding of biotinated PCR primers and the capping of unextended single stranded DNA.

In FIG. 1D, the unlinked PCR products would contain the biotin-linked primers R1 and F2. They can be removed by treatment with strepavidine beads.

B. Three Primer System

In another method described by Tyson et al., a three-primer PCR amplification system was combined by emulsion droplet partition to haplotype a structurally complex region (Tyson et al. BMC Genomics 2012; 13:693). Similar to the method described by Wetmur et al, the PCR system was set up in emulsions with target DNA at very low concentration so that each emulsion droplet contains a single long target DNA molecule. In contrast to the method described by Wetmur et al, the method developed by Tyson et al. only used 3 primers.

Figure 2B:
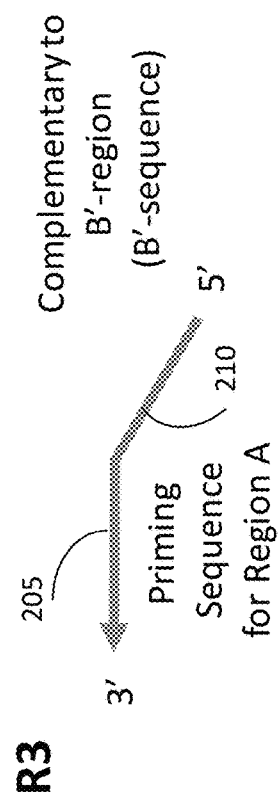
Figure 2C:
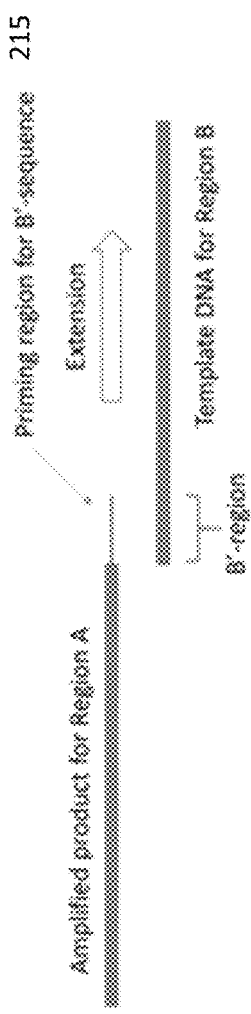

FIGS. 2A-2C show a three-primer PCR system used to amplify two different target regions A and B.

In FIG. 2A, forward primer F3 and reverse primer R3 are used for amplifying Region A.

In FIG. 2B, the reverse primer R3 consists of two parts. The 3' end 205 contains nucleotides complementary to the sequences of Region A so that it can serve as a primer for amplifying Region A. The 5' end 210 of R3 is complementary to the B'-region of Region B.

In FIG. 2C, after PCR amplification of Region A using F3 and R3, the amplified products would contain a 3' end 215 that is complementary to the B'-region. This amplified product can serve as a primer for amplifying Region B together with reverse primer R4. As a result, Regions A and B can be linked together. Each linked PCR product consists of a Region A and Region B of a single DNA molecule and represents a haplotype.

Based on the method described by Tyson et al., allele-specific PCR was used as a second round of amplification for the selection of linked molecules carrying a particular allele at Region A. The selection of the linked molecules can be performed by amplification using a forward primer that is specific to a particular allele in region A and a reverse primer at the end of region B. In this manner, only one of the haplotypes is amplified, where the amplified haplotype corresponds to the particular allele in region A. The selected molecules were sequenced using Sanger sequencing to determine the sequence at Region B so that the alleles at Region A and Region B can be phased.

C. Problems

In these PCR methods, manual production of droplet emulsion is used for the distribution of the very dilute concentration of long template DNA molecules into individual droplets. The emulsion is typically formed by shaking a mixture of oil and aqueous reagents used for the PCR reaction. However, the distribution of DNA molecules into individual droplets using this manual method suffers from a number of problems.

First, the volume of the droplets cannot be precisely controlled. As a result, there is a relatively high chance of having two or more DNA molecules partitioned into one large droplet. In such a situation, the phase of the alleles at the different loci would be wrongly determined. Moreover, the PCR reaction carried out at different droplets do not have a uniform efficiency. In these previous methods using emulsion PCR analysis, the linked products were then amplified using allele-specific PCR to amplify DNA molecules carrying one of the two alleles at the first locus (e.g. Region A). Sanger sequencing was then performed to determine the allele at the second locus (e.g. Region B) that was linked to a particular allele at the first locus.

III. Fusion-PCR Method

In this patent application, we describe robust haplotyping methods, which can make use of microfluidic systems for linking multiple targets on a single DNA molecule, with the linked molecules being sequenced by massively parallel sequencing. These methods can be particularly useful for haplotyping regions that involve variants that cannot be genotyped by simple allele-discrimination techniques, for example allele-specific PCR or allele-specific fluorescent probes. Some embodiments can utilize a microfluidic digital PCR system to generate tiny droplets, e.g., most of them containing no more than one long DNA molecule covering the region of interest. PCR amplification can be performed on two or more regions of interests from one long DNA molecule using a highly efficient polymerase, for example but not limited to, Taq polymerase and two sets of primers. Use of such polymerases can significantly increase the throughput by reducing the time to generate amplification products.

There are existing commercially available devices that can automatically generate thousands of nanoliter-sized droplets in a short time, for example but not limited to BioRad QX200 Droplet Generator, Elveflow Droplet Generator Pack, and Micronit Microfluidic Droplet Generator. Other methods for generation individual compartments for the PCR reaction can also be used, for example but not limited by microfluidics systems. Examples of such systems include Fluidigm BioMark system and the systems provided by Microfluidic Chipshop.

Although using such a polymerase increases efficiency and can provide uniformity in the droplets, such polymerases can cause problems by adding an additional [A] to the 3' end of the extended sequence. Such an addition would cause OLR 110 and end 210 to likely not be complementary. Embodiments can address such a problem while still being able to use the high efficiency polymerases.

A. Adding A in Reverse Primer: Sequence Content in Region A and B—Specific Genomic Positions Having A and T Regions to be linked can be selected to take advantage of the additional A at the 3' ends added by polymerases. A region with a T on the 5' end may be selected in order to complement the additional A added by polymerases.

FIGS. 3A-3F illustrate a fusion-PCR method using respective genomic positions having a T and an A according to embodiments of the present disclosure.

Figure 3A:
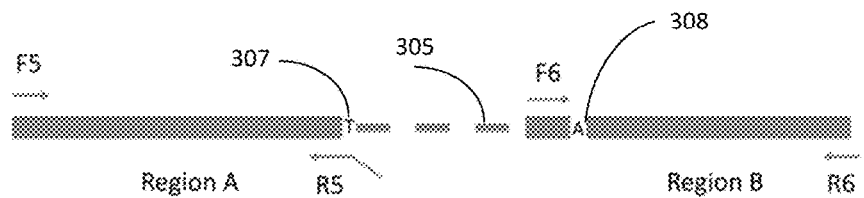
FIGS. 3A-3F illustrate a fusion-PCR method using respective genomic positions having a T and an A in regions A and B according to embodiments of the present disclosure.

In FIG. 3A, only the Watson strand of the long DNA molecule is shown. Forward primer F5 and reverse primer R5 are used for amplifying Region A. Forward primer F6 and reverse primer R6 are used for amplifying Region B. The 3' end 307 of Region A is designed to be a thymine. Region B is specially designed so that the nucleotide downstream (3') to the 3' end of the F6 primer is an adenosine 308. The dotted line between Regions A and B is a piece of long DNA, for example ranging from 100 bp to 100 kbp, that represents an intermediate region 305 between regions A and B.

Figure 3B:
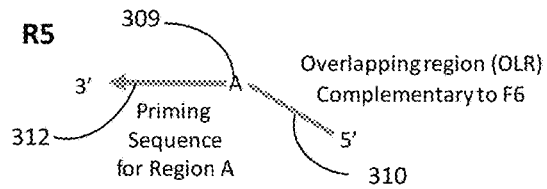

In FIG. 3B, for the reverse primer R5, an additional sequence 310 that is complementary to F6 is put at its 5' end. This region of the primer is named as the overlapping region (OLR). The 3' end of R5 would be used for carrying out the PCR amplification of Region A. An adenosine 309 separates OLR 310 from the priming sequence 312 for Region A. The adenosine 309 is complementary to thymine 307 in Region A.

Figure 3C:
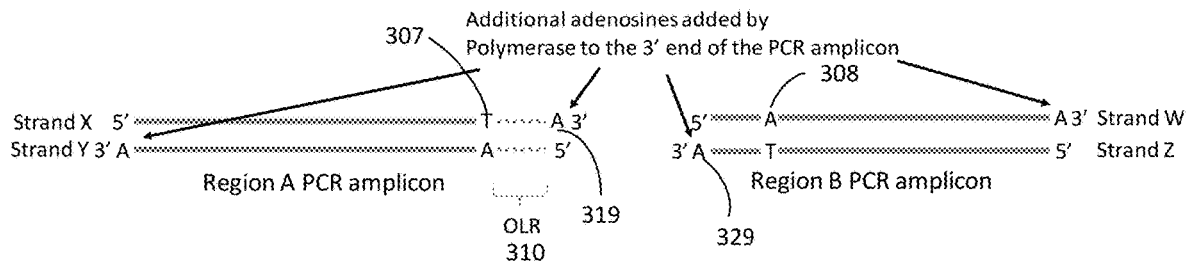

In FIG. 3C, after PCR amplification, additional adenosines [A] (e.g., 319 and 329) would be added to the 3' end of each of the four extended strands (i.e. Strands W, X, Y and Z) by the polymerase. Strands X and Y are the two strands of the PCR amplicons for Region A, and Strands W and Z are the two strands of the PCR amplicon for Region B. The additional adenosine 319 at the 3' end of Strand X can improve the efficiency and specificity of subsequent joining of the PCR amplicons of the Region A and Region B. Moreover, most of the existing commercially available microfluidic systems use polymerase that would add an additional [A] to the 3' end of the extended sequence.

On the other hand, as there would be an additional adenosine at each amplified strand of Region A, primer F6 needs to be specially designed so that the nucleotide downstream (3') to the 3' end of the F6 primer needs to be an adenosine 308 in FIGS. 3A and 3C. Similarly, the binding site on Region A for R5 to anneal would need to be a thymine [T] (307 as illustrated in FIG. 3A).

Figure 3D:
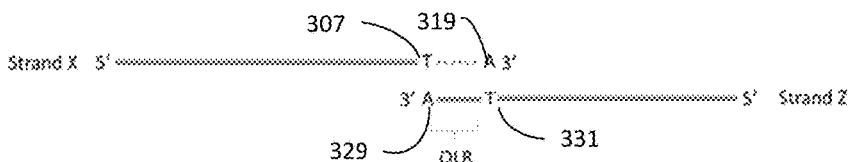

In FIG. 3D, Strand X and Strand Z would anneal to each other at the OLR. The thymine [T] 307 at the 5' end of the annealing site of R5 at Region A would bind with the adenosine [A] 329 at the 3' end of Strand Z. The thymine [T] 331 created by the adenosine 308 adjacent to 3' end of F6 would bind with the adenosine [A] 319 at the 3' end of Strand X. These two A-T bind sites would improve the efficiency and specificity of the linking of Strand X and Strand Z.

Figure 3E:
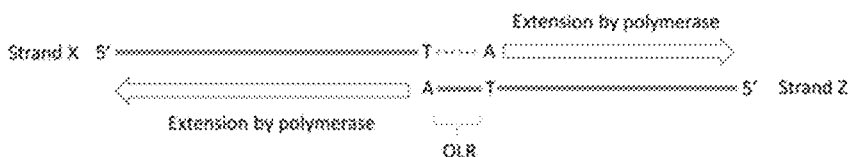

In FIG. 3E, after the priming, the Strands X and Z can be linked together with polymerase extension. That is, a polymerase can be used to extend the top strand to the right (3' direction), and the bottom strand can be extended to the left (5' direction).

Figure 3F:
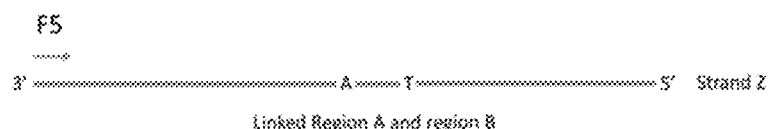

In FIG. 3F, within the reaction compartments, the concentrations of R5 and F6 can be lower than the concentrations of F5 and R6, e.g., so that after linking, the extended amplicon is amplified. Examples of the ratio between these groups of primers (R5& F6 vs F5&R6) include but not limited to 1:100000, 1:50000, 1:10000, 1:5000, 1:1000, 1:500, 1:200, 1:150, 1:100, 1:80, 1:60, 1:40, 1:30, 1:20, 1:10 and 1:5. The reason for having lower concentrations of R5 and F6 is to ensure that they would be exhausted after forming sufficient Strands X and Z so that there will not be excessive amount of Strands Y and W. Isolated Strands Y and W do not carry the haplotype information regarding Regions A and B. In addition, Strands Y and W may interact or fuse with amplified products of Region A and Region B from another compartment in downstream process. This could affect the accuracy of the haplotyping method. The higher concentrations of F5 and R6 would allow these two primers to carry out the final PCR amplification of the linked sequences. In other embodiments, a separate amplification procedure can be used to amplify the extended amplicons, or potentially not amplified at all, e.g., if single-molecule sequencing is used to analyze the extended amplicons.

After the extended amplicons are generated, they can be analyzed, e.g., using allele-specific PCR or sequencing.

In FIG. 3A, the 3' end 307 of Region A is designed to be a thymine, and the complementary primer part of R5 includes an A 309 at the end. This specific arrangement of an adenosine [A] 309 can be useful for the fusing of Region A and Region B. For the PCR amplification of Region B using F6 and R6, additional adenosine [A] 329 was added to the 3' end of Strand Z (FIG. 3C). The OLR 310 shares the same sequence with the OLR on Strand Z (FIG. 3D). To generate fusion products involving Region A and Region B, we need the sequences at the 3' ends of Strand X and Strand Z to be completely complementary (FIG. 3D). The design of an adenosine [A] 309 on R5 is to ensure that additional adenosine [A] 329 added to the 3' end of Strand Z would be complementary to the thymine [T] 307 on Strand X. Similarly, an additional adenosine [A] 319 is added to the 3' end of Strand X by the polymerase. The adenosine [A] 308 on Strand W is to ensure that the adenosine [A] 319 would be complementary to the thymine [T] 331 on Strand Z (FIG. 3D). This arrangement enables more complete amplification to obtain extended amplicons covering both regions, with greater efficiency.

B. Adding a in Reverse Primer: Non-Specific Genomic Positions

As described above in FIG. 3A, the 3' end 307 of Region A is designed to be a thymine, and the complementary primer part of R5 includes an A 309 at the end. But, in some embodiments, the complementary primer part can end just before the A, and A would be an additional base ($3^{rd}$ portion) between the complementary portion and the OLR portion. In this manner, the end of region A does not have to be a T. Instead, the additional A can cause a T to be added in the amplification.

Figure 4A:
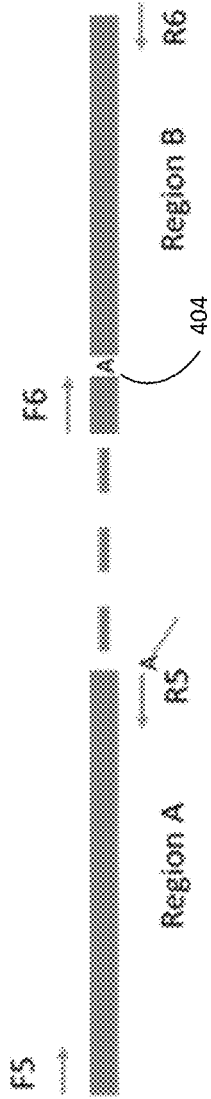
FIGS. 4A-4C illustrate a fusion-PCR method using a reverse primer with an added A according to embodiments of the present disclosure.
Figure 4B:
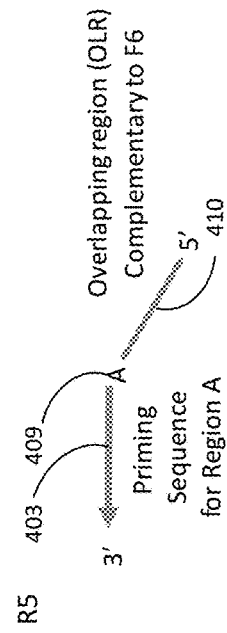
Figure 4C:
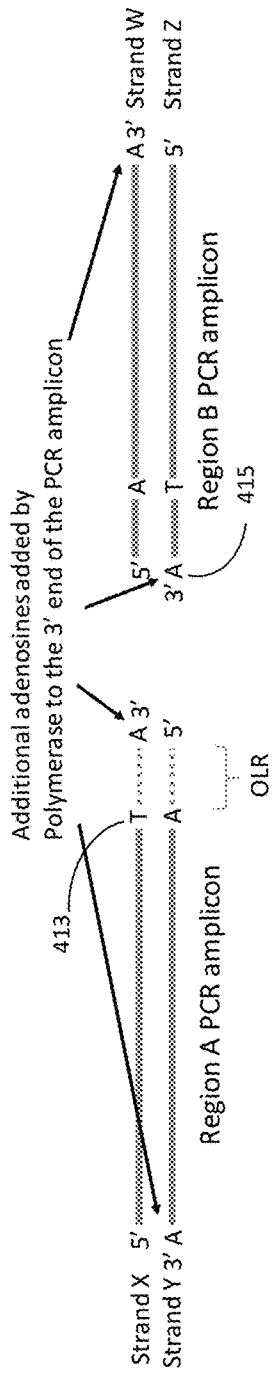

FIGS. 4A-4C illustrate a fusion-PCR method using a reverse primer with an added A according to embodiments of the present disclosure. FIG. 4A show a DNA molecule with Region A and Region B. Region A may not end with a thymine [T] on its 3' end, in contrast to Region A in FIG. 3A. Accordingly, in this alternative design in FIG. 4A, the annealing site for the 5' end of R5 does not need to be a thymine [T].

FIG. 4B shows reverse primer R5. An additional adenosine [A] 409 can be put between the priming sequence 403 for Region A and the OLR 410.

FIG. 4C shows the PCR amplicons formed by the primers. The additional [A] 409 can generate the [T] 413 on Strand X for [A] 415 at the 3' end of Strand Z to bind to. [A] 415 is an additional adenosine added by a polymerase to the 3' end of the amplicon.

The additional adenosine [A] in the reverse primer may allow for regions to be designed to end in any nucleotide on the 3' end. The region can be designed based on factors other than ending in a thymine [T]. For example, regions may be designed for a certain length or covering certain SNPs without consideration of whether a thymine is present at the end of the region.

C. Adding a in Reverse Primer and Forward Primer

In the scenario of FIG. 4A, region B still has the requirement of an A 404 after the OLR region. In some embodiments, an extra A can be added to both reverse primer R5 and forward primer F6.

FIGS. 5A-5D illustrate a fusion-PCR method using reverse and forward primers with an added A according to embodiments of the present disclosure. In this other alternative design, the 5' ends of each of R5 and F6 can be engineered to an artificial sequence.

Figure 5A:
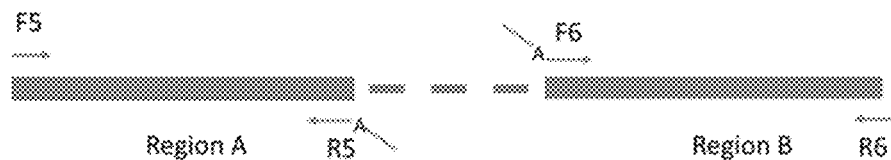
FIGS. 5A-5D illustrate a fusion-PCR method using reverse and forward primers with an added A according to embodiments of the present disclosure.
Figure 5B:
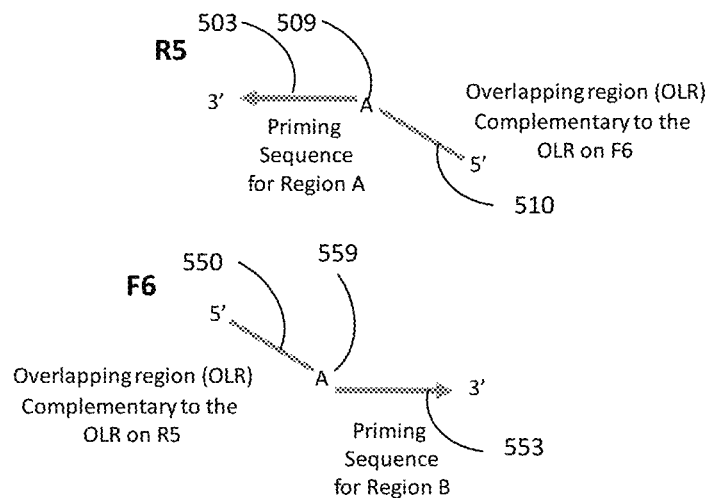

In FIG. 5B, the two artificial sequences would be complementary to each other. An extra adenosine [A] 509 can be put between the priming sequences 503 and the OLR 510, where the A is still part of the artificial sequences, but not part of the OLR.

Figure 5C:
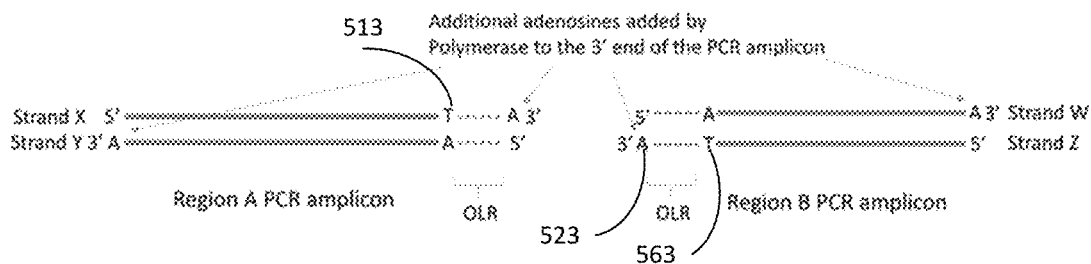

In FIG. 5C, the adenosine [A] 509 on R5 would generate a [T] 513 on Strand X locating between the OLR and the PCR amplicon. This [T] 513 would bind to the [A] 523 at the 3' end of Strand Z. The adenosine 559 on F6 would generate a [T] 563 between the OLR and the PCR amplicon on Strand Z. This [T] would be bind to the [A] at the 3' end of Strand X.

In this example, the OLR of the reverse primer is complementary to the OLR of the forward primer, so there is not sequence requirement for the regions, as the OLR is handled completely in the primers.

Figure 5D:

In FIG. 5D, the binding of Strand X and Strand Z at the OLR is shown. Each strand can be extended to form a double-stranded molecule with both strands of region A and both strands of region B.

D. Primers for Amplifying Fused PCR Products

Specific primers may be used to promote the amplification of fused PCR products with two regions over amplified products including only a single region. The specific primers may amplify fused PCR products without amplifying regions that themselves have not yet been amplified. These primers may be included in high concentrations relative to other primers in order to form a large amount of the fused PCR products.

1. Forward Primer without Separate Overlapping Region

Figure 6:
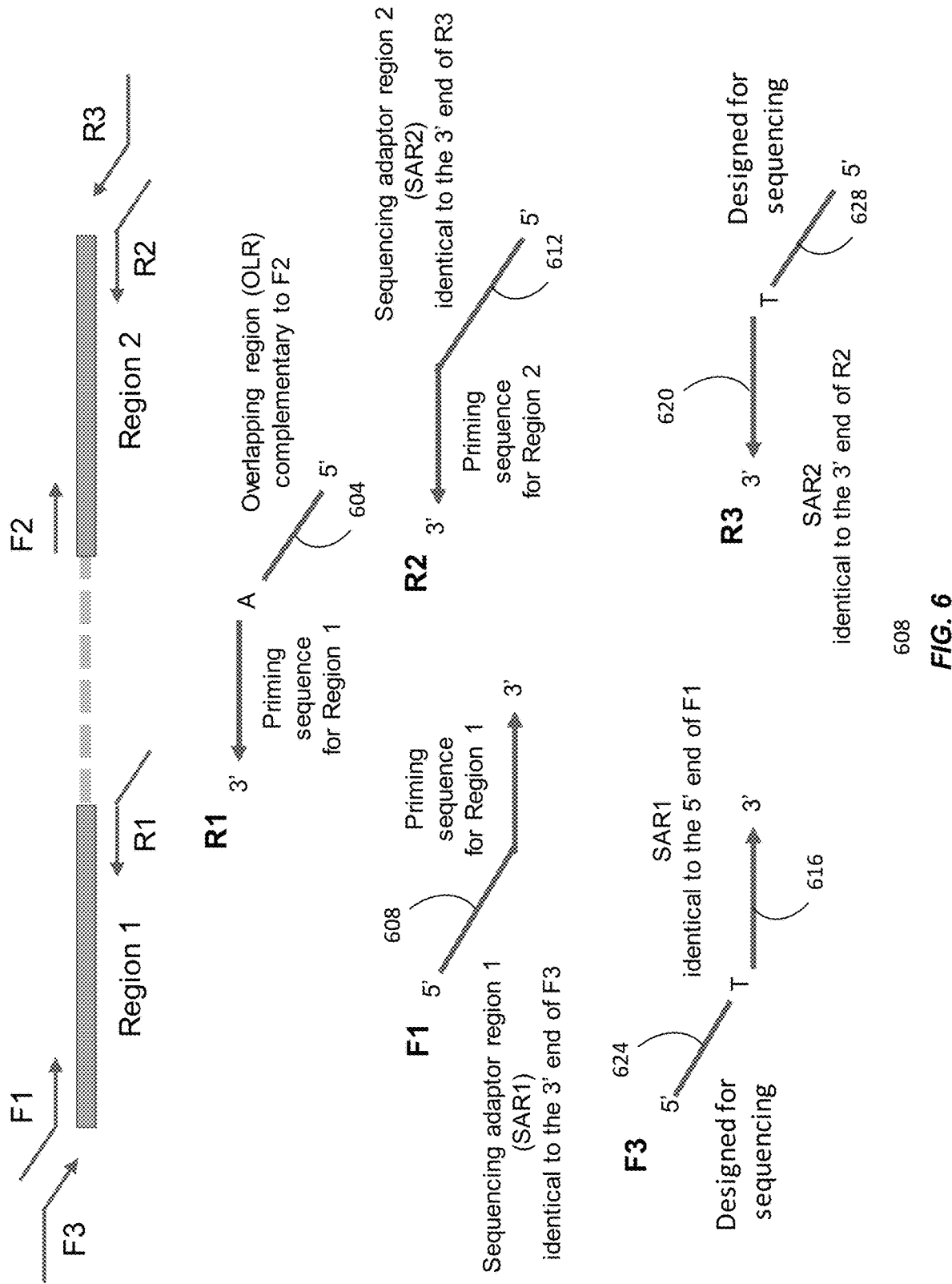
FIG. 6 illustrates the principle of the fusion and adapter ligation PCR method with primers to promote amplifying fused PCR products according to embodiments of the present disclosure.

FIG. 6 illustrates the principle of the fusion and adapter ligation PCR method with primers to promote amplifying fused PCR products. Within the reaction compartment, we add DNA templates and six primers: F1, R1, F2, R2, F3, and R3. The primers F1, R1, F2, and R2 may be similar to primers F5, R5, F6, and R6, respectively, in FIGS. 3A-3F. Region 1 and Region 2 are the two targets that are the target of the haplotype phasing analysis. Region 1 may be similar to Region A in FIG. 3, and Region 2 may be similar to Region B in FIG. 3.

The dotted line represents the genomic region between Region 1 and Region 2. The two regions can be separated by a few kilobases, and the length of the dotted line is not drawn according to scale. F1 and R1 are primers for amplifying Region 1. F2 and R2 are primers that are used for amplifying Region 2. The α' end of R1 contains an overlapping region (OLR) that is complementary to F2. This overlapping allows the linking of Region 1 and Region 2 (as illustrated in FIGS. 3E and 3F).

One key difference in FIG. 6 compared with FIGS. 3A-3F and 4A-4C is the addition of an extra pair of primers F3 and R3. This pair of primers is used for amplifying the fused PCR products containing both Region 1 and Region 2. The inclusion of this pair of primers (F3 and R3) is particularly useful for fusing more than two regions. The use for fusing more than two regions is described in more detail below. As the 5' end 604 of R1 is complementary to F2, PCR products for Region 1 using F1 and R1 can be fused to the PCR products for Region 2. The 5' ends of F1 and R2 (608 and 612) are designed to be of the same sequence as the 3' ends of F3 and R3 (616 and 620), respectively. The overlapping region between F1 and F3 is denoted as Sequencing Adaptor Region 1 (SAR1) and the overlapping region of R2 and R3 is denoted as Sequencing Adaptor Region 2 (SAR2). As a result of SAR1 and SAR2, F3 and R3 can be used to amplify the fused product of Region 1 and Region 2.

An extended amplicon formed by F1, R1, F2, and R2 may be similar to the strands in FIG. 3F. However, because F1 includes SAR1 and R2 includes SAR2, the two strands of DNA located at one end of the extended amplicon would have SAR1 and a sequence complementary to SAR1. The two strands of DNA located at the other end would have SAR2 and a sequence complementary to SAR2. The F3 and R3 primers can then amplify this extended amplicon. The amplified extended amplicons then include the sections 624 of F3 and 628 of R3 designed for sequencing and their complements, e.g., adapters attached to a flow cell. Thus, the amplified extended amplicons can be further amplified with the F3 and R3 primers, which may then be fully complementary to the starting or ending sequences of the amplified extended amplicons.

To reduce the interference of unfused PCR products of Region 1 and Region 2, the concentrations of F3 and R3 can be set to be higher than the concentrations of the other primers F1, F2, R1, and R2. Examples of the ratio of the concentrations of F3 and/or R3 to any one or more of F1, F2, R1, and R2 include, but are not limited to, greater than or equal to 5:1, 10:1, 20:1, 50:1, 75:1, 100:1, 200:1, 500:1, 1000:1, 2000:1, 5000:1, 10000:1, 20000:1, 50000:1, or 100000:1. The lower concentrations of F1, R1, F2, and R2 increase the likelihood that they would be exhausted after forming fused products and there would not be a significant amount of unfused products. The 5' ends of F3 and R3 are designed to facilitate the sequencing of the fused products. The unfused products may fuse with unfused products from another compartment in downstream analysis processes and affect the accuracy of the haplotyping analysis.

In embodiments, an adaptor sequence for the massively parallel sequencing platforms, for example Illumina sequencing adaptor sequences, can be put at the 5' end 624 of F3 and 628 of R3 so as to allow the sequencing of the fused products. In some embodiments, a sequence indicating the identity of the sample, i.e. sample index, can be included so that the samples resulting from different samples or experiments can be pooled for sequencing or other subsequent analysis. After the sequencing, the sequenced reads can be attributed to the respective original samples based on the sample index sequences. These adaptor sequences or sample indices are examples of the portions of F3 and R3 labeled as "Designed for sequencing" in FIG. 6.

2. Forward Primer with Separate Overlapping Region

Figure 7A:
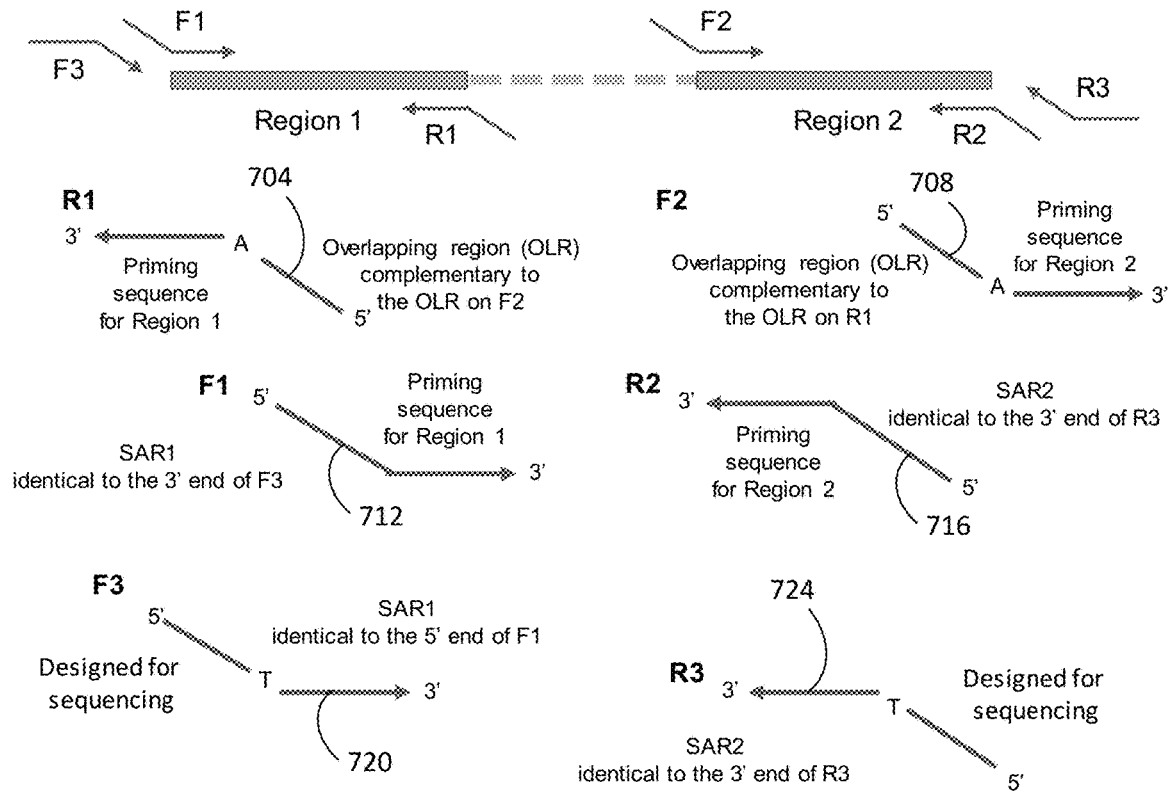
FIGS. 7A-7B show an example of using primers to promote amplifying fused PCR products according to embodiments of the present disclosure.

FIG. 7A shows another example of using primers to promote amplifying fused PCR products. The 5' ends 704 and 708 of each of R1 and F2 can be engineered to be an artificial sequence. The two artificial sequences would be complementary to one other, similar to R5 and F6 in FIG. 5. As with FIG. 6, primers F3 and R3 can be added to promote amplifying fused PCR products. The 5' ends 712 and 716 of F1 and R2 are designed to be of the same sequence as the 3' ends 720 and 724 of F3 and R3, respectively. The overlapping region between F1 and F3 is denoted as Sequencing Adaptor Region 1 (SAR1) and the overlapping region of R2 and R3 is denoted as Sequencing Adaptor Region 2 (SAR2). F3 and R3 can be used to amplify the fused product of Region 1 and Region 2. To reduce the interference of unfused PCR products of Region 1 and Region 2, the concentrations of F3 and R3 are set to be higher than the concentrations of the other primers F1, F2, R1, and R2. Examples of the ratio of the concentrations of F3 and R3 to F1, F2, R1, and R2 include, but are not limited to, greater than or equal to 5:1, 10:1, 20:1, 50:1, 75:1, 100:1, 200:1, 500:1, 1000:1, 2000:1, 5000:1, 10000:1, 20000:1, 50000:1, or 100000:1. The lower concentrations of F1, R1, F2, and R2 increase the likelihood that they would be exhausted after forming fused products and there would not be a significant amount of unfused products.

Figure 7B:
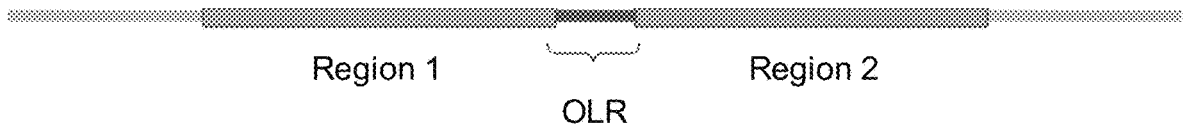

FIG. 7B shows a fused PCR product. The fused PCR products would contain the sequence of the OLR between the two targeted regions.

IV. Linking More than Two Regions

In some embodiments, more than one region can be linked together into an extended amplicon. The linking of more than one region may allow for more regions to be sequenced than if the regions were not linked together. The 5' end of a reverse primer for a first region may be designed to be complementary to a portion of the forward primer for the region downstream (3'). The pattern for the reverse and forward primers may continue for additional regions downstream of the first region.

A. Certain Regions Link Together

FIGS. 8A-8B illustrate a fusion-PCR method for linking more than two regions where only certain regions link to each other according to embodiments of the present disclosure. In FIGS. 8A and 8B, the OLR of a reverse primer of one region is specifically complementary to the end of another region, similar to FIGS. 4A-4C, where OLR is complementary to next forward priming sequence. Accordingly, using the different strategies described above, OLRs can be designed to link more than two regions together.

In FIG. 8A, the OLRs at the 5' end of the reverse primers are complementary to the forward primers of the next region. For example, the added OLR 804 of R1 is complementary to F2, and the added OLR 808 of R2 is complementary to F3, and so on. The resulting extended amplicon would include the regions 1-3 in that order, or potentially just extended amplicons of regions 1 and 2 and just regions 2 and 3. By using a higher concentration of primers F1 and R3, fully extended amplicons can be favored. Similar concentrations as with just two regions can be used for the outermost primers. With this design, multiple regions can be amplified from a single piece of long DNA and linked together. The phase of the alleles at the different regions can be determined using downstream analysis, for example but not limited to massively parallel sequencing.

In FIG. 8B, both the reverse and forward primers include an additional OLR in addition to the priming sequence. The sequence of the OLRs are specific particular linking of regions, e.g., the sequence of the OLR between R1 and F2 (812 and 816) is different than the sequence of the OLR between R2 and F3. The resulting extended amplicon would include the regions 1-3 in that order, which is similar to FIG. 8A, but the technique of FIGS. 5A-5D would be used. Accordingly, in this alternative design, OLRs are engineered at the reverse primers and the forward primers. The OLR of the reverse primer of a previous region would be complementary to the OLR of the forward primer of the next region.

B. Any Regions can Link Together

In some embodiments, the OLR regions can be the same for all regions. In this manner, the linking does not need to be sequential, as there can be any pairwise combination of regions. The paired extended amplicons can be analyzed (e.g., sequenced) to provided haplotype information. For example, paired information of regions 1 and 2, along with paired information of 2 and 3 (or 1 and 3) can provide the haplotype information for 1, 2, and 3. Thus, pairs can be sufficient. This essentially allows random linking between any two pairs of regions.

Figure 9A:
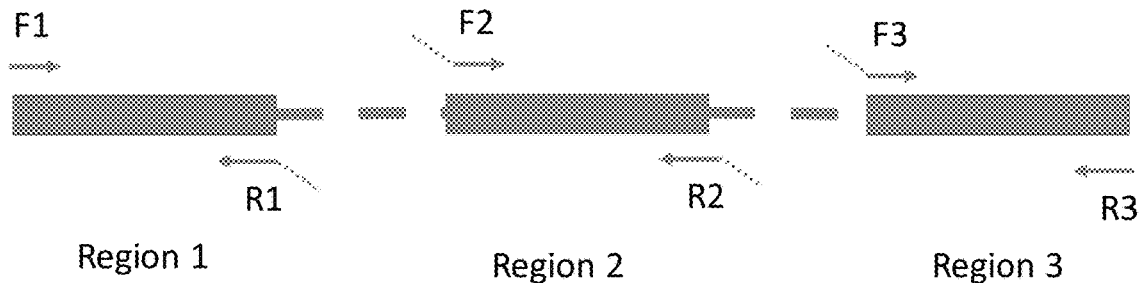
FIGS. 9A-9B illustrate a fusion-PCR method for linking more than two regions where any region can link to each other according to embodiments of the present disclosure.
Figure 9B:
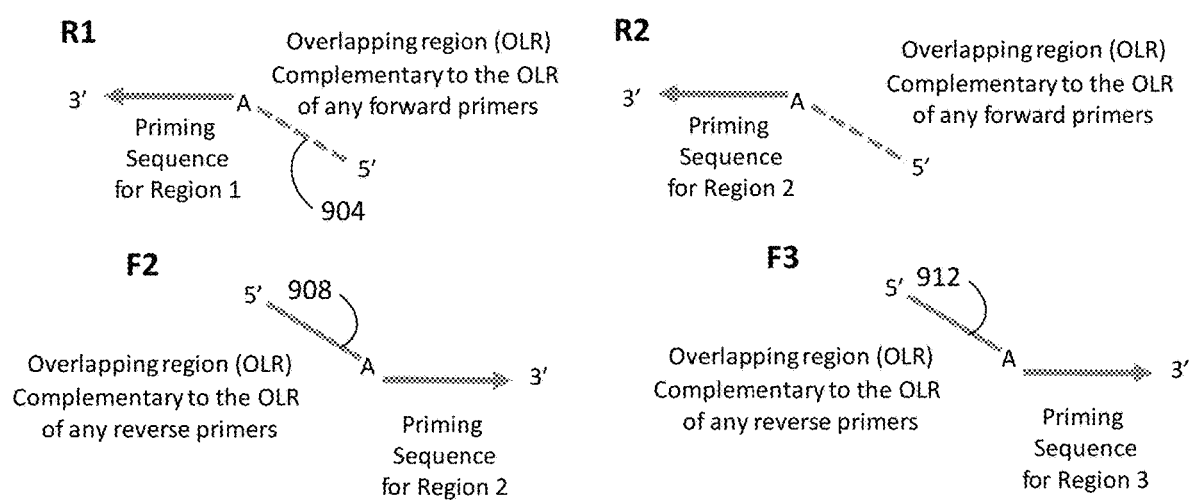

FIGS. 9A-9B illustrate a fusion-PCR method for linking more than two regions where any region can link to each other according to embodiments of the present disclosure. In this other variant, the OLRs located on the reverse and forward primers can be generic. FIG. 9A shows a molecule with three regions (Regions 1, 2, 3) and the associated forward and reverse primers.

FIG. 9B shows details of the primers. For example, the OLR 904 located at the 5' end of the reverse primer R1 for Region 1 is complementary to the forward primers located at the 5' end of the forward primers for Regions 2 and 3 (as well as the forward primers for Regions 4, 5, 6 etc., if present). Thus, all the primers have the OLR. That is, any F and R primers are complementary to each other. With this design, the alleles at Region 1 can be phased with any other regions (Regions 2, 3, 4, etc.). The phase of all the regions can then be deduced.

As an example, assume that there are three regions with SNPs A/T. If it is determined that A in region 1 is linked to A in region 2, then the two A's are on the same haplotype. And if A in region 1 is linked to A in region 3, then it can be determined that the haplotype over all regions is AAA.

C. Primers for Amplifying Fused PCR Products with Multiple Regions

Forward and reverse primers designed to amplify fused products may be used with multiple regions. The forward and reverse primers may be designed similar to the primers for linking two regions in FIGS. 6, 7A, and 7B.

Figure 10A:
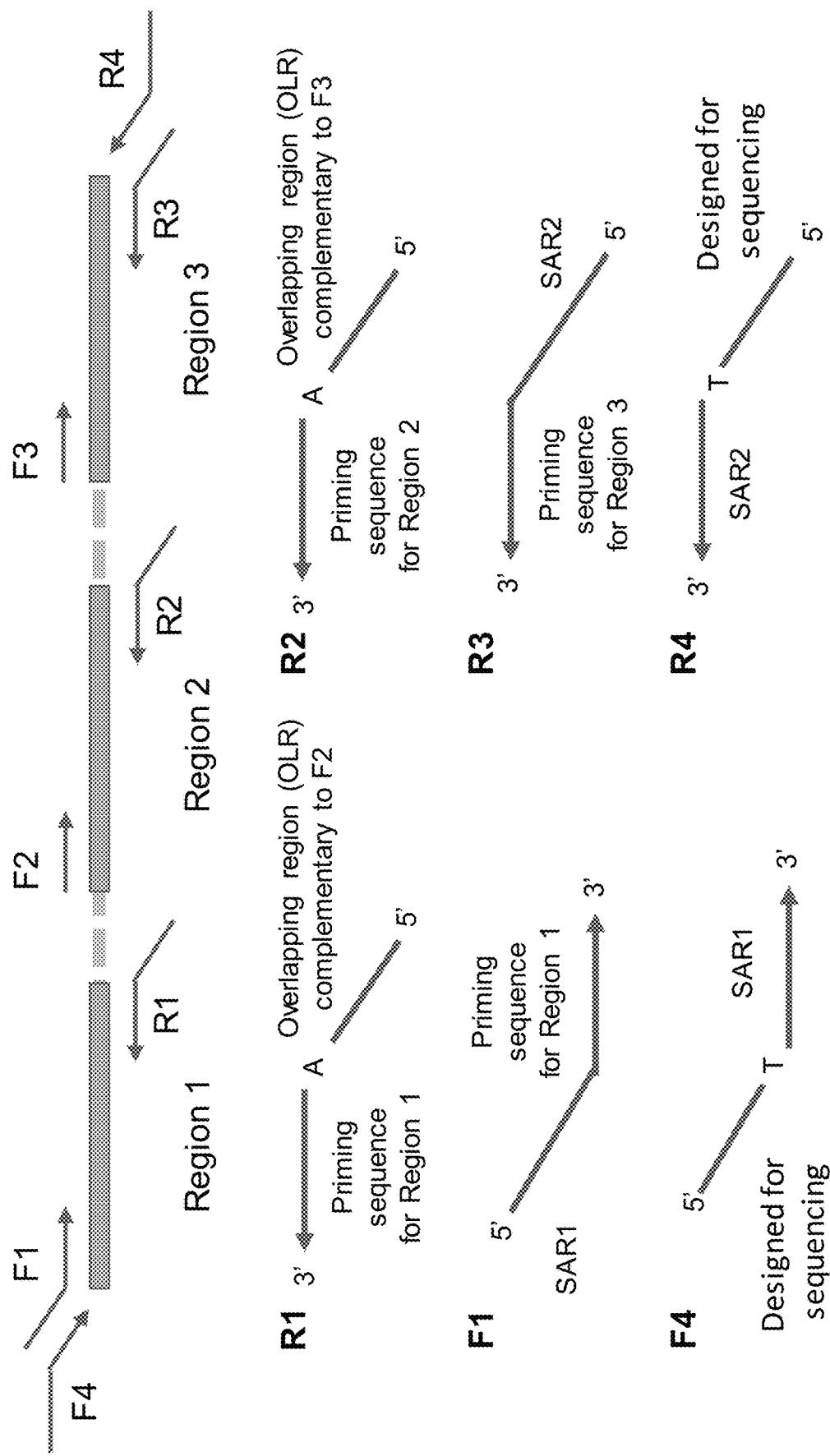
FIGS. 10A-10B show how primers can be used to amplify fused PCR products with multiple regions according to embodiments of the present disclosure.

FIG. 10A shows how primers can be used to amplify fused PCR products with multiple regions. Using the different strategies described above, OLRs can be designed to link 3 or more regions together. The OLRs at the 5' end of the reverse primers would be complementary to the forward primers of the next region. With this design, multiple regions can be amplified from a single piece of long DNA and linked together. This method is similar to the method described in FIGS. 8A-8B except with the addition of a pair of primers (F4 and R4) which 3' ends have the same sequence as the 5' end of F1 and R3, respectively. The addition of this pair of primers is to amplify the completely fused products, which include all the regions to be fused. The preferential amplification of the completely fused product may be achieved by the higher concentrations of F4 and R4, relative to other primers, including F1, F2, F3, R1, R2, and R3. Only the completely fused products linking all the three regions can be amplified by F4 and R4. The partially fused products which link only two regions or unfused PCR products of any of the three regions, cannot be amplified by F4 and R4. Because of the higher concentrations of F4 and R4, the amounts of the completely fused products may be much higher than the unfused PCR products and the partially fused products. Examples of the ratio of the concentrations of F4 and R3 to F1, F2, R1, and R2 include, but are not limited to, greater than or equal to 5:1, 10:1, 20:1, 50:1, 75:1, 100:1, 200:1, 500:1, 1000:1, 2000:1, 5000:1, 10000:1, 20000:1, 50000:1, or 100000:1.

Figure 10B:
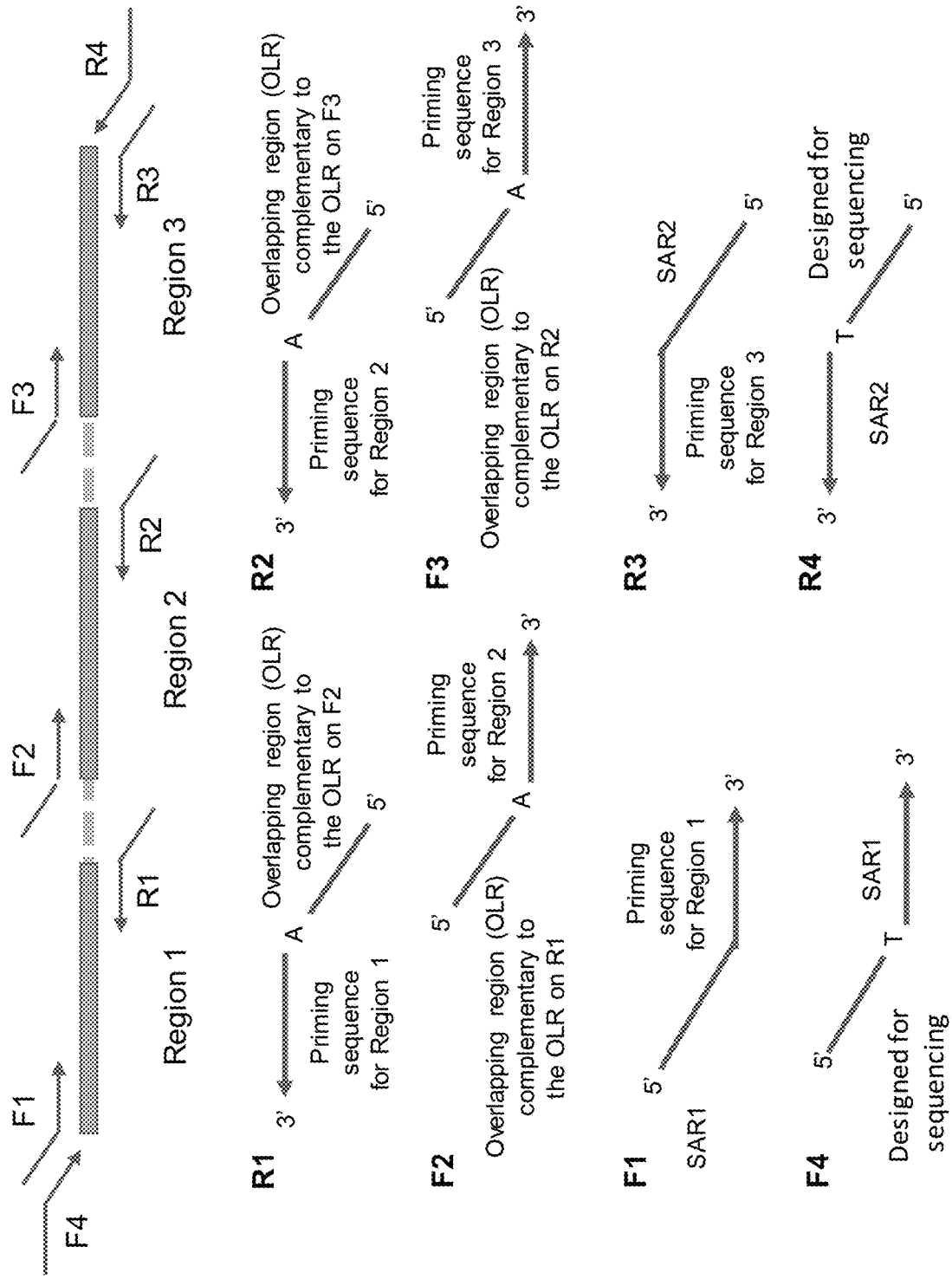

FIG. 10B illustrates amplifying fused PCR products having three regions with forward primers with OLRs as portions separate from portions complementary to the regions, in contrast to the forward primers having the OLR equal to the portion complementary to the region. The fusing of PCR products is similar to the scheme illustrated in FIG. 7A. In FIG. 10B, the use of F4 and R4 at higher concentrations, compared with F1, F2, F3, R1, R2, and R3, can enrich for the completely fused products, similar to the use of F4 and R4 in 10A.

V. Haplotyping Example Using NUDT15 Gene

We use the haplotyping of the variants of the NUDT15 gene as an example to illustrate this haplotyping method.

A. NUDT15

The NUDT15 gene encodes for the enzyme nudix hydrolase 15 that metabolizes 6-mercaptopurine (6-MP), a type of thiopurine drug, is a major component of maintenance treatment for childhood acute lymphoblastic leukemia (ALL). A number of variants in the human NUDT15 gene as critical determinants of thiopurine intolerance (Moriyama et al., Nature Genetics, 2016; 48:367-373). The variants located in exon 1 and exon 3 of the NUDT15 gene can cause loss of function of the nudix hydrolase 15 enzyme and lead to severe immunosuppression when these patients were prescribed with normal dose of 6-MP. The combination of genotypes at these variants results in a number of haplotypes.

Figure 11:
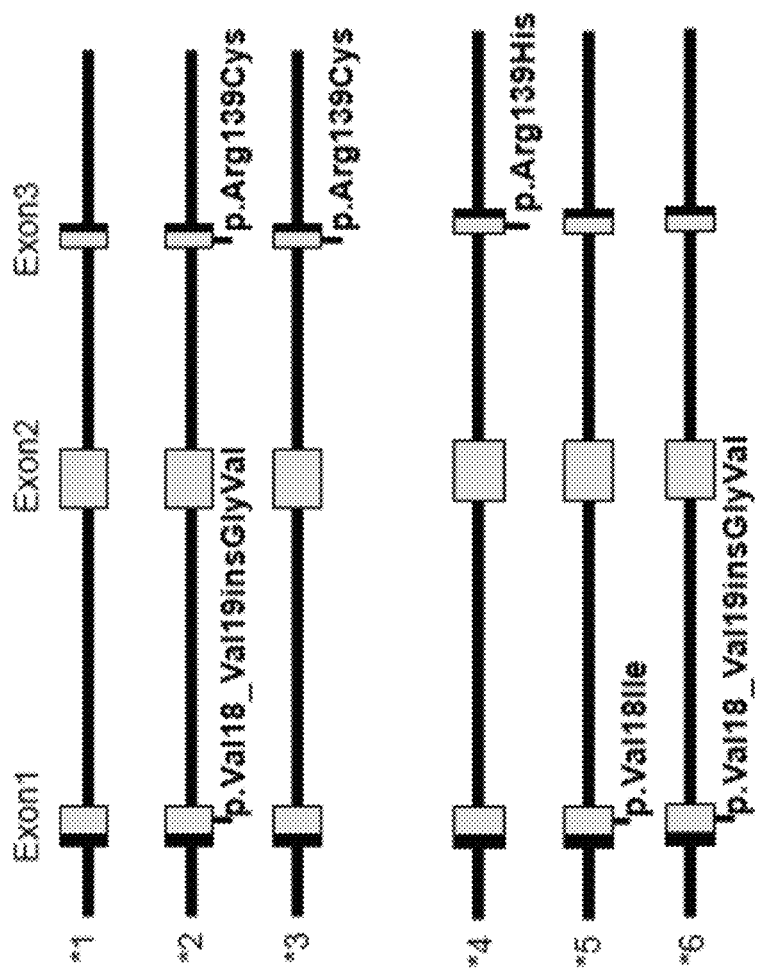
FIG. 11 shows six haplotypes comprising different combinations of genotypes at exons 1 and 3 of NUDT15.

FIG. 11 shows six haplotypes comprising different combinations of genotypes at exons 1 and 3 of NUDT15.

For patients having genetic variants at both exons 1 and 3, it is important to determine the phase of the variants at the two loci because that would affect the metabolism rate of the immunosuppressants and hence the optimal dosage to be given to the patient. For example, when a heterozygous p.Val18_Val19insGlyVal variant is detected at exon 1 and a heterozygous p.Arg139Cys variant is detected at exon 3, the two variants can be located on the same or different chromosomes. When the two variants are on the same chromosome, the patient would have haplotypes *1 and *2. As the patient has a normal copy of the NUDT15 gene, the patient would still be able to produce the functional enzyme nudix hydrolase 15. The dosage of the immunosuppressant would be adjusted to a moderate dose as in the case of having only one variant.

On the other hand, of the two variants are on two different chromosomes, the patient would have haplotypes *3 and *6. In this situation, the patient would not be able to produce any functional nudix hydrolase 15 and the dosage of the immunosuppressant would need to be markedly reduced. In a meta-analysis by Yin et al (Yin et al., Oncotarget, 2017; 8:13575-85), patients with one or two copies of NUDT15 risk alleles required 23% and 65% lower mean daily thiopurine dose compared to patients with wild-type NUDT15, respectively.

The determination of the haplotypes of NUDT15 variants is challenging because of two reasons. First, the distance between the mutational hot spots in exon 1 and exon 3 is as long as around 8 kb. Long-range PCR approaches are limited as the efficiency and robustness of PCR will decrease as the amplicon size increase which will lead to artificial recombinants. Another difficulty is that the V18V19insGV is a 6-bp tandem repeat variation. Therefore, haplotype-phasing methods relying on allelic discrimination by primers or probes, for example multiple duplex PCR, cannot be used (Regan et al., PLoS One, 2015; 10:e0118270). Technologies that provide long range information with short read sequencing, i.e, 10× Genomics, or directly sequencing a single molecule over long distance, i.e., PacBio, are relatively costly and with low throughput. Therefore, it is a good candidate locus to demonstrate the power of this new haplotyping method.

Sixty-three ALL children were recruited from the Department of Chemical Pathology and Pediatrics, Prince of Wales Hospital (PWH), Hong Kong. These patients were originally referred for TPMT genotyping after the occurrence of myelosuppression during the thiopurine treatment. NUDT15 genotyping were performed for all patients by Sanger sequencing. The parents or grandparents of 4 patients who were heterozygous for both V18V19insGV and R139C variants were also genotyped to determine the true haplotypes of the respective patients. The phase of the two variants for these patients was determined by family analysis. In addition, 506 healthy subjects were also analyzed for potential variants at the two NUDT15 loci.

B. High-Resolution Melting Genotyping of NUDT15 Gene

Before proceeding with the haplotyping analysis, we first identified subjects who would be heterozygous at both loci-of-interest as these subjects would be benefited by the haplotyping analysis for the selection of the appropriate dosage of thiopurine treatment. Two high-resolution melting (HRM) assays were designed. One assay targeted a mutational hot spot in exon 1 of the NUDT15 gene containing V18V19insGV, and V18I variants. Another assay amplify a fragment covering R139C and R139H variants in exon 3. The sequences of the primers are listed in Table 1.

TABLE 1

Primers for high-resolution melting analysis of NUDT15 gene

| Primers | Sequence (5'-3') | SEQ ID NO: |
|---|---|---|
| Exon 1 forward | TATGACGGCCAGCGCAC | 1 |
| Exon 1 reverse | ACGCAACGCGGATGCT | 2 |
| Exon 3 forward | CCTCCCCTGGACCAGCTT | 3 |
| Exon 3 reverse | CCACCAGATGGTTCAGATCTTCT | 4 |

For each sample, PCR reaction was run in duplicates. Twenty microliters of reaction mix was prepared, containing 10 µL of 2× LightCycler® 480 High Resolution Melting Master, a final concentration of 300 nmol/L (exon 1 assay) or 250 nmol/L (exon 3 assay) of both forward and reverse primers, a final concentration of 3.5 mmol/L (exon 1 assay) or 2.5 mmol/L (exon 3 assay) of MgCl2, and 20 ng of DNA. For the exon 1 assay, 10% of dimethyl sulfoxide was added to the PCR reaction to improve the amplification.

PCR reactions were carried out using the LightCycler® 96 Instrument. The PCR profile consists of a preincubation at 95° C. for 10 minutes, followed by an amplification program. For the exon 1 assay, the amplification program consists of 50 cycles of 95° C. for 15 seconds, a 1.5° C./s ramp to 59° C. for 20 seconds, and 72° C. for 20 seconds. For the exon 3 assay, the amplification program consists of 45 cycles of 95° C. for 10 seconds, 59° C. for 15 seconds with a ramp rate of 2.2° C./s, and 72° C. for 15 seconds. After PCR amplification, a melting cycle was performed following protocol: 95° C. for 1 minute, 40° C. for 1 minute, and then collecting fluorescence continuously while heating from 60° C. to 90° C. at a rate of 0.04° C./s. High-resolution melting data were analyzed with the LightCycler® 96 Application Software. A wild-type sample was run on each plate as a negative control.

For the 73 ALL-related subjects (i.e., 63 ALL patients and 10 family numbers), the mutational status in exon 1 and exon 3 of the NUDT15 gene has been identified by Sanger sequencing. Sixteen of these subjects carried mutations in exon 1, including 15 subjects with heterozygous V18V19insGV variant and 1 subject with V18I variant. For exon 3, 48 subjects were homozygous for the wildtype sequence, 21 subjects were heterozygous for R139C and wildtype, and 4 subjects were homozygous for R139C. We performed the high-resolution melting analysis to genotype exon 1 and exon 3 of the NUDT15 gene for all subjects.

Figure 12B:
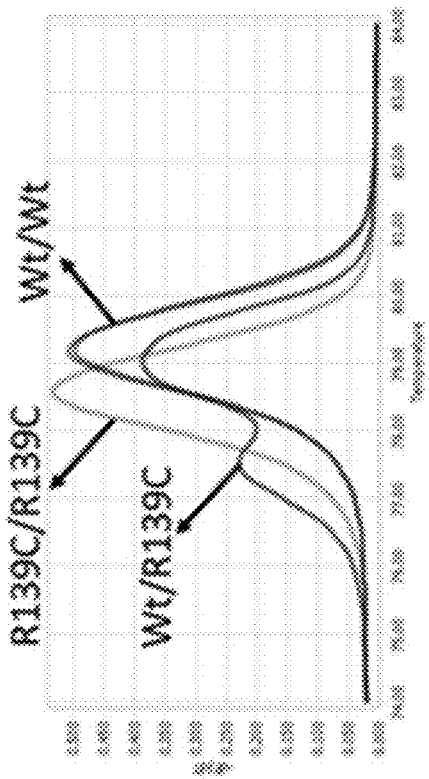
FIGS. 12A-12B show melt curves that differentiate samples with different NUDT15 genotypes in the exon 1 (A) and exon 3 (B) regions.
Figure 12A:
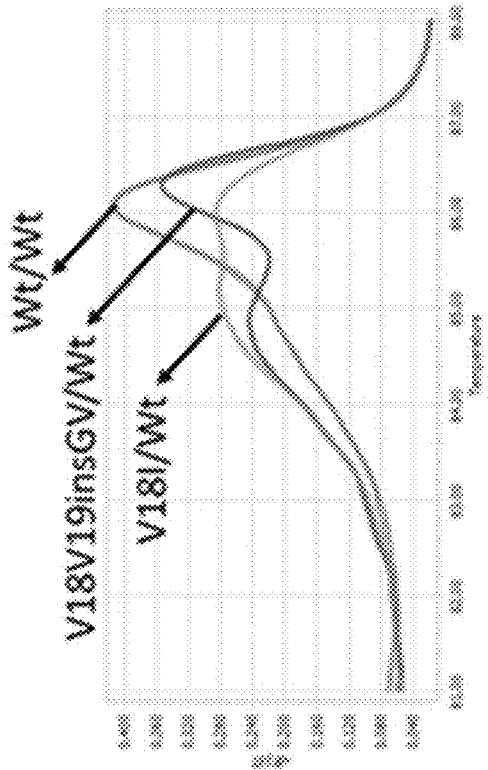

FIGS. 12A and 12B show melt curves that differentiate samples with different NUDT15 genotypes in the exon 1 (A) and exon 3 (B) regions. In FIG. 12A, the HRM analysis targeting exon 1 of the NUDT15 gene differentiated the heterozygous V18V19insGV variant and heterozygous V18I variant from the wild-type sequences based on the shape of normalized melting peaks. In FIG. 12B, the HRM analysis differentiated the two genotypes in exon 3 of the NUDT15 gene (i.e., heterozygous R139C and homozygous R139C) from the wild-type sequences.

C. Droplet Digital Haplotype Fusion-PCR Analysis of NUDT15 Gene

To determine the phase of the variants at the two NUDT15 loci, we developed a droplet digital PCR-based fusion-PCR haplotyping method. High molecular mass DNA extracted from buffy coat were distributed into nanoliter droplets to carry out linking PCR using the BioRad Droplet Digital PCR system. The concentration of the DNA template was controlled to fill only approximately 10% of the droplets so that >99% of the droplets would contain only one or no template DNA covering the two regions-of-interest. Fusion PCR was performed so that the two regions carrying the variants can be amplified from a single long DNA molecule and linked together.

FIGS. 13A-13F show the application of a fusion-PCR method on exons 1 and 3 of the NUDT15 gene according to embodiments of the present disclosure. FIGS. 13A-13F mirror FIGS. 3A-3F, although the techniques of other methods can be used, e.g., FIGS. 4A-4C and 5A-5D.

Figure 13A:
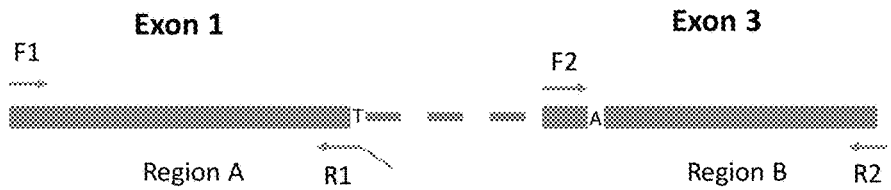
FIGS. 13A-13F show the application of a fusion-PCR method on exons 1 and 3 of the NUDT15 gene according to embodiments of the present disclosure.

In FIG. 13A, the fusion-PCR assay used for haplotyping the NUDT15 gene comprise two pairs of primers, one pair (F1 and R1) for amplifying the variant region on exon 1 and the other pair (F2 and R2) amplified the variant region ion exon 3.

Figure 13B:
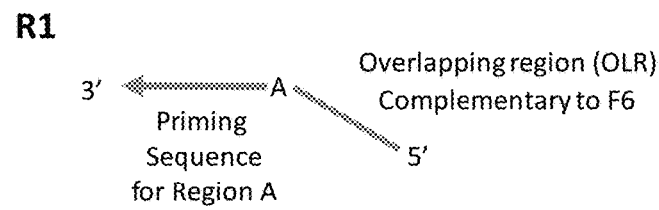

In FIG. 13B, the reverse primer for exon 1 (R1) has a linker sequence at its 5' end that is complementary to the sequence of the forward primer for exon 3 (F2).

Figure 13C:
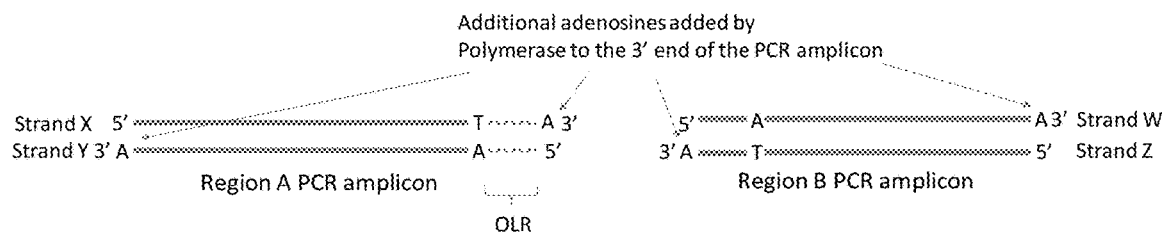

In FIG. 13C, in the initial rounds of the PCR reaction, the two regions are amplified separately. The two PCRs were performed simultaneously within one single droplet. As discussed previously, additional adenosines [A] would be added by the Taq polymerase at the 3' end of the extended strands of DNA.

Figure 13D:
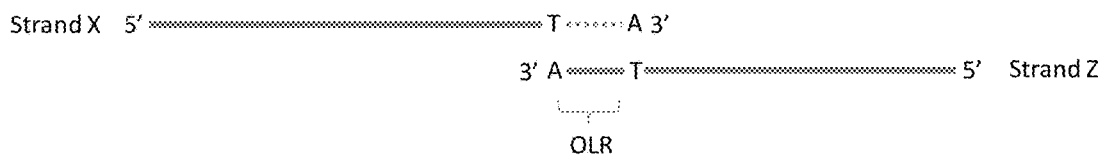

In FIG. 13D, the OLR engineered to the 5' end of R1 would make the 3' end of Strand X complementary to the 3' end of Strand Z.

Figure 13E:
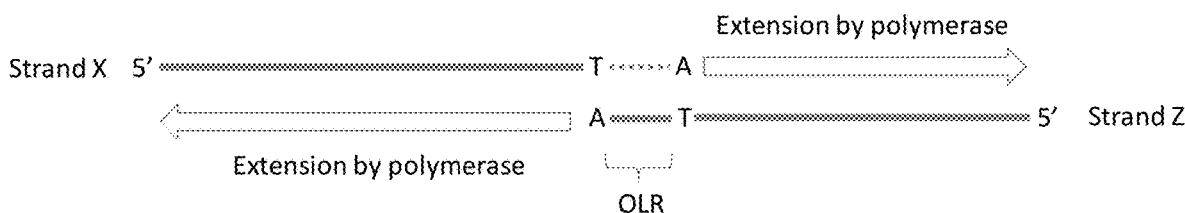

In FIG. 13E, the two strands can be linked together with the extension by the Taq polymerase or other polymerases.

Figure 13F:
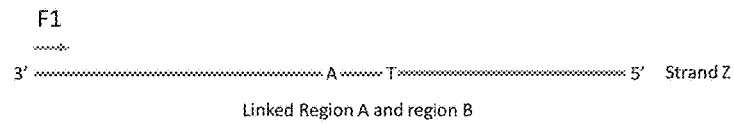

In FIG. 13F, further PCR amplification on the linked product using primers F1 and R2 would be performed as the concentrations of F1 and R2 were higher than the concentrations of R1 and F2. The size of fused PCR product should be 190 bp when the haplotype carrying the p.V18V19insGV mutation, or 184 bp otherwise.

TABLE 2

Primers for haplotype fusion PCR of NUDT15 gene

| Primers | | Sequence (5'-3') | SEQ ID NO: |
|---|---|---|---|
| Forward primer | (F1) | TATGACGGCCAGCGCAC | 1 |
| Reverse primer | (R1) | CCAGGGGAGGTAGTTCTTCCCAC GCAACGCGGATGCT | 5 |
| Forward primer | (F2) | GGGAAGAACTACCTCCCCTGG | 6 |
| Reverse primer | (R2) | CCACCAGATGGTTCAGATCTTCT | 4 |

PCR reactions were prepared in four replicates for each sample in a volume of 20 µL, consisting of 2.5 ng of template DNA, 10 µL of 2×ddPCR Supermix for Probes (No dUTP) (Bio-Rad), a final concentration of 1 µmol/L of both F1 and R2, and a final concentration of 30 nmol/L of both R1 and F2. The PCR reaction mix was then partitioned using the QX100/QX200 Droplet Digital PCR Generator (Bio-Rad). The thermal profile of the assay was: initiated at 95° C. for 10 minutes, followed by 45 cycles of 94° C. for 30 seconds and 61° C. for 1 minute, and a final incubation at 98° C. for 10 minutes.

After the PCR reaction, droplets of replicated wells from one sample were pooled and the PCR products were recovered following the manufacturer's protocol with a minor adjustment of using 40 µL of TE buffer for each well instead of 20 µL. This adjustment resulted in a better breaking of droplets.

To enrich the desirable fused PCR products with a length of 184 or 190 bp, the recovered PCR products were further purified using AMPure XP Beads following the manufacturer's Dual Bead-based Size Selection Protocol. The bead/DNA ratio (i.e., the ratio of the accumulated volume of beads added to the volume of original sample) for the first and second bead selection was 0.8 and 1.6, respectively. The size profile of the purified fused PCR products was then analyzed using D1000 SreenTape and Reagents with the 4200 TapeStation instrument (Agilent Technologies).

D. Sequencing of NUDT15 Gene Fused PCR Products

The fused PCR products were analyzed by next-generation sequencing, although other measurement techniques may be used, if suitable for the sequences of the linked regions. An indexed library was constructed for fused PCR products from each sample using the KAPA Library Preparation Kit (Kapa Biosystems) according to manufacturer's recommendations. Up to 48 indexed libraries were multiplexed and sequenced using the Illumina MiSeq sequencing platform (76×2 cycles). The six possible sequences of fused PCR products corresponding to the six haplotypes were used as the reference sequences for the mapping of sequencing data (sequence reads). The paired-end reads were aligned to the 6 reference sequences using the Bowtie 2 program (bowtie-bio.sourceforge.net/bowtie2/). Paired-end reads with both ends aligned concordantly to a reference sequence with no mismatch were used for the further analysis.

The reads mapped to each haplotype sequence in a sample was counted using a Perl script. The percent of reads mapping to each haplotype (denote as Hap %) in a sample was then calculated by dividing the number of reads mapped to each haplotype with the total number of reads mapped to all haplotypes. We set the Hap %<10%, 40%-60%, and >90% as cutoffs for carrying 0, 1, and 2 copies of haplotypes in a sample, respectively. In other embodiments, other percentages, for example but not limited 1%, 2%, 5%, 15%, 20% can be used for the cutoff for carrying 0 haplotype in a sample. Similarly, examples of 25%, 30%, 35%, 40%, 45%, 50%, 55%, 60%, 65%, 70%, can be used as cutoffs for carrying 1 haplotype. Similarly, examples of 75%, 80%, 85%, 92%, 94%, 98%, 99% can be used as cutoffs for carrying 2 haplotypes.

The combinations of haplotypes (i.e, diplotypes) for most of the 73 subjects could be determined from genotyping results by the HRM analysis except for 9 subjects with double heterozygous mutations for V18V19insGV and R139C. Eight of these 9 subjects was identified to be *1*2 by the family analysis. To directly determine the diplotypes, we performed the droplet digital fusion-PCR followed by next-generation sequencing for all subjects. Following the criteria described above, the number of copies of each of the 6 potential haplotypes for all subjects was calculated. The results are summarized in Table 3. The diplotypes of NUDT15 gene were correctly identified in all subjects.

TABLE 3

Haplotypes of NUDT15 gene determined by droplet digital fusion PCR analysis in ALL-related subjects.

| Diplotype | No. of samples | Copies of haploid NUDT15 | | | | | |
|---|---|---|---|---|---|---|---|
| | | *1 | *2 | *3 | *4 | *5 | *6 |
| *1*1 | 44 | 2 | 0 | 0 | 0 | 0 | 0 |
| *1*2 | 9 | 1 | 1 | 0 | 0 | 0 | 0 |
| *1*3 | 11 | 1 | 0 | 1 | 0 | 0 | 0 |

TABLE 3-continued

Haplotypes of NUDT15 gene determined by droplet digital fusion PCR analysis in ALL-related subjects.

| Diplotype | No. of samples | Copies of haploid NUDT15 | | | | | |
|---|---|---|---|---|---|---|---|
| | | *1 | *2 | *3 | *4 | *5 | *6 |
| *1*6 | 4 | 1 | 0 | 0 | 0 | 0 | 1 |
| *2*3 | 2 | 0 | 1 | 1 | 0 | 0 | 0 |
| *3*3 | 2 | 0 | 0 | 2 | 0 | 0 | 0 |
| *3*5 | 1 | 0 | 0 | 1 | 0 | 1 | 0 |

E. Genotyping and Haplotyping of NUDT15 Gene in 506 Healthy Subjects

To evaluate the power and applicability of using the HMR method and the digital fusion-PCR haplotyping method for NUDT15 gene testing, we further analyzed 506 healthy subjects.

The 506 subjects were first screened for NUDT15 variants using the two HMR assays. The results are listed in Table 4. Six different diplotypes including *1*1, *1*3, *1*5, *1*6, *2*3, and *3*3 could be determined directly from the genotyping results. In addition, 22 samples carried double heterozygous variants for V18V19insGV and R139C, and one subject has unknown genotypes in exon 1. For these 23 samples, the digital fusion PCR followed by sequencing was used to determine their diplotypes.

All the 22 compound heterozygous subjects were determined as *1*2 diplotype from the sequencing results. The subject with unknown genotypes in exon 1 was identified as carrying both V18V19insGV and V18I mutations. Thus, the diplotype of this subject is *5*6, which is a previously unknown diplotype. The NUDT15 diplotype frequencies in our cohort are also listed in Table 4. These results are comparable to that determined based on phased data from the 1000 Genomes project for East Asian (Moriyama et al. Nat Genet. 2016; 48:367-373).

TABLE 4

Diplotypes of NUDT15 gene in control subjects determined by HRM and digital fusion PCR.

| Genotype of Exon 1 by HRM | Genotype of Exon 3 by HRM | Diplotype determined by HRM | Diplotype determined by digital fusion PCR | No. of samples | Diplotype frequency |
|---|---|---|---|---|---|
| Wt/Wt | Wt/Wt | *1*1 | — | 380 | 75.1% |
| Wt/Wt | R139C/Wt | *1*3 | — | 62 | 12.3% |
| V18I/Wt | Wt/Wt | *1*5 | — | 12 | 2.4% |
| V18V19insGV/Wt | Wt/Wt | *1*6 | — | 22 | 4.3% |
| V18V19insGV/Wt | R139C/R139C | *2*3 | — | 5 | 1.0% |
| Wt/Wt | R139C/R139C | *3*3 | — | 2 | 0.4% |
| V18V19insGV/Wt | R139C/Wt | — | *1*2 | 22 | 4.3% |
| Unknown | Wt/Wt | — | *5*6 | 1 | 0.2% |

VI. Haplotyping with Phase Assembly Analysis

Haplotyping may involve determining the alleles at more than two heterozygous loci and therefore more than two regions with SNPs. In such cases, these regions can be assembled into fused products of only two or three regions. The haplotype can then be determined through analysis of the resulting two or three region products. Different multiple region products can be linked together by a common region. This analysis of the haplotyping using common regions to link together different fused products is described in greater detail below.

A. Grouping Regions

Figure 14A:
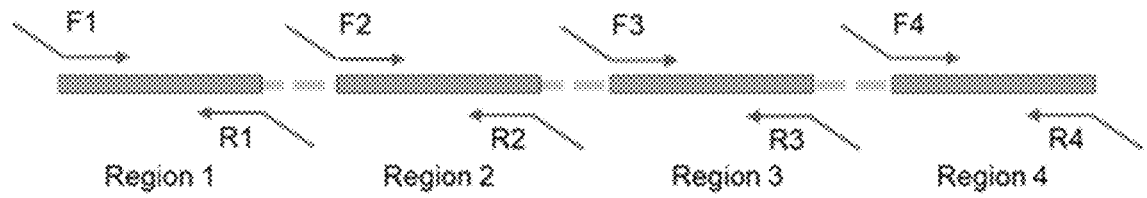
FIGS. 14A-14C show four regions to be haplotyped being divided up into several groups of two regions according to embodiments of the present disclosure.
Figure 14B:
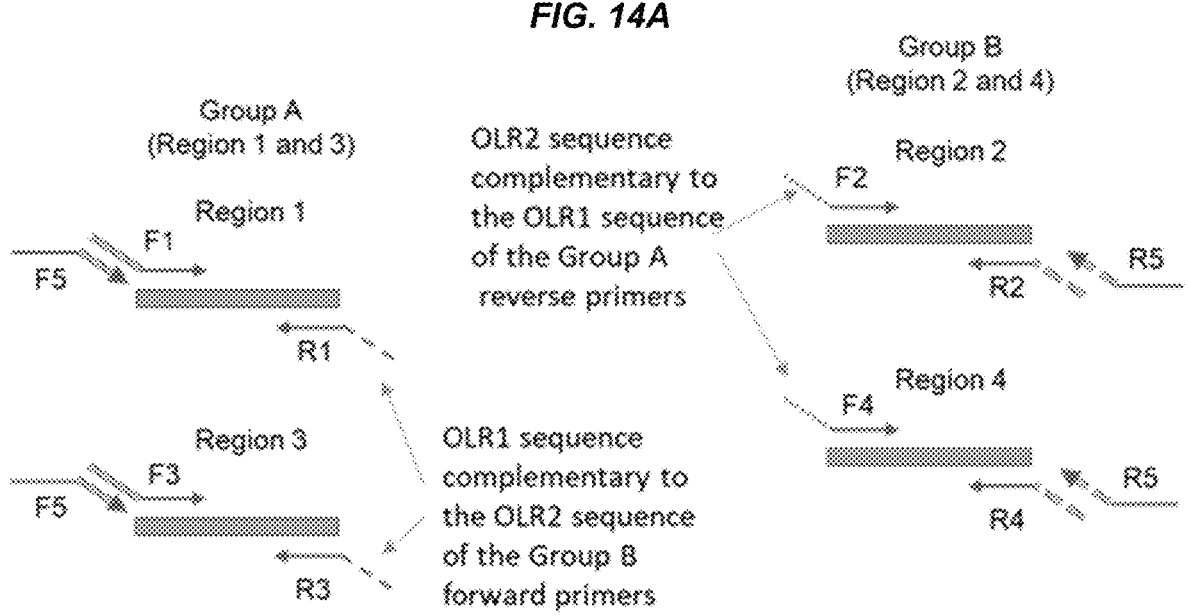
Figure 14C:
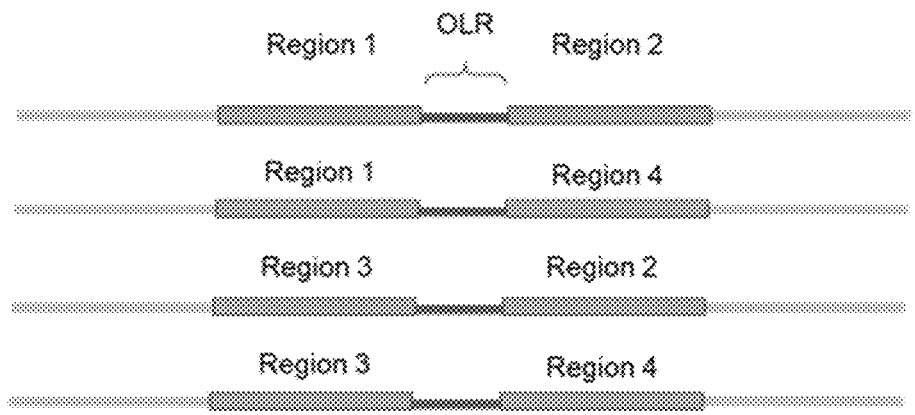

FIGS. 14A, 14B, and 14C show four regions being divided up into several groups of two regions. In FIG. 14A, four regions are shown in this illustrative example. However, the number of regions would not be limited and can be equal to any number of regions to be phased. Each of the four regions have corresponding forward and reverse primers, potentially with primer portions and overlap portions.

FIG. 14B shows two groups of regions and the configuration of the primers. For illustrative purposes, the four regions are divided into two groups (Group A and Group B). The number of groups depends on the number of regions to be phased or haplotyped, as well as the length DNA can be determined by the downstream analysis, for example by massively parallel sequencing. For example, using an Illumina sequencing platform, a paired end sequencing of 150 bp on each end can be performed. Under this arrangement, a total length of 300 bp would be sequenced for any fused DNA molecules. Assuming that the amplified product of each region is 75 bp and the linking regions are 25 bp, the sequencing of 300 bp can reveal the sequence of up to 3 regions in a fused molecule. Under such arrangement, up to three groups can be used for grouping the regions. If there are 30 regions need to be haplotyped, then each group can consist of 10 regions. The number of regions in each group can be equal or unequal. If the downstream analysis can reveal the sequence of longer DNA molecules, then more groups can be used.

FIG. 14B also shows the configuration of the primers based on the two groups. The primers within each group have the same overlapping regions, which are complementary to the overlapping regions of the other group. Here, the overlapping region 1 (OLR1) located at the 5' ends of the Group A reverse primers are complementary to the overlapping region 2 (OLR2) located at the 5' ends of the Group B forward primers. This design of primers is similar to the method described in FIG. 7A above. F5 and R5 are a pair of primers that can specifically amplify fused products including a region in Group A and a region in Group B. The concentrations of F5 and R5 may be higher than concentrations of the other primers (F1 to F4 and R1 to R4). With these higher concentrations of F5 and R5, after the fusion PCR, the concentrations of the fused products may be much higher than those of unfused PCR products.

FIG. 14C shows the fusion products involving Group A and Group B regions. After the fusion PCR, any member in Group A can be fused with a member in Group B. In this example, there are two members in Group A (Region 1 and Region 3) and two members in Group B (Region 2 and Region 4). Therefore, there are four types of fused products: Region 1 fused with Region 2, Region 1 fused with Region 4, Region 3 fused with Region 2, and Region 3 fused with Region 4. Using this design, the size of the fusion products can be easily controlled. In this example, all the fusion products would include only two regions. An example with three regions is provided below.

The advantage of fusing smaller groups of regions over the sequentially linked method described with FIG. 10A or FIG. 10B is the ability to phase more regions. For example, the Illumina sequencing platform is one commonly used platform for determining the sequence of individual molecules. The number of regions that can be phased using a sequentially fused method described in FIG. 10A or FIG. 10B is limited by the length of the sequenced reads of the read out. For example, using a paired-end sequencing of 300 nucleotides on each end, molecules of up to 600 nucleotides can be sequenced. If each region to be phased is 50 nucleotides, then a maximum of 12 regions can be phased using the sequential fusing method.

However, using the grouping method described here, there is theoretically no maximum limit in the number of regions to be phased. In this arrangement, a multiplex PCR that simultaneously amplified the targeted regions (regions to be haplotyped) can be performed in a single compartment. The amplified products of these regions are then fused with the method described in this application. Methods have been described to improve the number of multiplex in a single reaction (Wei et al. Journal of Virological Methods 2008; 151:132-139; Mo et al. Clin Chem Lab Med; 50:649-654). For example, using four groups with each group including 20 regions, a total of 80 regions can be phased. Each fused product may include four regions. With each region being 50 nucleotides, then the fused product would have 200 nucleotides, which is easily within the capability of the Illumina sequencing platform.

The haplotyping can also involve a bioinformatic analysis that assigns different alleles to be on the same haplotype based on paired relationships. Accordingly, the number of regions to be haplotyped may not be limited by the length of the template DNA used for fusion PCR. A common region between two sets of fused PCR products may be used to link together the haplotypes of other regions in the fused products. For example, the haplotypes of three regions (e.g. SNP 1, SNP 2, and SNP 3) can be inferred when the phase of SNP 1 and SNP 2 and the phase of SNP 2 and SNP 3 are determined. This analysis can be repeated to haplotype multiple regions, as described below.

FIGS. 15A, 15B, and 15C show forming fused products of three regions, with one region from each of three groups. FIG. 15A illustrates randomly splitting regions into three groups as an example. However, more than 3 groups (e.g., 4, 5, 6, 7, or more) can be used for this method. For illustrative purposes, the regions are sequentially assigned to the three groups. The sequence of assigning the regions to the groups may not affect the results. In some embodiment, the assignment of regions to the groups can be random rather than sequential.

FIG. 15B shows the configuration of primers based on the groups. The OLR located at the 5' end of each reverse primer in one group is complementary to the OLR located at the 5' end of each forward primer in the next group. In this illustrative example, the OLR of the Group A reverse primers are complementary to the OLR of the Group B forward primers, with the OLRs illustrated by dotted lines. The OLR of the Group B reverse primers are complementary to the OLR of the Group C forward primers, with the OLRs illustrated by dashed lines.

The pair of outer primers Fz and Rz are used for amplifying the completely fused products. Fz has an OLR that is the same as the 5' end of F1 and F4, with the OLR depicted by double solid lines. Rz has an OLR that is the same as the 5' end of R3 and R6, with the OLR depicted by double dashed lines. The concentrations of Fz and Rz may be higher than the concentrations of all other primers used for amplifying the specific regions to promote amplification of fused products of three regions. Examples of the ratio of the concentrations of Fz and Rz to other primers include, but are not limited to, greater than or equal to 5:1, 10:1, 20:1, 50:1, 75:1, 100:1, 200:1, 500:1, 1000:1, 2000:1, 5000:1, 10000:1, 20000:1, 50000:1, or 100000:1.

FIG. 15C shows the fused PCR product. With this design, each completely fused product includes three regions: one in Group A, one in Group B, and one in Group C.

B. Fusion PCR Using Polymerase without Adding Adenosine at the 3' End

Figure 16A:
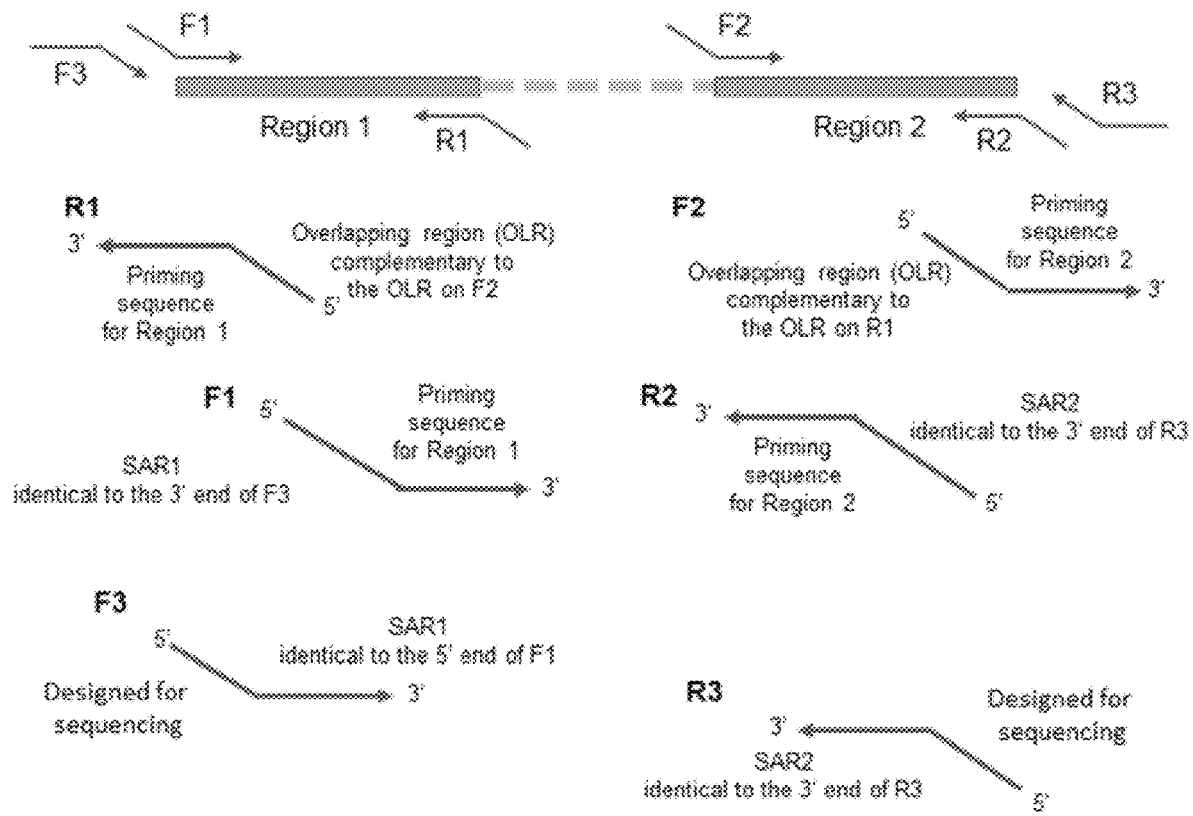
FIGS. 16A-16B show forming fused products without the addition of an adenosine in the primers according to embodiments of the present disclosure.
Figure 16B:

In embodiments, fusion PCR can be performed with the use of a polymerase that does not add an adenosine at the 3' end of the extended strand of DNA. FIG. 16A shows the design of the primers. The illustrated design is similar to the one described in FIG. 7A. However, the primer R1 in FIG. 16A is modified to remove the adenosine flanking between the priming sequence for Region 1 and the OLR. Similarly, the primer F2 is modified to remove the adenosine flanking between the priming sequence for Region 2 and the OLR. The primer F3 is modified to remove the thymine flanking between SAR1 and the sequence located at the 5' end which is designed for sequencing. The primer R3 is modified to remove the thymine flanking between SAR2 and the sequence located at the 5' end which is designed for sequencing. FIG. 16B shows the fused PCR product with two regions. The methods described with FIGS. 14A-14C and FIGS. 15A-15C can be used with this modification in the primer design and the use of a polymerase without adding an extra adenosine at the 3' end of the extended DNA strand.

C. Effect of Length Between Regions

Regions spaced at varying distances from each other were linked together. The fused regions were then analyzed to determine how length affects the accuracy of haplotype analysis.

1. Example configuration of 10 SNPs

FIG. 17A shows lengths between different SNPs in a DNA molecule. These different lengths were used to determine the effect of length on the fusion PCR method. Each fusion PCR aims to fuse two regions, one being SNP1 and the other can be one member of SNP2, SNP3, SNP4, SNP5, SNP6, SNP7, SNP8, SNP9, or SNP10. The distance between the two regions to be fused ranged from 2.5 kb to 100 kb.

FIG. 17B shows the configurations of the primers for the SNPs. The two regions were fused using the method described with FIG. 7A and FIG. 7B. The 5' end of the reverse primer for amplifying SNP1 (primer R1) includes overlapping region 1 (OLR1). The 5' ends of forward primer for amplifying SNP2 to SNP10 include overlapping region 2 (OLR2). OLR1 and OLR2 are complementary. With this design, the PCR products for SNP1 can be fused with each of the PCR products of SNP2 to SNP10. However, the ability of correctly phasing SNP1 and one of the SNP2 to SNP10 may depend on whether an intact long DNA molecule covering the two SNPs to be phased is present in a single compartment, which, for example, may be a droplet of a droplet digital PCR.

2. Results

We recruited a pregnant woman from the Department of Obstetrics and Gynaecology, Prince of Wales Hospital (PWH), Hong Kong. We obtained a peripheral blood sample and harvested the maternal buffy coat. We also obtained a fetal sample by sampling the placenta after delivery. The maternal buffy coat and the fetal placenta tissue were genotyped using an Illumina microarray platform (HumanOmni2.5). We selected 10 SNPs that are located on Hemoglobin gamma 2 and Hemoglobin epsilon 1 genes from chromosome 11. The distances of the second, third, fourth, fifth, sixth, seventh, eighth, ninth, and tenth SNPs from the first SNP are approximately 2.5, 5, 10, 20, 30, 40, 50, 75, and 100 kb, respectively. The SNPs are homozygous in the fetus and heterozygous in the mother. In this case, the fetus had inherited two identical haplotypes, one from each parent. Based on the haplotype information of the fetus and the genotype information of the mother, the two haplotypes of the mother can then be deduced. This haplotype information of the mother could serve as a gold standard for determining the accuracy of the digital fusion PCR method.

FIG. 18 shows the sequences of primers for amplifying each region. The first column shows the SNP ID of the 10 SNPs. The second column indicates the coordinate of the SNP on chromosome 11. The third column states the distance from the first SNP in kilobases. The fourth column lists the genotype of the SNP. The fifth column lists the sequence of the forward primer. The sixth column lists the sequence of the reverse primer. The reverse primer for SNP1 includes OLR1 (highlighted in yellow and underlined). OLR1 is complementary to each OLR2 (highlighted in green and underlined) of the forward primers for SNP2 through SNP10. The base "A" highlighted in red and bolded represents an additional base between the OLR and the priming sequence.

High-molecular-mass DNA was extracted from the maternal buffy coat with MagAttract HMW DNA Kit (Qiagen). For each assay, PCR reaction was prepared in a volume of 20 μL, consisting of 3.2 ng of template DNA, 10 μL of 2× ddPCR Supermix for Probes (No dUTP) (Bio-Rad), a final concentration of 1 μmol/L of each of a pair of inner adapter primers, a final concentration of 40 nmol/L of the reverse primer for SNP 1 and the forward primer for another SNP, and a final concentration of 50 nmol/L of the forward primer for SNP 1 and the reverse primer for another SNP. The PCR reaction mix was then partitioned using the QX100/QX200 Droplet Digital PCR Generator (Bio-Rad). The thermal profile of the assay was the following: initiated at 95° C. for 10 minutes; followed by 50 cycles of 94° C. for 45 seconds, 59° C. for 1 minute, and 72° C. for 3 minutes; and a final incubation at 98° C. for 10 minutes.

After the PCR reaction, we broke the droplets and recovered the PCR products following the manufacturer's protocol with a minor adjustment of using 60 μL of TE buffer for each well instead of 20 μL. This adjustment resulted in a better breaking of droplets.

The PCR products were further purified using AMPure XP Beads following the manufacturer's protocol to remove the residual primers and other undesirable short fragments (size <100 bp). The bead/DNA ratio (i.e., the ratio of the volume of beads added to the volume of sample) was 0.9.

To prepare the library for sequencing, we ligated the outer adapter sequences to the fused PCR products by PCR. The outer adapter primers included a forward primer with the sequence: 5'-AATGATACGGCGACCACCGAGATCTA-CACATACGAGATCCGT-3' (SEQ ID NO: 7) and an index reverse primer with the sequence: 5'-CAAGCAGAA-GACGGCATACGAGAT-index-GTGACTGGAGTTC-3' (SEQ ID NOS 8 and 9, respectively). PCR reaction was prepared for each sample in a volume of 50 μL, consisting of the fused PCR products, 25 μL of KAPA HiFi HotStart ReadyMix (Roche), and a final concentration of 0.5 μmol/L of both outer adapter primers. The thermal profile of the assay was: initiated at 98° C. for 45 seconds; followed by 10 cycles of 98° C. for 15 seconds, 60° C. for 30 seconds, and 72° C. for 30 seconds; and a final incubation at 72° C. for 1 minute.

To enrich the desirable library sequences with a length between 200 to 300 bp, the recovered PCR products were further purified using AMPure XP Beads following the manufacturer's Dual Bead-based Size Selection Protocol. The bead/DNA ratio (i.e., the ratio of the accumulated volume of beads added to the volume of original sample) for the first and second bead selection was 0.6 and 1.4, respectively. The size profile of the purified libraries was then analyzed using D1000 SreenTape and Reagents with the 4200 TapeStation instrument (Agilent Technologies).

Index libraries were multiplexed and sequenced using the Illumina MiSeq sequencing platform (76×2 cycles). The PhiX Control v2 Library (Illumina) was spiked in as quality control. The spiked-in PhiX could also improve sequencing quality as it increases the library complexity, especially for the low-diversity and highly repetitive libraries like the fused DNA library. Examples of the percentages of spike-in PhiX include but limited to 5%, 10%, 20%, 30%, 40%, 50%, 60%, 70%, and 80%. In one embodiment, we spiked in 33% of PhiX. We customized the sequencing primers used for read 1 for the run on an Illumina system. We mixed 2/3 of custom read 1 primers with 1/3 Illumina read 1 primers. The custom read 1 primers enable the sequencing of fused PCR products, while the Illumina read 1 primers allow the sequencing of PhiX libraries. The sequence of custom read 1 primer is 5'-CATACGAGATCCGTAATCGGGAAGCT-GAAG-3' (SEQ ID NO: 10).

The sequencing reads were trimmed using Cutadapt (Martin et al. EMBnet. journal. 2011; 17:10-12) to remove the adapter sequences and OLR sequences. The chromosome 11 sequence was built to be used as a reference. We used BWA software (Li et al. Bioinformatics. 2009; 25:1754-1760) to align the sequencing reads to the reference. Sequencing reads correctly mapped to fused sequences, i.e., one part mapped to SNP 1 region and another part mapped to one of the nine other SNP regions.

As described above, the two haplotypes of the mother were then determined. The haplotypes carrying the C allele and the T allele at SNP 1 were denoted as Hap I and Hap II, respectively. For Hap I, we used a Python script to count the fragments with different combinations of the two alleles from two regions, denoted as allele contigs. For each pair of regions (SNPs), we collected the top two counted allele contigs and calculated their relative frequencies, which sum up to 100 percent. We set the frequency of the top allele contig >60% as a cutoff to identify it as a haplotype. If the frequency of the top allele contig <60%, the haplotype was indeterminable. In other embodiments, other percentages for example but not limited >65%, 70%, 80%, 90% can be used for the cutoff to identify the top allele contig as a haplotype in a sample. Similarly, we analyzed sequencing reads for Hap II.

FIG. 19 shows the phases determined by the digital fusion PCR method. The first column lists the SNP pairing of SNP 1 with another SNP. The alleles of the 10 SNPs of the haplotypes are listed in order. The second and third columns are for Hap I at SNP 1. The second column lists the frequency of the allele combination for SNP 1 and another SNP. The third column lists the determined alleles for Hap I. For each allele site, it may contain the base (allele) value, a dash for a site not covered by the pairing reads, or a cross for an undetermined site. The fourth and fifth columns are for Hap II at SNP 1. The fourth column lists the frequency of the allele combination for SNP 1 and another SNP. The fifth column lists the determined alleles for Hap II.

As shown FIG. 19, the fusion PCR method can physically phase two regions up to 50 kb (the distance from SNP 8 to SNP 1) apart accurately based on the cutoff frequency of 60%. For the determination of only Hap I, phasing was successful up to 75 kb (SNP 1). The accuracy of this method is determined by the quality and intactness of the DNA. A method that extracts DNA of high quality and longer size can improve the accuracy and lengthen the distance to be phased by this fusion PCR method.

D. Haplotyping Example Using Hemoglobin Subunit Beta Gene

We used the haplotyping of the variants of the Hemoglobin Subunit Beta (HBB) gene as an example to illustrate this haplotyping method for phasing multiple regions. HBB gene encodes the β subunit of hemoglobin. Mutations in the HBB gene may cause β-thalassemia, an autosomal recessive disease characterized by severe anemia. A person must carry two mutations from both parents to inherit the disease. Lo et al. have developed an approach to noninvasively identify if the fetus inherits two β-thalassemia mutations from both parents (Lo et al. Sci Transl Med. 2010; 2:61ra91). The authors obtained the paternal genotype and maternal haplotype. From maternal plasma DNA sequencing data, the paternal mutation inherited by the fetus can be found. To assess the fetal inheritance of maternal mutations, the authors used relative haplotype dosage (RHDO) analysis to see whether the fetus inherited the haplotype of the mother that contain the mutation. The RHDO analysis requires maternal haplotype information. Lo et al. deduced the maternal haplotype from a chorionic villus sample in this proof-of-principle study. Later, they used 10× genomics platform to direct phase the maternal haplotype (Hui et al. Clin Chem. 2017; 63:513-524). These haplotyping methods may be either complicated or expensive. Here, we demonstrated the potential applications of the digital fusion PCR method in noninvasively prenatal single-gene disease detection by phasing haplotypes on HBB gene.

To validate the accuracy of the digital fusion PCR method, we used genomic DNA of trios, including the father, mother, and fetus in a family. We recruited four trios from the Department of Chemical Pathology and Paediatrics, Prince of Wales Hospital (PWH), Hong Kong. The paternal buffy coat, maternal buffy coat, and fetal placenta tissues were then obtained. Using the method illustrated in FIGS. 15A, 15B, and 15C, we designed assays for phasing 20 SNPs. The 20 SNPs were split into two groups: group A includes SNP 1, 4, 6, 8, 10, 11, 13, 15, 17, and 20; and group B includes SNP 2, 3, 5, 7, 9, 12, 14, 16, 18, and 19. In other embodiments, other grouping arrangements can be applied, for example but not limited to SNP 1 to 10 as group A and SNP 11 to 20 as group B, and SNP 1 as group A and SNP 2 to 20 as group B. The inner primer sequences used are similar to those illustrated with FIG. 15B. The 5' end of the reverse primers for a region in Group A is complementary to the 5' end of the forward primers in Group B.

FIG. 20 shows primer sequences for SNPs in the HBB gene. The first column shows the region number for 20 SNPs in the HBB gene. The second column shows the SNP ID. The third column shows the sequence of the forward primer from 5' to 3'. The fourth column shows the sequence of the reverse primer from 5' to 3'. The reverse primer for each SNP in group A includes OLR1 (highlighted in yellow and underlined). OLR1 is complementary to OLR2 (highlighted in green and underlined) of the forward primers for each SNP in group B. The base "A" is highlighted in red and bolded and represents an additional base between the OLR and the priming sequence.

DNA extracted from paternal buffy coat, maternal buffy coat, or fetal placenta were distributed into droplets to carry out linking PCR using the BioRad Droplet Digital PCR system.

A PCR reaction was prepared for each sample in a volume of 20 μL, consisting of 3.2 ng of template DNA, 10 μL of 2× ddPCR Supermix for Probes (No dUTP) (Bio-Rad), a final concentration of 1 μmol/L of each of a pair of inner adapter primers, a final concentration of 40 nmol/L of each reverse primer in group A and forward primer in group B, and a final concentration of 50 nmol/L of each forward primer in group A and reverse primer in group B. The PCR reaction mix was then partitioned using the QX100/QX200 Droplet Digital PCR Generator (Bio-Rad). The thermal profile of the assay was the following: initiated at 95° C. for 10 minutes; followed by 50 cycles of 94° C. for 45 seconds, 59° C. for 1 minute, and 72° C. for 3 minutes; and a final incubation at 98° C. for 10 minutes. The fused PCR products were recovered from droplets and ligated to outer sequencing adapters using the protocol described herein. Indexed libraries were multiplexed and sequenced on Illumina MiSeq sequencing platform. The sequencing reads were trimmed and aligned to chromosome 11. A Python script was used to assemble the haplotypes of the 20 SNPs.

Figure 21A:
FIGS. 21A-21B illustrate phase assembly analysis according to embodiments of the present disclosure.
Figure 21B:
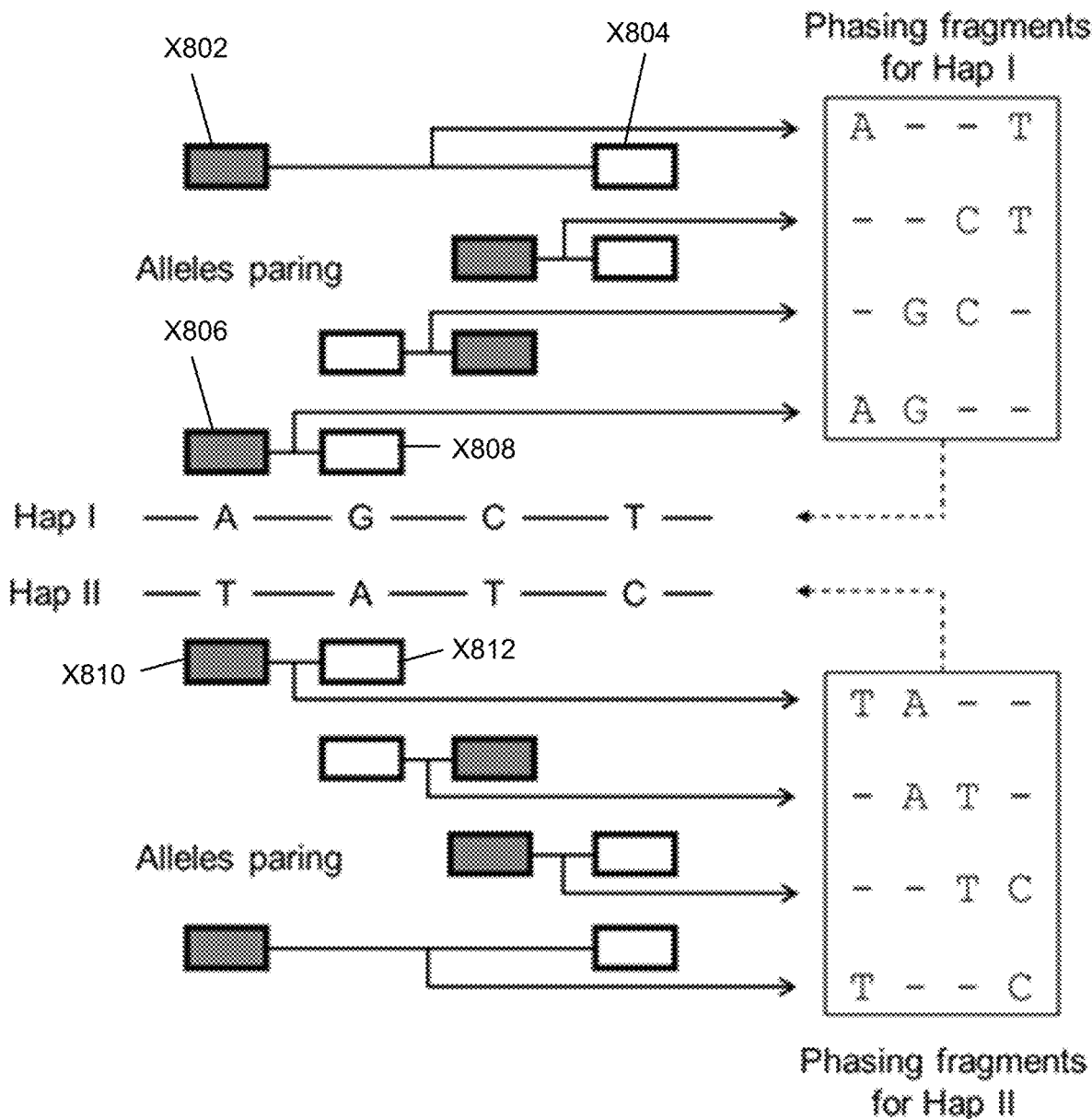

FIGS. 21A and 21B illustrate phase assembly analysis. In this example, the principle of phase assembly analysis is demonstrated by phasing four SNPs. FIG. 21A shows the four SNPs for phasing split into two groups: group A has SNP 1 and 3 (gray triangles), and SNP 2 and 4 as group B (white triangles).

FIG. 21B shows the determination of haplotypes from fused PCR products of two regions. From sequencing data, any allele from group A (gray boxes) may be linked to any allele from group B (white boxes). The two phased alleles in a fused product reveals part of the haplotypes. The two haplotypes may then be inferred using all the phased alleles.

For example, in a fused PCR product of SNP 1 and SNP 4, region X802 may be determined to have the A allele for SNP 1, and region X804 may be determined to have the T allele for SNP 4. In a fused PCR product of SNP 1 and SNP 2, region X806 may be determined to have the A allele for SNP 1, and region X808 may be determined to have the G allele for SNP 2. SNP 1, having the same allele A, then serves to link SNP 2 (allele G) and SNP 4 (allele T). A similar process may be used to determine SNP 3.

A fused product for one haplotype can be distinguished from the fused product for another haplotype by the alleles not matching. For example, region X806 shows allele A for SNP 1, while region X810 shows allele T for SNP 1. Additionally, region X808 shows allele G for SNP 2 and region X812 shows allele A for SNP 2. As a result, the fused product of region X806 and region X808 is determined to be a different haplotype than the fused product of region X810 and region X812.

FIG. 22 shows a table of haplotypes deduced by fusion PCR method for family trios. The first column of the table shows the individual for which the haplotypes are deduced by fusion PCR. Four families, with a father, mother, and fetus, are shown in the table. The second column shows the haplotype label. The remaining columns show the allele for the 20 SNPs.

The haplotypes of each individual were determined by the fusion PCR method. The haplotypes determined by this method completely matched the haplotype deduced from the genotypes of the family trio consisting of the father, mother, and the child. The matching of the deduced haplotypes from genotype analysis with the determination by fusion PCR confirms the accuracy of the fusion PCR method. For each family, the haplotype highlighted in blue represents the haplotype the father passed onto the child, and the haplotype highlighted in red represents the haplotype the mother passed onto the child. The parental haplotype passed onto the child is also denoted by an asterisk in the second column.

VII. Method

Figure 23:
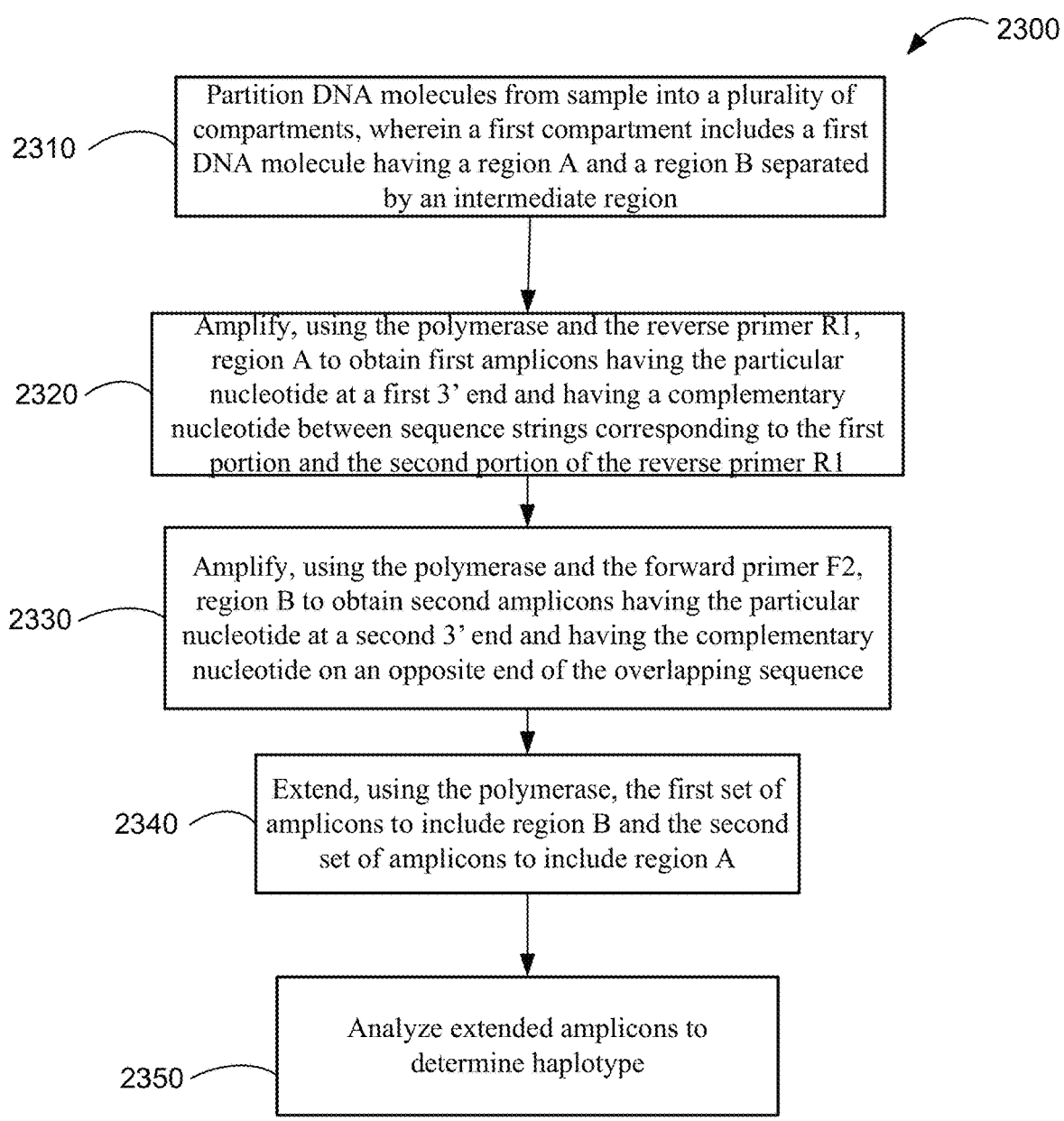
FIG. 23 is a flowchart illustrating a method for connecting separated regions of DNA molecules in a biological sample of a subject according to embodiments of the present disclosure.

FIG. 23 is a flowchart illustrating a method for connecting separated regions of DNA molecules in a biological sample of a subject according to embodiments of the present disclosure.

At block 2310, DNA molecules from the biological sample are partitioned into a plurality of compartments (e.g., droplets). The partitioning can be such that the compartments generally include only one DNA molecule at most. Some of the compartments may have less than one DNA molecule. As an example, the compartments can be droplets. As examples, there are existing commercially available devices that can automatically generate thousands of nanoliter-sized droplets in a short time, for example but not limited to BioRad QX200 Droplet Generator, Elveflow Droplet Generator Pack, and Micronit Microfluidic Droplet Generator. Various reagents (e.g., primers) can be added into the compartments. Other compartments include an Eppendorf tube, a well of a PCR plate, or any other container.

Of a set of compartments that include a DNA molecule, each compartment can include particular reagents. For example, a first compartment of a plurality of compartments can include: (1) a first DNA molecule having a region A and a region B separated by an intermediate region, (2) a polymerase having a bias for adding a particular nucleotide at an overhang position, (3) a reverse primer R1 having a first portion complementary to an ending sequence of region A, the reverse primer including a second portion having an overlapping sequence, and (4) a forward primer F2 having a first portion complementary to a starting sequence of region B, the forward primer including a complementary overlapping sequence that is complementary to the overlapping sequence. The compartment may also include a forward primer F1 at the start of region A and a reverse primer R2 at the ending of region B.

Primers hybridize to the 3' end of one strand for extending to the 3' end of the other strand. The forward primer hybridizes with one of the Crick or Watson strand at the 3' end for extending to the 3' end of the other strand. When the forward primer hybridizes with the Crick strand, the reverse primer hybridizes with the 3' end of the Watson strand for extending to the 3' end of the Crick strand. The starting sequence of a region is at the 5' end of the Watson strand. The ending sequence of a region is at the 3' end of the Watson strand. Similarly, when the forward primer hybridizes with the Watson strand, the reverse primer hybridizes with the 3' end of the Crick strand for extending to the 3' end of the Watson strand. The starting sequence of a region is at the 5' end of the Crick rand. The ending sequence of a region is at the 3' end of the Crick strand.

As examples, the intermediate region may have a length less than or equal to 100 kb, including 2.5 kb, 5 kb, 10 kb, 20 kb, 30 kb, 40 kb, 50 kb, 75 kb, or any range between these lengths.

The first DNA molecule can include regions as shown in FIG. 3A or other similar figures. FIG. 13A shows region A being exon 1 of the NUDT15 gene and region B being exon 3 of the NUDT15 gene.

As explained above, a polymerase can have a bias for adding a particular nucleotide (e.g., A) at an overhang position. A sticky end is an end of a double-stranded DNA that has at least one outermost nucleotide not hybridized to the other strand. Sticky ends are also called overhangs or jagged ends. An overhang position is a position that is not hybridized to the other strand, and may correspond to the first such position. The A 319 or 329 in FIG. 3C is an example. Other polymerases may have a bias for other nucleotides besides A, and embodiments can be used with such polymerases as well. In some embodiments, including those described below, the polymerase does not need to have a bias for adding a particular nucleotide.

As examples, the reverse primer R1 can correspond to those labeled as R5 in FIGS. 3A, 4A, and 5A, or labeled as R1 in FIGS. 8A, 9A, and 13A. As examples, the first portion can correspond to the priming sequence, e.g., 403 in FIG. 4B. As examples, the second portion having an overlapping sequence can correspond to OLR 310, 410, 510, and other similar portions described herein. The reverse primer R1 can include a particular nucleotide (e.g., A 409 or 509) between the first portion and the second portion. In some embodiments, the reverse primer R1 may not include the particular nucleotide when the method uses a polymerase that does not add an additional adenosine to the 3' end of the DNA strand it extends.

As examples, the forward primer F2 can correspond to those labeled as F6 in FIGS. 3A, 4A, and 5A, or labeled as F2 in FIGS. 8A, 9A, and 13A. As an example, the first portion can correspond to the priming sequence, e.g., 553 in FIG. 5B. As examples, the complementary overlapping sequence can be the first portion (e.g., corresponding to the start of region B), e.g., as shown by F6 in FIGS. 3A and 4A or F2 in FIG. 8A. Accordingly, the first portion of the forward primer can include the complementary overlapping sequence.

As another example, the complementary overlapping sequence can correspond a second portion of the forward primer F2, e.g., to OLR 550 in FIG. 5B and other similar portions described herein. Accordingly, the forward primer F2 can include a second portion having the complementary overlapping sequence. The forward primer F2 can include the particular nucleotide (e.g., A) between the first portion and the second portion, e.g., as depicted in FIG. 5B. In some embodiments, the forward primer F2 may not include the particular nucleotide if the method uses a polymerase that would not add an additional adenosine to the DNA strand it extends.

At block 2320, the polymerase and the reverse primer R1 are used to amplify region A to obtain a first set of amplicons having the particular nucleotide (e.g., A 319 in strand X) at a first 3' end and having a complementary nucleotide (e.g., T 513 in strand X) between sequence strings corresponding to the first portion and the second portion of the reverse primer R1. The complementary nucleotide is complementary to the particular nucleotide. One of the sequence strings can be part of the complementary overlapping sequence, e.g., OLR in FIG. 5C. In some embodiments, when the polymerase does not add an additional base (e.g., adenosine) to the DNA strand it extends, the additional nucleotides located at the 3' and 5' ends of the OLRs would not exist or be needed.

The complementary nucleotide may or may not be part of the first DNA molecule in the DNA molecule, e.g., as depicted in FIGS. 3A-3F (included) and FIGS. 4A-4C (not included). Accordingly, the complementary nucleotide in the first set of amplicons can be in the first DNA molecule (e.g., at an outermost ending position).

At block 2330, the polymerase and the forward primer F2 are used to amplify region B to obtain a second set of amplicons having the particular nucleotide (e.g., A 329 in strand Z of FIG. 3C) at a second 3' end and having the complementary nucleotide (e.g., T 563 in strand Z) on an opposite end of the overlapping sequence. In some embodiments, the second set of amplicons may not include the particular nucleotide and the complementary nucleotide.

At block 2340, the polymerase is used to extend the first set of amplicons to include region B and the second set of amplicons to include region A. In this manner, extended amplicons can be obtained that include region A and region B and exclude the intermediate region. A forward primer F1 and a reverse primer R2 can be used to amplify the extended amplicons.

The extension can be performed in the same compartment or as part of a separate assay. When performed in the same compartment and as described above, F1 and R2 may be at higher concentrations than F2 and R1 so that eventually most of the products would be the extended amplicons.

At block 2350, the extended amplicons are analyzed to determine haplotypes. Any number of suitable assays may be performed to analyze the extended amplicons. For example, sequencing, for example but not limited to using Illumina sequencing systems (e.g. HiSeq2500, NextSeq 550 and MiSeq), Pacific Biosystems sequencer and Ion Proton sequencing system, may be performed. As another example, allele-specific PCR may be performed to detect at least one allele in region A and at least one other allele in region B. Regardless of the specific technique, a first allele can be detected in the region A, and a second allele can be detected in the region B, thereby detecting that the first allele and the second allele are on a same haplotype.

An allele (e.g., the first allele in region A or the second allele in region B) may be detected by measuring an amount of the allele in the respective region. The amount may be a concentration, a percentage, a fraction, or a count. The amount may be compared to a cutoff value. If the amount is greater than the cutoff value, the allele may be determined to be detected. The cutoff value may include be 50%, 60%, 70%, 80%, 90%, 95%, or the equivalent fractions.

In some embodiments, the extended amplicons may be analyzed to determine the presence of an amplification or a deletion. The extended amplicons may be sequenced to obtain sequencing reads. The sequencing reads may be aligned to a reference genome. Amplifications and deletions may be identified from misalignment between the sequencing reads and the reference genome.

In some embodiments, a molecule can be added to forward primer F2 and a reverse primer R1 so that unlinked (unextended) amplicons can be captured and removed.

A. Primers for Amplifying Fused Products

The method may include using forward primer Fz and reverse primer Rz to amplify fused products. Examples of forward primer Fz and reverse primer Rz include F3 and R3 in FIGS. 6, R4 and F4 in FIG. 10A, or Fz or Rz in FIG. 15B). Forward primer F1 may include a second portion that is not the first portion. The first compartment may further include the forward primer Fz having a first portion identical to the second portion of the forward primer F1. The forward primer Fz may also have a second portion. The forward primer Fz may include the complementary nucleotide. The reverse primer R2 may include a second portion that is not the first portion. The first compartment may also include reverse primer Rz having a first portion identical to the second portion of the reverse primer R2. Reverse primer Rz may have a second portion. The reverse primer Rz may have the complementary nucleotide.

Fused products formed using the forward primer F1 and the reverse primer R2 may be amplified using the forward primer Fz and the reverse primer Rz. The extended amplicons formed using the forward primer F1 and the reverse primer R2 may be first extended amplicons. The first extended amplicons may include the second portion of the forward primer F1 and the second portion of the reverse primer R2. The method may include amplifying, using the polymerase, the forward primer Fz and the reverse primer Rz, the first extended amplicons to obtain second extended amplicons. Each second extended amplicon may include the second portion of the forward primer Fz and the second portion of the reverse primer Rz.

In embodiments using the forward primer Fz and the reverse primer Rz to amplify fused products, the polymerase may not have a bias for adding a particular nucleotide. Accordingly, these forward and the reverse primers (Fz and Rz) may not include a nucleotide complementary to the particular nucleotide at the end of an overlapping sequence.

B. Fusing Three Regions

In some embodiments, methods may be used to fuse together three regions of the first DNA molecule. For example, three regions may be fused as in FIG. 8A, 8B, 10A, or 10B. The figures label the regions as region 1, region 2, and region 3, but embodiments are described that refer to regions A, region B, and region C. The naming of regions by number or letter does not affect the methods. The regions may be region A (e.g., labeled as region 1 in some figures), region B (e.g., labeled as region 2 in some figures), and region C (e.g., labeled as region 3 in some figures). The intermediate region between region A and region B may be a first intermediate region. The region C may be separated from the region B by a second intermediate region. The overlapping sequence of the second portion of the reverse primer R1 may be a first overlapping sequence. The complementary overlapping sequence of the forward primer F2 may be a first complementary overlapping sequence.

The first compartment may also include a reverse primer R2 having a first portion complementary to an ending sequence of region B. The reverse primer R2 may include a second portion having a second overlapping sequence. The first compartment may also include a forward primer F3 having a first portion complementary to a starting sequence of the region C. The forward primer F3 may include a second complementary overlapping sequence that is complementary to the second overlapping sequence. The second complementary overlapping sequence may be in the first portion of the forward primer F3 or in a second portion of the forward primer F3.

The method may include amplifying, using the polymerase and the forward primer F3, region C to obtain a third set of amplicons having the particular nucleotide at a third 3' end and having the complementary nucleotide on the opposite end of the second overlapping sequence. Amplifying the region B to obtain the second set of amplicons may include using the reverse primer R2.

The method may further include extending, using the polymerase, three sets of amplicons. The first extended amplicons (having the region A and the region B) may be extended to include the region C. The third set of amplicons may be extended to include the region A and the region B. The result of the extensions may be second extended amplicons that include the region A, the region B, and the region C, and excluding the first intermediate region and the second intermediate region.

Extending the first extended amplicons to include the region C may include hybridizing to the second overlapping sequence toward a fourth 3' end (at the ending sequence of region C). Extending the third set of amplicons to include the region A and the region B may include hybridizing to the second complementary overlapping sequence toward the second 3' end (at the starting sequence of region B).

In embodiments fusing three or more regions, the polymerase may not have a bias for adding a particular nucleotide. Similarly, the reverse primers may not include the particular nucleotide at the end of an overlapping sequence, and the forward primers may not include a nucleotide complementary to the particular nucleotide at the end of the complementary overlapping sequence.

C. Fusing Regions from Different Groups

The method may also include forming fused PCR products that do not include all regions in one fused product. For example, three regions may be fused, but the regions may be fused into two fused products, each with two regions (e.g., FIG. 14). For example, the first DNA molecule may have a region D (e.g., region 4 in FIG. 14). Region D may be separated from the region A (e.g., region 1 in FIG. 14) by a second intermediate region. The first compartment may further include a forward primer F4 having a first portion complementary to a starting sequence of the region D. The forward primer F4 may include a second portion having the complementary overlapping sequence, which is also in the forward primer F2. The first compartment may also include a reverse primer R4 having a first portion complementary to the ending sequence of the region D.

The method may include amplifying, using the polymerase and the forward primer F4, the region D to obtain a third set of amplicons. The third set of amplicons may have the particular nucleotide at a third 3' end and having the complementary nucleotide on the opposite end of the overlapping sequence. Using the polymerase, the first set of amplicons may be extended to include the region D. Using the polymerase, the third set of amplicons may be extended to include the region A. Second extended amplicons that include the region A and the region D may be obtained. The second extended amplicons may exclude the second intermediate region. The first extended amplicons are the extended amplicons that include the region A and the region B (e.g., region 2 in FIG. 14).

In some embodiments, methods may include linking regions from three different groups, such as in FIG. 15A. Regions are described by letters but can have an In an example of linking 4 regions, region A is a region in the first group (e.g., region 1 in FIG. 15A). Region B (e.g., region 2 in the illustration) and region D (e.g., region 5 in the illustration) are regions in the second group. Region C (e.g., region 3 in the illustration) is a region in the third group. Region A (region 1) may link with either region B (region 2) or region D (region 5). Region B (region 2) or region D (region 5) may link with region C (region 3). The complementary sequence in forward primer F2 may be a first complementary overlapping sequence. The overlapping sequence in reverse primer R1 may be a first overlapping sequence. The first compartment may further include a reverse primer R2 having a first portion complementary to an ending sequence of the region B (region 2). The reverse primer R2 may include a second portion having a second overlapping sequence. The first compartment may also include a reverse primer R4 having a first portion complementary to an ending sequence of the region D (region 5). The reverse primer R4 may include a second portion having the second overlapping sequence. The first compartment may further include a forward primer F3 having a first portion complementary to a starting sequence of a region C (region 3) of the first DNA molecule. The region C (region 3) may be separated from the region B (region 2) by a third intermediate region. The first intermediate region or the second intermediate region may include the region C (region 3). The forward primer F3 may include a second portion having the second complementary overlapping sequence.

Amplifying the region B (region 2) may include using the reverse primer R2. Amplifying the region D (region 5) may include using the reverse primer R4, The method may further include amplifying, using the polymerase and the forward primer F3, the region C (region 3) to obtain a fourth set of amplicons. The method may further include extending, using the polymerase, the second extended amplicons to include the region C (region 3), thereby obtaining third extended amplicons that include the region A (region 1), the region D (region 5), and the region C (region 3). The method may also include extending, using the polymerase, the first extended amplicons to include the region C (region 3), thereby obtaining fourth extended amplicons that include the region A (region 1), the region B (region 2), and the region C (region 3).

In some embodiments, two regions can be linked, selecting a first region from a first group and a second region from a second group, such as in FIG. 14A. For example, the first group may include the region A (i.e. region 1 in the illustration) and the region C (i.e. region 3 in the illustration). The second group may include the region B (i.e. region 2 in the illustration) and the region D (i.e. region 4 in the illustration). As explained above, region A (region 1) and region B (region 2) can be fused, and region A (region 1) and region D (region 4) can be fused. Additionally, region C (region 3) and region B (region 2) can be fused and region C (region 3) and region D (region 4) can be fused. The first compartment may include a reverse primer R3 having a first portion complementary to an ending sequence of a region C (region 3) of the first DNA molecule. The region C (region 3) may be separated from the region B (region 2) by a third intermediate region. The region C (region 3) may be separated from the region D (region 4) by a fourth intermediate region. The reverse primer R3 may include a second portion having the overlapping sequence, which is the same overlapping sequence in reverse primer R1.

The method may include amplifying, using the polymerase and the reverse primer R3, the region C (region 3) to obtain a fourth set of amplicons having the particular nucleotide at a fourth 3' end and having the complementary nucleotide on the opposite end of the overlapping sequence. The method may also include extending, using the polymerase, the fourth set of amplicons to include the region B (region 2) and the second set of amplicons to include the region C (region 3), thereby obtaining third extended amplicons that include the region C (region 3) and the region B (region 2) and exclude the third intermediate region. The method may further include extending, using the polymerase, the fourth set of amplicons to include the region D (region 4) and the third set of amplicons to include the region C (region 3), thereby obtaining fourth extended amplicons that include the region C (region 3) and the region D (region 4) and exclude the fourth intermediate region.

In embodiments fusing various combinations of at least two regions in the same compartment, the polymerase may not have a bias for adding a particular nucleotide. Accordingly, the reverse primers may not include the particular nucleotide at the end of an overlapping sequence, and the forward primers may not include a nucleotide complementary to the particular nucleotide at the end of the complementary overlapping sequence. Forward and reverse primers Fz and Rz may not include the particular nucleotide at the end of an overlapping sequence.

Phase assembly analysis, such as what was described with FIG. 21B, may be performed on the first extended amplicons and the second extended amplicons. A first allele may be detected in the region A (e.g., region 1 in FIG. 21B) in the first extended amplicons. A second allele may be detected in the region B (e.g., region 2 in FIG. 21B) in the first extended amplicons. The first allele may also be detected in the region A in the second extended amplicons. A third allele may be detected in the region D (e.g., region 4 in FIG. 21B) in the second extended amplicons. As a result of the first allele being detected in in region A in both extended amplicons, the first allele in the region A, the second allele in the region B, and the third allele in the region D may be detected on a same haplotype.

In some embodiments, the first allele may not be detected in the region A in the second extended amplicons. Instead a fourth allele may be detected in the region A in the second extended amplicons. In those instances, the third allele in the region D may be determined to not be on the same haplotype as the first allele in region A.

The above process can be repeated for each of the plurality of compartments to determine a haplotype in each of the compartments that include a DNA molecule.

VIII. Kits

Embodiments may include kits for connecting separate regions of DNA molecules in a biological sample of a subject. The kit may include a polymerase having a bias for adding a particular nucleotide at an overhang position. In some embodiments, the polymerase may not include a bias for adding a particular nucleotide at an overhang position. The embodiments include kits for using a forward primer Fz and a reverse primer Rz to amplify fused products, kits for fusing three or more regions, and kits for fusing various combinations of at least two regions in the same compartment, similar to methods described above.

The kit may also include a reverse primer R1 having a first portion complementary to an ending sequence of a region A of a first DNA molecule. The reverse primer R1 may include a second portion having an overlapping sequence. The particular nucleotide for which the polymerase has a bias for adding may be between the first portion and the second portion.

The kit may further include a forward primer F2 having a first portion complementary to a starting sequence of a region B of the first DNA molecule. Region B may be separated from Region A by an intermediate region. The forward primer F2 may include a complementary overlapping sequence that is complementary to the overlapping sequence of reverse primer R1. The complementary overlapping sequence may be in a second portion of forward primer F2, where the second portion is not the first portion. In some embodiments the first portion of forward primer F2 may include the complementary overlapping sequence.

The kit may also include a forward primer F1 having a first portion complementary to a starting sequence of region A. Forward primer F1 may include a second portion that is not the first portion.

The kit may further include a reverse primer R2 having a first portion complementary to an ending sequence of region B. Reverse primer R may include a second portion that is not the first portion.

The kit may include a forward primer Fz and a reverse primer Rz, both of which may be used to amplify fused products. Forward primer Fz may have a first portion identical to the second portion of forward primer F1. Reverse primer Rz may have a first portion identical to the second portion of reverse primer R2. Forward primer Fz may include a nucleotide complementary to the particular nucleotide. Reverse primer Rz may include a nucleotide complementary to the particular nucleotide.

The ratio of forward primer Fz to forward primer F1 or any primer other than reverse primer Rz may be at least 5:1. In some embodiments, the ratio may be at least 10:1, 20:1, 50:1, 75:1, 100:1, 200:1, 500:1, 1000:1, 2000:1, 5000:1, 10000:1, 20000:1, 50000:1, or 100000:1. The ratio of reverse primer Rz to reverse primer R2 or any primer other than forward primer Fz may be at least 5:1, 10:1, 20:1, 50:1, 75:1, 100:1, 200:1, 500:1, 1000:1, 2000:1, 5000:1, 10000:1, 20000:1, 50000:1, or 100000:1.

Forward primer Fz and reverse primer Rz may each include a second portion. The second portion may be designed for sequencing. For example, the second portion may be a sample index or an adaptor sequence for a particular sequencing platform.

In some embodiments, the kit may further include a reverse primer R2 having a first portion complementary to an ending sequence of region B. Reverse primer R2 may include a second portion having a second overlapping sequence. The kit may also include a forward primer F3 having a first portion complementary to a starting sequence of a region C of the first DNA molecule. Region C may be separate from region B by a second intermediate region. Forward primer F3 may include a second complementary overlapping sequence that is complementary to the second overlapping sequence in reverse primer R2. The second overlapping sequence may not be the overlapping sequence in reverse primer R1. In some embodiments, the second overlapping sequence may be the overlapping sequence in reverse primer R1.

In some embodiments, the kit may include a reverse primer R3. Reverse primer R3 may have a first portion complementary to an ending sequence of region C. Reverse primer R3 may have a second portion that is not the first portion. With a region C, reverse primer Rz may have a first portion that is identical to the second portion of reverse primer R3.

The overlapping sequences in the primers may be at least 12 bases, including 12 to 15, 15 to 20, 20 to 25, or more than 25 bases. The portions of primers complementary to a sequence of a region may be at least 12 bases, including 12 to 15, 15 to 20, 20 to 25, or more than 25 bases.

The portions of the primers complementary to a sequence of the region may be at the 3' end of the primer. The portions of the primers that are overlapping sequences or complementary to overlapping sequences may be at the 5' end of the primer. Forward primer Fz and reverse primer Rz may have the portions that are identical to forward primer F1 and reverse primer R2 may be at the 3' end of forward primer Fz and reverse primer Rz.

The kit may include the first DNA molecule. The kit may include reagents for PCR, microfluidic cartilage for generating the individual compartments for PCR, and the primers for the fusion reactions.

IX. Example Systems

Figure 24:
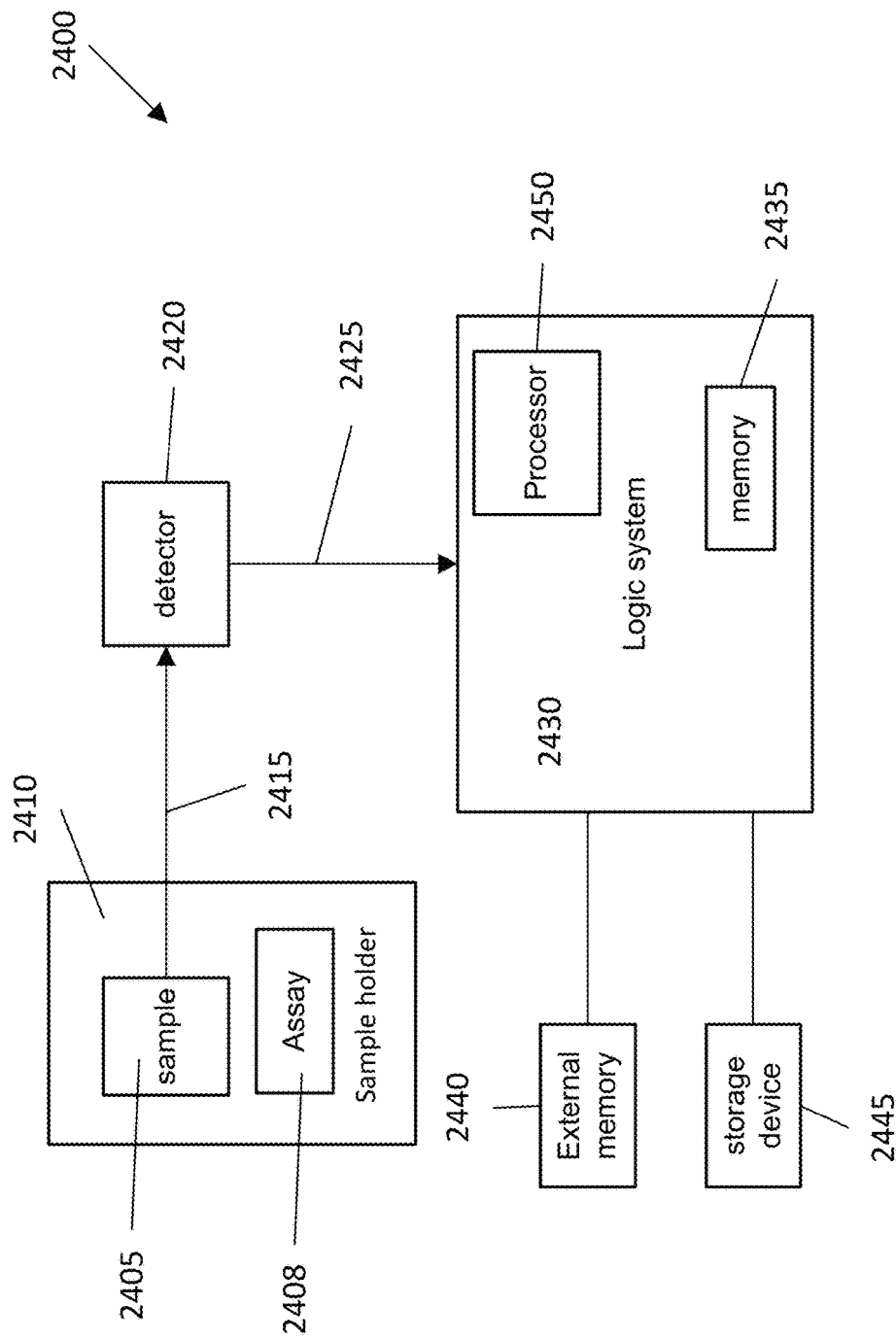
FIG. 24 illustrates a measurement system according to an embodiment of the present disclosure.

FIG. 24 illustrates a measurement system 2400 according to an embodiment of the present invention. The system as shown includes a sample 2405, such as cell-free DNA molecules within a sample holder 2410, where sample 2405 can be contacted with an assay 2408 to provide a signal of a physical characteristic 2415. An example of a sample holder can be a flow cell that includes probes and/or primers of an assay or a tube through which a droplet moves (with the droplet including the assay). Physical characteristic 2415 (e.g., a fluorescence intensity, a voltage, or a current), from the sample is detected by detector 2420. Detector 2420 can take a measurement at intervals (e.g., periodic intervals) to obtain data points that make up a data signal. In one embodiment, an analog-to-digital converter converts an analog signal from the detector into digital form at a plurality of times. Sample holder 2410 and detector 2420 can form an assay device, e.g., a sequencing device that performs sequencing according to embodiments described herein. A data signal 2425 is sent from detector 2420 to logic system 2430. Data signal 2425 may be stored in a local memory 2435, an external memory 2440, or a storage device 2445.

Logic system 2430 may be, or may include, a computer system, ASIC, microprocessor, etc. It may also include or be coupled with a display (e.g., monitor, LED display, etc.) and a user input device (e.g., mouse, keyboard, buttons, etc.). Logic system 2430 and the other components may be part of a stand-alone or network connected computer system, or they may be directly attached to or incorporated in a device (e.g., a sequencing device) that includes detector 2420 and/or sample holder 2410. Logic system 2430 may also include software that executes in a processor 2450. Logic system 2430 may include a computer readable medium storing instructions for controlling system 2400 to perform any of the methods described herein. For example, logic system 2430 can provide commands to a system that includes sample holder 2410 such that sequencing or other physical operations are performed. Such physical operations can be performed in a particular order, e.g., with reagents being added and removed in a particular order. Such physical operations may be performed by a robotics system, e.g., including a robotic arm, as may be used to obtain a sample and perform an assay.

Figure 25:
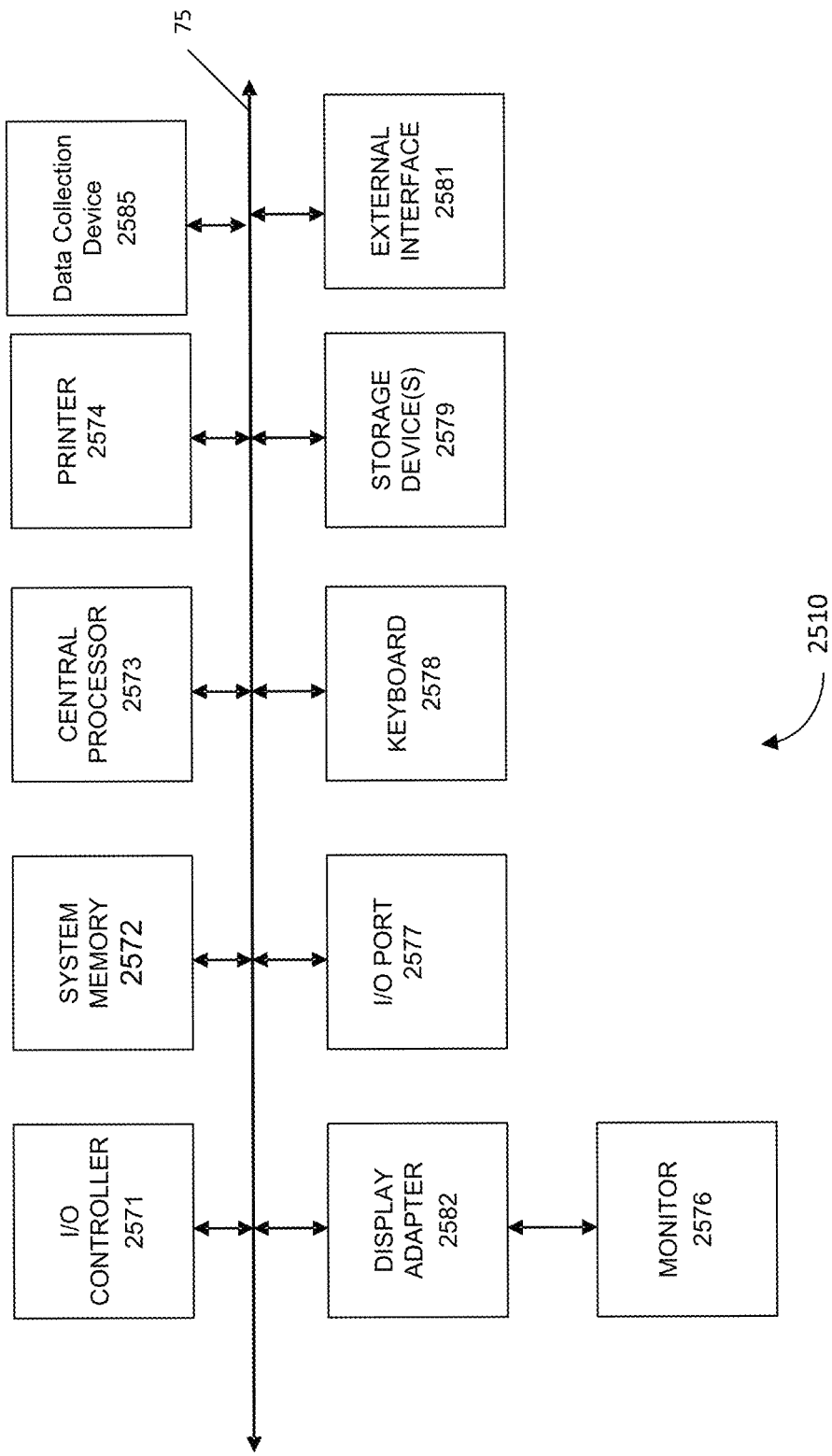
FIG. 25 shows a block diagram of an example computer system usable with systems and methods according to embodiments of the present disclosure.

Any of the computer systems mentioned herein may utilize any suitable number of subsystems. Examples of such subsystems are shown in FIG. 25 in computer system 2510. In some embodiments, a computer system includes a single computer apparatus, where the subsystems can be the components of the computer apparatus. In other embodiments, a computer system can include multiple computer apparatuses, each being a subsystem, with internal components. A computer system can include desktop and laptop computers, tablets, mobile phones and other mobile devices.

The subsystems shown in FIG. 25 are interconnected via a system bus 2575. Additional subsystems such as a printer 2574, keyboard 2578, storage device(s) 2579, monitor 2576 (e.g., a display screen, such as an LED), which is coupled to display adapter 2582, and others are shown. Peripherals and input/output (I/O) devices, which couple to I/O controller 71, can be connected to the computer system by any number of means known in the art such as input/output (I/O) port 2577 (e.g., USB, FireWire®). For example, I/O port 2577 or external interface 2581 (e.g. Ethernet, Wi-Fi, etc.) can be used to connect computer system 2510 to a wide area network such as the Internet, a mouse input device, or a scanner. The interconnection via system bus 2575 allows the central processor 2573 to communicate with each subsystem and to control the execution of a plurality of instructions from system memory 2572 or the storage device(s) 2579 (e.g., a fixed disk, such as a hard drive, or optical disk), as well as the exchange of information between subsystems. The system memory 2572 and/or the storage device(s) 2579 may embody a computer readable medium. Another subsystem is a data collection device 2585, such as a camera, microphone, accelerometer, and the like. Any of the data mentioned herein can be output from one component to another component and can be output to the user.

A computer system can include a plurality of the same components or subsystems, e.g., connected together by external interface 2581, by an internal interface, or via removable storage devices that can be connected and removed from one component to another component. In some embodiments, computer systems, subsystem, or apparatuses can communicate over a network. In such instances, one computer can be considered a client and another computer a server, where each can be part of a same computer system. A client and a server can each include multiple systems, subsystems, or components.

Aspects of embodiments can be implemented in the form of control logic using hardware circuitry (e.g. an application specific integrated circuit or field programmable gate array) and/or using computer software with a generally programmable processor in a modular or integrated manner. As used herein, a processor can include a single-core processor, multi-core processor on a same integrated chip, or multiple processing units on a single circuit board or networked, as well as dedicated hardware. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C, C++, C#, Objective-C, Swift, or scripting language such as Perl or Python using, for example, conventional or object-oriented techniques. The software code may be stored as a series of instructions or commands on a computer readable medium for storage and/or transmission. A suitable non-transitory computer readable medium can include random access memory (RAM), a read only memory (ROM), a magnetic medium such as a hard-drive or a floppy disk, or an optical medium such as a compact disk (CD) or DVD (digital versatile disk) or Blu-ray disk, flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Any of the methods described herein may be totally or partially performed with a computer system including one or more processors, which can be configured to perform the steps. Thus, embodiments can be directed to computer systems configured to perform the steps of any of the methods described herein, potentially with different components performing a respective step or a respective group of steps. Although presented as numbered steps, steps of methods herein can be performed at a same time or at different times or in a different order. Additionally, portions of these steps may be used with portions of other steps from other methods. Also, all or portions of a step may be optional. Additionally, any of the steps of any of the methods can be performed with modules, units, circuits, or other means of a system for performing these steps.

The specific details of particular embodiments may be combined in any suitable manner without departing from the spirit and scope of embodiments of the invention. However, other embodiments of the invention may be directed to specific embodiments relating to each individual aspect, or specific combinations of these individual aspects.

The above description of example embodiments of the present disclosure has been presented for the purposes of illustration and description. It is not intended to be exhaustive or to limit the disclosure to the precise form described, and many modifications and variations are possible in light of the teaching above.

A recitation of "a", "an" or "the" is intended to mean "one or more" unless specifically indicated to the contrary. The use of "or" is intended to mean an "inclusive or," and not an "exclusive or" unless specifically indicated to the contrary. Reference to a "first" component does not necessarily require that a second component be provided. Moreover, reference to a "first" or a "second" component does not limit the referenced component to a particular location unless expressly stated. The term "based on" is intended to mean "based at least in part on."

All patents, patent applications, publications, and descriptions mentioned herein are incorporated by reference in their entirety for all purposes. None is admitted to be prior art.

What is claimed is:

1. A method for connecting separated regions of DNA molecules in a biological sample of a subject, the method comprising:
   partitioning a plurality of DNA molecules from the biological sample into a plurality of compartments, wherein a first compartment of the plurality of compartments includes:
      a first DNA molecule having a region A and a region B separated by an intermediate region,
      a polymerase having a bias for adding a particular nucleotide at an overhang position,
      a reverse primer R1 having a first portion complementary to an ending sequence of the region A, the reverse primer R1 including a second portion having an overlapping sequence, and
      a forward primer F2 having a first portion complementary to a starting sequence of the region B, the forward primer F2 including a complementary overlapping sequence that is complementary to the overlapping sequence;
   amplifying, using the polymerase and the reverse primer R1, the region A to obtain a first set of amplicons having the particular nucleotide at a first 3' end and having a complementary nucleotide between sequence strings corresponding to the first portion and the second portion of the reverse primer R1, the complementary nucleotide being complementary to the particular nucleotide;
   amplifying, using the polymerase and the forward primer F2, the region B to obtain a second set of amplicons having the particular nucleotide at a second 3' end and having the complementary nucleotide on an opposite end of the overlapping sequence; and
   extending, using the polymerase, the first set of amplicons to include the region B and the second set of amplicons to include the region A, thereby obtaining extended amplicons that include the region A and the region B and exclude the intermediate region.

2. The method of claim 1, wherein the complementary nucleotide in the first set of amplicons is in the first DNA molecule.

3. The method of claim 1, wherein the reverse primer R1 includes the particular nucleotide between the first portion and the second portion.

4. The method of claim 1, wherein the compartments are droplets.

5. The method of claim 1, further comprising:
   using a forward primer F1 and a reverse primer R2 to amplify the extended amplicons.

6. The method of claim 1, further comprising:
  detecting a first allele in the region A and a second allele in the region B, thereby detecting that the first allele and the second allele are on a same haplotype.

7. The method of claim 6, wherein detecting the first allele in the region A comprises:
  measuring an amount of the first allele in the region A, and comparing the amount to a cutoff value.

8. The method of claim 1, wherein the biological sample is diluted such that on average only one DNA molecule is in a compartment.

9. The method of claim 1, further comprising:
  repeating the method for other compartments to determine the haplotype of other DNA molecules in the other compartments.

10. The method of claim 1, wherein:
  the first compartment further comprises:
    a forward primer F1 having a first portion complementary to a starting sequence of the region A and having a second portion,
    a reverse primer R2 having a first portion complementary to an ending sequence of the region B and having a second portion,
    a forward primer Fz having a first portion identical to the second portion of the forward primer F1 and having a second portion, and
    a reverse primer Rz having a first portion identical to the second portion of the reverse primer R2 and having a second portion,
  the extended amplicons are first extended amplicons, and
  each first extended amplicon includes the second portion of the forward primer F1 and the second portion of the reverse primer R2,
  the method further comprising:
    amplifying the first extended amplicons to obtain second extended amplicons using the polymerase, the forward primer Fz, and the reverse primer Rz, wherein each second extended amplicon includes the second portion of the forward primer Fz and the second portion of the reverse primer Rz.

11. The method of claim 10, wherein:
  the forward primer Fz comprises a complementary nucleotide, the complementary nucleotide being complementary to the particular nucleotide, and
  the reverse primer Rz comprises the complementary nucleotide.

12. The method of claim 1, wherein:
  the overlapping sequence is a first overlapping sequence,
  the complementary overlapping sequence is a first complementary overlapping sequence,
  the intermediate region is a first intermediate region,
  the extended amplicons are first extended amplicons; and
  the first compartment further includes:
    a reverse primer R2 having a first portion complementary to an ending sequence of the region B, the reverse primer R2 including a second portion having a second overlapping sequence, and a forward primer F3 having a first portion complementary to a starting sequence of a region C of the first DNA molecule, the region C separated from the region B by a second intermediate region, the forward primer F3 including a second complementary overlapping sequence that is complementary to the second overlapping sequence, and
  amplifying the region B to obtain the second set of amplicons comprises using the reverse primer R2,
  the method further comprising:
    amplifying, using the polymerase and the forward primer F3, region C to obtain a third set of amplicons having the particular nucleotide at a third 3' end and having the complementary nucleotide on the opposite end of the second overlapping sequence,
    extending, using the polymerase:
      the first extended amplicons to include the region C, and
      the third set of amplicons to include the region A and the region B,
      thereby obtaining second extended amplicons that include the region A, the region B, and the region C and exclude the first intermediate region and the second intermediate region.

13. The method of claim 12, wherein the forward primer F3 includes a second portion having the second complementary overlapping sequence.

14. The method of claim 12, wherein the first portion of the forward primer F3 includes second complementary overlapping sequence.

15. The method of claim 12, wherein:
  extending the first extended amplicons to include the region C comprises hybridizing to the second overlapping sequence toward a fourth 3' end.

16. The method of claim 12, wherein:
  extending the third set of amplicons to include the region A and the region B comprises hybridizing to the second complementary overlapping sequence toward the second 3' end.

17. The method of claim 1, wherein the first portion of the forward primer F2 includes the complementary overlapping sequence.

18. The method of claim 1, wherein the forward primer F2 includes a second portion having the complementary overlapping sequence.

19. The method of claim 18, wherein the forward primer F2 includes the particular nucleotide between the first portion and the second portion.

20. The method of claim 18, wherein:
  the intermediate region is a first intermediate region,
  the extended amplicons are first extended amplicons, and
  the first compartment further includes:
    a forward primer F4 having a first portion complementary to a starting sequence of a region D of the first DNA molecule, the region D separated from the region A by a second intermediate region, the forward primer F4 including a second portion having the complementary overlapping sequence,
  the method further comprising:
    amplifying, using the polymerase and the forward primer F4, the region D to obtain a third set of amplicons having the particular nucleotide at a third 3' end and having the complementary nucleotide on the opposite end of the overlapping sequence, and
    extending, using the polymerase, the first set of amplicons to include the region D and the third set of amplicons to include the region A, thereby obtaining second extended amplicons that include the region A and the region D and exclude the second intermediate region.

21. The method of claim 20, wherein:
  the first compartment further includes:
    a reverse primer R3 having a first portion complementary to an ending sequence of a region C of the first DNA molecule, the region C separated from the region B by a third intermediate region, the region C separated from the region D by a fourth intermediate region, the reverse primer R3 including a second portion having the overlapping sequence, the method further comprising:
amplifying, using the polymerase and the reverse primer R3, the region C to obtain a fourth set of amplicons having the particular nucleotide at a fourth 3' end and having the complementary nucleotide on the opposite end of the overlapping sequence, extending, using the polymerase, the fourth set of amplicons to include the region B and the second set of amplicons to include the region C, thereby obtaining third extended amplicons that include the region C and the region B and exclude the third intermediate region, and extending, using the polymerase, the fourth set of amplicons to include the region D and the third set of amplicons to include the region C, thereby obtaining fourth extended amplicons that include the region C and the region D and exclude the fourth intermediate region.

22. The method of claim 20, further comprising:
detecting a first allele in the region A in the first extended amplicons,
detecting a second allele in the region B in the first extended amplicons,
detecting the first allele in the region A in the second extended amplicons, and
detecting a third allele in the region D in the second extended amplicons,
thereby detecting the first allele in the region A, the second allele in the region B, and the third allele in the region D are on a same haplotype.

23. The method of claim 20, wherein:
the complementary overlapping sequence is a first complementary overlapping sequence,
the overlapping sequence is a first overlapping sequence,
the first compartment further includes:
a reverse primer R2 having a first portion complementary to an ending sequence of the region B, the reverse primer R2 including a second portion having a second overlapping sequence,
a reverse primer R4 having a first portion complementary to an ending sequence of the region D, the reverse primer R4 including a second portion having the second overlapping sequence, and
a forward primer F3 having a first portion complementary to a starting sequence of a region C of the first DNA molecule, the region C separated from the region B by a third intermediate region, the forward primer F3 including a second portion having the second complementary overlapping sequence,
amplifying the region B comprises using the reverse primer R2, and
amplifying the region D comprises using the reverse primer R4,
the method further comprising:
amplifying, using the polymerase and the forward primer F3, the region C to obtain a fourth set of amplicons,
extending, using the polymerase, the second extended amplicons to include the region C, thereby obtaining third extended amplicons that include the region A, the region D, and the region C, and
extending, using the polymerase, the first extended amplicons to include the region C, thereby obtaining fourth extended amplicons that include the region A, the region B, and the region C.

24. A method for connecting separated regions of DNA molecules in a biological sample of a subject, the method comprising:
partitioning a plurality of DNA molecules from the biological sample into a plurality of compartments, wherein a first compartment of the plurality of compartments includes:
a first DNA molecule having a region A and a region B separated by a first intermediate region,
a polymerase,
a reverse primer R1 having a first portion complementary to an ending sequence of the region A, the reverse primer R1 including a second portion having a first overlapping sequence,
a forward primer F2 having a first portion complementary to a starting sequence of the region B, the forward primer F2 including a second portion having a first complementary overlapping sequence that is complementary to the first overlapping sequence,
a forward primer F4 having a first portion complementary to a starting sequence of a region D of the first DNA molecule, the region D separated from the region A by a second intermediate region, the forward primer F4 including a second portion having the first complementary overlapping sequence,
a reverse primer R2 having a first portion complementary to an ending sequence of the region B, the reverse primer R2 including a second portion having a second overlapping sequence,
a reverse primer R4 having a first portion complementary to an ending sequence of the region D, the reverse primer R4 including a second portion having the second overlapping sequence, and
a forward primer F3 having a first portion complementary to a starting sequence of a region C of the first DNA molecule, the region C separated from the region B by a third intermediate region, the forward primer F3 including a second portion having the second complementary overlapping sequence;
amplifying, using the polymerase and the reverse primer R1, the region A to obtain a first set of amplicons;
amplifying, using the polymerase, the forward primer F2, and the reverse primer R2, the region B to obtain a second set of amplicons;
amplifying, using the polymerase, the forward primer F4, and the reverse primer R4, the region D to obtain a third set of amplicons;
amplifying, using the polymerase and the forward primer F3, the region C to obtain a fourth set of amplicons;
extending, using the polymerase, the first set of amplicons to include the region B and the second set of amplicons to include the region A, thereby obtaining first extended amplicons that include the region A and the region B and exclude the first intermediate region;
extending, using the polymerase, the first set of amplicons to include the region D and the third set of amplicons to include the region A, thereby obtaining second extended amplicons that include the region A and the region D and exclude the second intermediate region; and
extending, using the polymerase, the second extended amplicons to include the region C, thereby obtaining third extended amplicons that include the region A, the region D, and the region C, and extending, using the polymerase, the first extended amplicons to include the region C, thereby obtaining fourth extended amplicons that include the region A, the region B, and the region C.

25. The method of claim 24, further comprising:

detecting a first allele in the region A in the first extended amplicons, detecting a second allele in the region B in the first extended amplicons, detecting the first allele in the region A in the second extended amplicons, and detecting a third allele in the region D in the second extended amplicons, thereby detecting the first allele in the region A, the second allele in the region B, and the third allele in the region D are on a same haplotype.

26. The method of claim 24, wherein the polymerase has a bias for adding a particular nucleotide at an overhang position.

* * * * *

SEQUENCE LISTING

```
<160> NUMBER OF SEQ ID NOS: 72

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
tatgacggcc agcgcac                                                        17

<210> SEQ ID NO 2
<211> LENGTH: 16
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 2
acgcaacgcg gatgct                                                    16

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cctcccctgg accagctt                                                  18

<210> SEQ ID NO 4
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
ccaccagatg gttcagatct tct                                            23

<210> SEQ ID NO 5
<211> LENGTH: 37
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccaggggagg tagttcttcc cacgcaacgc ggatgct                             37

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggaagaact acctcccctg g                                              21

<210> SEQ ID NO 7
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
aatgatacgg cgaccaccga gatctacaca tacgagatcc gt                       42

<210> SEQ ID NO 8
<211> LENGTH: 24
<212> TYPE: DNA
<213> ORGANISM: Artificial Sequence
<220> FEATURE:
<223> OTHER INFORMATION: Description of Artificial Sequence: Synthetic
```

-continued primer

<400> SEQUENCE: 8
caagcagaag acggcatacg agat                                          24

<210> SEQ ID NO 9
<211> LENGTH: 13
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtgactggag ttc                                                      13

<210> SEQ ID NO 10
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
catacgagat ccgtaatcgg gaagctgaag                                    30

<210> SEQ ID NO 11
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
aatcgggaag ctgaaggcca aggactgtag agacatagat ga                      42

<210> SEQ ID NO 12
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
cactaccgtc ggatgacata ctggagagat ttcatccttg gag                     43

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
atgtcatccg acggtagtga gcaatgacag agtttgacat attgatt                 47

<210> SEQ ID NO 14
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtgctcttcc gatctgttag tgatcaatgt gttaatcata aagtaatt                48

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
atgtcatccg acggtagtga ccttcctcca taatcacatc tgcta                   45

<210> SEQ ID NO 16
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gtgctcttcc gatctctgtt gcaccaacct aatataagga a                       41

<210> SEQ ID NO 17
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
atgtcatccg acggtagtga ggagtgacaa tacagaaaaa aatagagg                48

<210> SEQ ID NO 18
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtgctcttcc gatctgaggg gatttgtatc cgttgttc                           38

<210> SEQ ID NO 19
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
atgtcatccg acggtagtga cctacatctc catacttctt ggcaat                  46

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtgctcttcc gatctatgat cattcctgat gagaaagaga ag          42

<210> SEQ ID NO 21
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
atgtcatccg acggtagtga ggagagagga gtgggccgta             40

<210> SEQ ID NO 22
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
gtgctcttcc gatctaaaga aaattagttt cagaaactcc tcc         43

<210> SEQ ID NO 23
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
atgtcatccg acggtagtga tatccatcaa tacaacacct tccatag     47

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtgctcttcc gatctacagt agatgttaga tgcccttaca ca          42

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
atgtcatccg acggtagtga taccttaaag gttaaggcct gaatg       45

<210> SEQ ID NO 26
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26

```
gtgctcttcc gatctgggga aggtgaagta tcaacaca                               38
```

<210> SEQ ID NO 27
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27

```
atgtcatccg acggtagtga agcaaactca gagggttgga gtac                        44
```

<210> SEQ ID NO 28
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28

```
gtgctcttcc gatcttattt ttgtagctct gacagttgtc tcc                         43
```

<210> SEQ ID NO 29
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
atgtcatccg acggtagtga ccctgactcc atgcaggaga                             40
```

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
gtgctcttcc gatctgttga ctttgatggc tgcctg                                 36
```

<210> SEQ ID NO 31
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31

```
ctaatttaag                                                              10
```

<210> SEQ ID NO 32
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgtgagagca                                                         10

<210> SEQ ID NO 33
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aatcgggaag ctgaagcttg atagtttcta ctttgggttg ataatt              46

<210> SEQ ID NO 34
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cactaccgtc ggatgacata atgggaagac atgtatataa tcttagagat a        51

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
atgtcatccg acggtagtga gcagaaagag ataatattaa ggataatcag          50

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gtgctcttcc gatctgcaga aagagataat attaaggata atcag              45

<210> SEQ ID NO 37
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
atgtcatccg acggtagtga gtcaaatgga tatttgtatc tgaaaaatc           49

<210> SEQ ID NO 38
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
gtgctcttcc gatctatgca tcttgatgat tagaattgca                    40

<210> SEQ ID NO 39
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aatcgggaag ctgaagtcat ggttcacctt tcatttgttc                          40

<210> SEQ ID NO 40
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
cactaccgtc ggatgacata acatcaaact aaaaaatttc cacacaa                  47

<210> SEQ ID NO 41
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
atgtcatccg acggtagtga caaattcaaa aaacggctgc a                        41

<210> SEQ ID NO 42
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
gtgctcttcc gatctaagaa atcaaaagaa gaaaattcta atattca                  47

<210> SEQ ID NO 43
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
aatcgggaag ctgaaggtaa taagacagta gtgaatatca agctacaaa                49

<210> SEQ ID NO 44
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
cactaccgtc ggatgacata agttaggact gagaagaatt tgaaagg                  47

<210> SEQ ID NO 45
<211> LENGTH: 47
<212> TYPE: DNA
<213> ORGANISM: Artificial Sequence
<220> FEATURE:
<223> OTHER INFORMATION: Description of Artificial Sequence: Synthetic primer

<400> SEQUENCE: 45
atgtcatccg acggtagtga gtatctctaa gcaagagaac tgagtgg         47

<210> SEQ ID NO 46
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 46
gtgctcttcc gatctatttg cttatcctgc atctctcag         39

<210> SEQ ID NO 47
<211> LENGTH: 40
<212> TYPE: DNA
<213> ORGANISM: Artificial Sequence
<220> FEATURE:
<223> OTHER INFORMATION: Description of Artificial Sequence: Synthetic primer

<400> SEQUENCE: 47
aatcgggaag ctgaagtttt ctgagggatg aataaggcat         40

<210> SEQ ID NO 48
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 48
cactaccgtc ggatgacata attggcaaca gcccctgat         39

<210> SEQ ID NO 49
<211> LENGTH: 52
<212> TYPE: DNA
<213> ORGANISM: Artificial Sequence
<220> FEATURE:
<223> OTHER INFORMATION: Description of Artificial Sequence: Synthetic primer

<400> SEQUENCE: 49
atgtcatccg acggtagtga tacaatttat atgcagaaat atttatatgc ag         52

<210> SEQ ID NO 50
<211> LENGTH: 39
<212> TYPE: DNA
<213> ORGANISM: Artificial Sequence
<220> FEATURE:
<223> OTHER INFORMATION: Description of Artificial Sequence: Synthetic primer

<400> SEQUENCE: 50
gtgctcttcc gatctatttc tgggttaagg caatagcaa         39

<210> SEQ ID NO 51
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 51
aatcgggaag ctgaagttcc cattctaaac tgtaccctgt t        41

<210> SEQ ID NO 52
<211> LENGTH: 46
<212> TYPE: DNA
<213> ORGANISM: Artificial Sequence
<220> FEATURE:
<223> OTHER INFORMATION: Description of Artificial Sequence: Synthetic primer

<400> SEQUENCE: 52
cactaccgtc ggatgacata atggttaagt tcatgtcata ggaagg        46

<210> SEQ ID NO 53
<211> LENGTH: 43
<212> TYPE: DNA
<213> ORGANISM: Artificial Sequence
<220> FEATURE:
<223> OTHER INFORMATION: Description of Artificial Sequence: Synthetic primer

<400> SEQUENCE: 53
aatcgggaag ctgaagccta tgacatgaac ttaaccatag aaa        43

<210> SEQ ID NO 54
<211> LENGTH: 44
<212> TYPE: DNA
<213> ORGANISM: Artificial Sequence
<220> FEATURE:
<223> OTHER INFORMATION: Description of Artificial Sequence: Synthetic primer

<400> SEQUENCE: 54
cactaccgtc ggatgacata tgagaacttc agggtgagtc tatg        44

<210> SEQ ID NO 55
<211> LENGTH: 49
<212> TYPE: DNA
<213> ORGANISM: Artificial Sequence
<220> FEATURE:
<223> OTHER INFORMATION: Description of Artificial Sequence: Synthetic primer

<400> SEQUENCE: 55
atgtcatccg acggtagtga ttcccaattt tcttattaca caaataaga        49

<210> SEQ ID NO 56
<211> LENGTH: 41
<212> TYPE: DNA
<213> ORGANISM: Artificial Sequence
<220> FEATURE:
<223> OTHER INFORMATION: Description of Artificial Sequence: Synthetic primer

<400> SEQUENCE: 56
gtgctcttcc gatctaaact cttccacttt tagtgcatca a        41

<210> SEQ ID NO 57

<210> SEQ ID NO 57
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aatcgggaag ctgaagttag ttacttatta ggttttggga aacaag            46

<210> SEQ ID NO 58
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cactaccgtc ggatgacata attttgact gcattaagag gtctctagt            49

<210> SEQ ID NO 59
<211> LENGTH: 51
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
atgtcatccg acggtagtga gaaaagacgt ctttaaaata ttttaaatgt t            51

<210> SEQ ID NO 60
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gtgctcttcc gatctaaaat ctaacagcca agtcaaatct g            41

<210> SEQ ID NO 61
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
aatcgggaag ctgaagctgt catgtgtgtc ttgactcaga a            41

<210> SEQ ID NO 62
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cactaccgtc ggatgacata agatgcggtg gggagatatg            40

<210> SEQ ID NO 63
<211> LENGTH: 43

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
atgtcatccg acggtagtga aaggccatga ggactgttat ttg                    43

<210> SEQ ID NO 64
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gtgctcttcc gatctagcca agtctttgga attaacagac                        40

<210> SEQ ID NO 65
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aatcgggaag ctgaagccgc atccagccag gata                              34

<210> SEQ ID NO 66
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
cactaccgtc ggatgacata acaagagtag atgctattct ttccacttt              49

<210> SEQ ID NO 67
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
atgtcatccg acggtagtga tagataggga caaattgaag cagaa                  45

<210> SEQ ID NO 68
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gtgctcttcc gatctcattt ccctacctct aatcaacagt t                      41

<210> SEQ ID NO 69
<211> LENGTH: 48
<212> TYPE: DNA
```

-continued

```
<213> ORGANISM: Artificial Sequence
<220> FEATURE:
<223> OTHER INFORMATION: Description of Artificial Sequence: Synthetic
      primer

<400> SEQUENCE: 69
atgtcatccg acggtagtga gaagtatgaa gtaagacata gtccccaa                  48

<210> SEQ ID NO 70
<211> LENGTH: 46
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gtgctcttcc gatctattaa aatcgatact gagttctaaa atcatc                    46

<210> SEQ ID NO 71
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
aatcgggaag ctgaaggctc tccacaattc taatctcagt tc                        42

<210> SEQ ID NO 72
<211> LENGTH: 52
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
cactaccgtc ggatgacata attgataaga taatatgaaa acacagaatt ca             52
```